(12) United States Patent
Alumot et al.

(10) Patent No.: US 6,952,491 B2
(45) Date of Patent: Oct. 4, 2005

(54) OPTICAL INSPECTION APPARATUS FOR SUBSTRATE DEFECT DETECTION

(75) Inventors: David Alumot, Rehovot (IL); Gad Neumann, Rehovot (IL); Rivka Sherman, Ramat Hasharon (IL); Ehud Tirosh, Jerusalem (IL)

(73) Assignee: Applied Materials, Inc., Santa Clara, CA (US)

( * ) Notice: Subject to any disclaimer, the term of this patent is extended or adjusted under 35 U.S.C. 154(b) by 418 days.

(21) Appl. No.: 09/765,995

(22) Filed: Jan. 19, 2001

(65) Prior Publication Data

US 2002/0039436 A1 Apr. 4, 2002

Related U.S. Application Data

(63) Continuation of application No. 09/298,501, filed on Apr. 23, 1999, now Pat. No. 6,178,257, which is a continuation of application No. 08/984,558, filed on Dec. 3, 1997, now Pat. No. 5,982,921, which is a continuation of application No. 07/790,871, filed on Nov. 12, 1991, now Pat. No. 5,699,447.

(30) Foreign Application Priority Data

Nov. 16, 1990 (IL) .............................. 96362
Oct. 23, 1991 (IL) .............................. 99823

(51) Int. Cl.$^7$ .................. G06K 9/00; G01N 21/00; H04N 7/18
(52) U.S. Cl. .................. 382/149; 356/237.4; 348/133
(58) Field of Search .................. 382/112, 141, 382/144, 148, 149, 145, 181; 356/237.1, 237.2, 237.4, 394; 250/310, 559.45; 348/133; 430/5

(56) References Cited

U.S. PATENT DOCUMENTS

| | | | |
|---|---|---|---|
| 4,131,365 A | * 12/1978 | Pryor | 356/400 |
| 4,532,650 A | 7/1985 | Wihl et al. | 382/8 |
| 4,542,404 A | 9/1985 | Duschl | 358/106 |
| 4,572,662 A | * 2/1986 | Silverman | 356/141.4 |
| 4,589,140 A | 5/1986 | Bishop et al. | 382/8 |
| 4,618,938 A | 10/1986 | Sandland et al. | 364/552 |
| 4,693,608 A | 9/1987 | Kitagawa et al. | 356/394 |
| 4,700,225 A | * 10/1987 | Hara et al. | 250/458.1 |
| 4,764,969 A | 8/1988 | Ohtombe et al. | 382/8 |
| 4,791,586 A | 12/1988 | Maeda et al. | 364/491 |
| 4,805,123 A | 2/1989 | Specht et al. | 364/559 |
| 4,845,558 A | 7/1989 | Tsai et al. | 358/106 |
| 4,872,052 A | 10/1989 | Liudzius et al. | 358/106 |

(Continued)

FOREIGN PATENT DOCUMENTS

| | | | | |
|---|---|---|---|---|
| JP | A-53-138387 | 2/1978 | | |
| JP | A-55-17443 | 2/1980 | | |
| JP | 60-245240 | 12/1985 | | |
| JP | 61-245007 | 10/1986 | | |
| JP | 62-150142 | 7/1987 | | |
| JP | 62-173731 | 7/1987 | | |
| JP | A-63-286752 | 11/1988 | | |
| JP | A-2-163879 | 6/1990 | | |
| WO | WO-9120054 | * 12/1991 | ............ | G06K/9/00 |

Primary Examiner—Mehrdad Dastouri
(74) Attorney, Agent, or Firm—Sughrue Mion PLLC

(57) ABSTRACT

A method and apparatus for inspecting the surface of articles, such as chips and wafers, for defects, includes a first phase of optically examining the complete surface of the article inspected at a relatively high speed and with a relatively low spatial resolution, and a second phase of optically examining with a relatively high spatial resolution only the suspected locations for the presence or absence of a defect therein.

10 Claims, 40 Drawing Sheets

U.S. PATENT DOCUMENTS

| | | | | |
|---|---|---|---|---|
| 4,899,219 A | * | 2/1990 | Mount, II | 358/107 |
| 4,926,489 A | | 5/1990 | Danielson et al. | 382/8 |
| 4,972,493 A | | 11/1990 | Chemaly | 382/8 |
| 4,979,223 A | * | 12/1990 | Manns et al. | 382/149 |
| 5,051,825 A | * | 9/1991 | Cochran et al. | 358/106 |
| 5,103,304 A | * | 4/1992 | Turcheck, Jr. et al. | 358/101 |
| 5,133,601 A | | 7/1992 | Cohen et al. | 356/359 |
| 5,159,646 A | | 10/1992 | Kumagai | 382/34 |
| 5,185,812 A | | 2/1993 | Yamashita et al. | 382/8 |
| 5,204,910 A | | 4/1993 | Lebeau | 382/8 |
| 5,249,035 A | | 9/1993 | Yamanaka | 356/376 |
| 5,455,870 A | | 10/1995 | Sepai et al. | 283/147 |
| 5,548,326 A | * | 8/1996 | Michael | 348/126 |
| 5,699,447 A | | 12/1997 | Alumot | 382/145 |
| 5,982,921 A | | 11/1999 | Alumot et al. | 382/146 |

* cited by examiner

FIG. 6
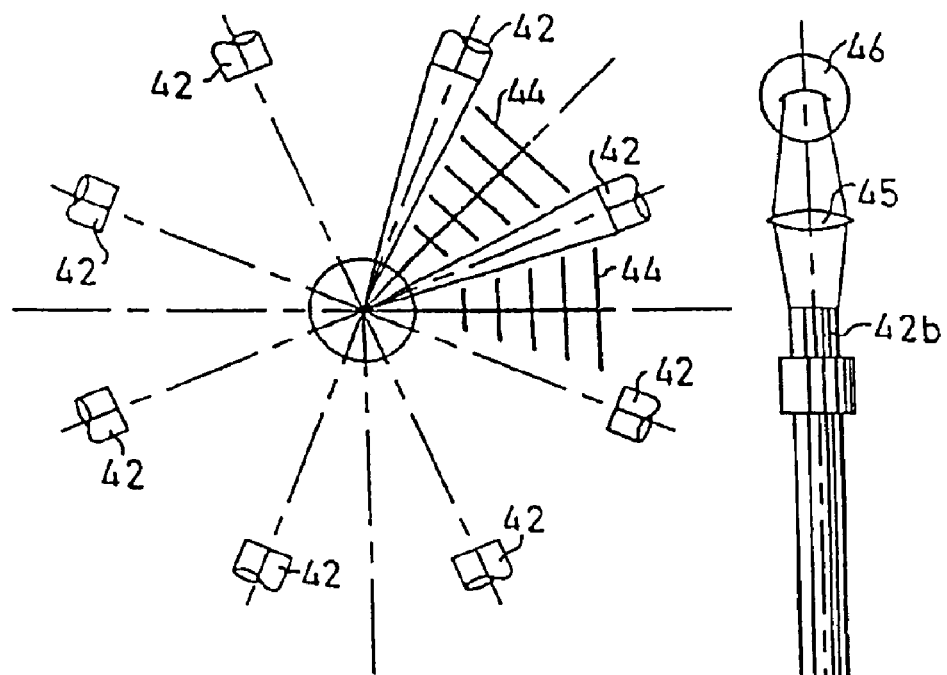
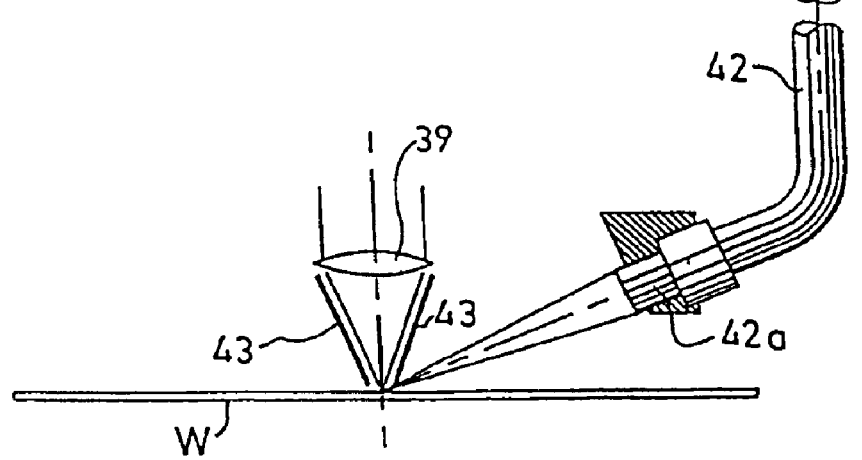
FIG. 7

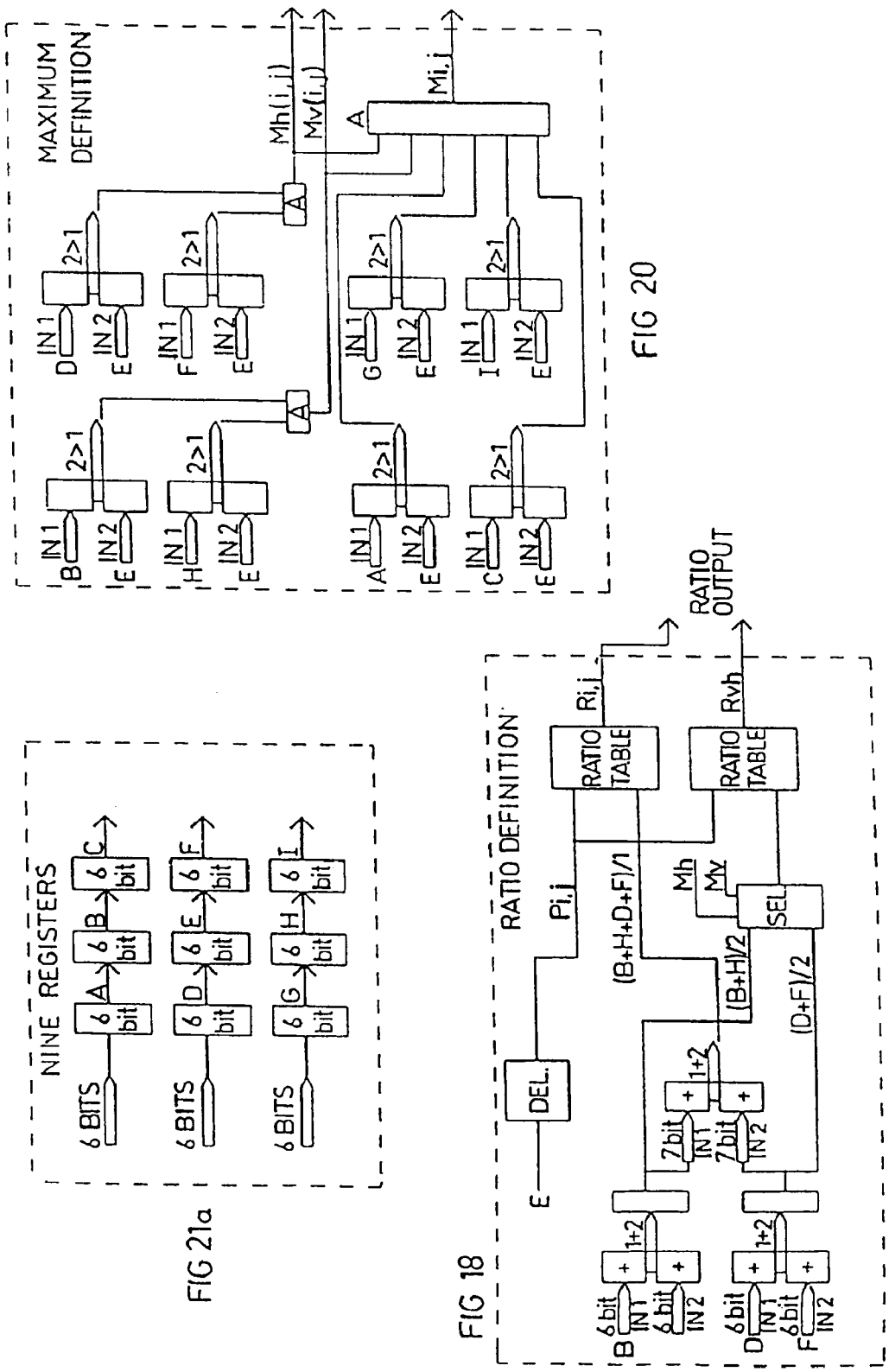

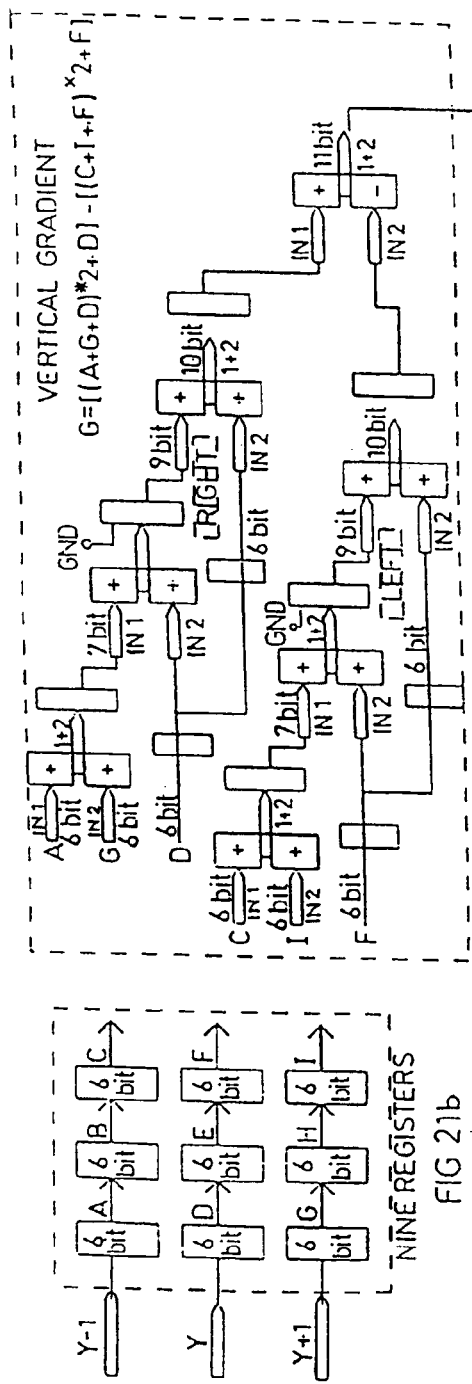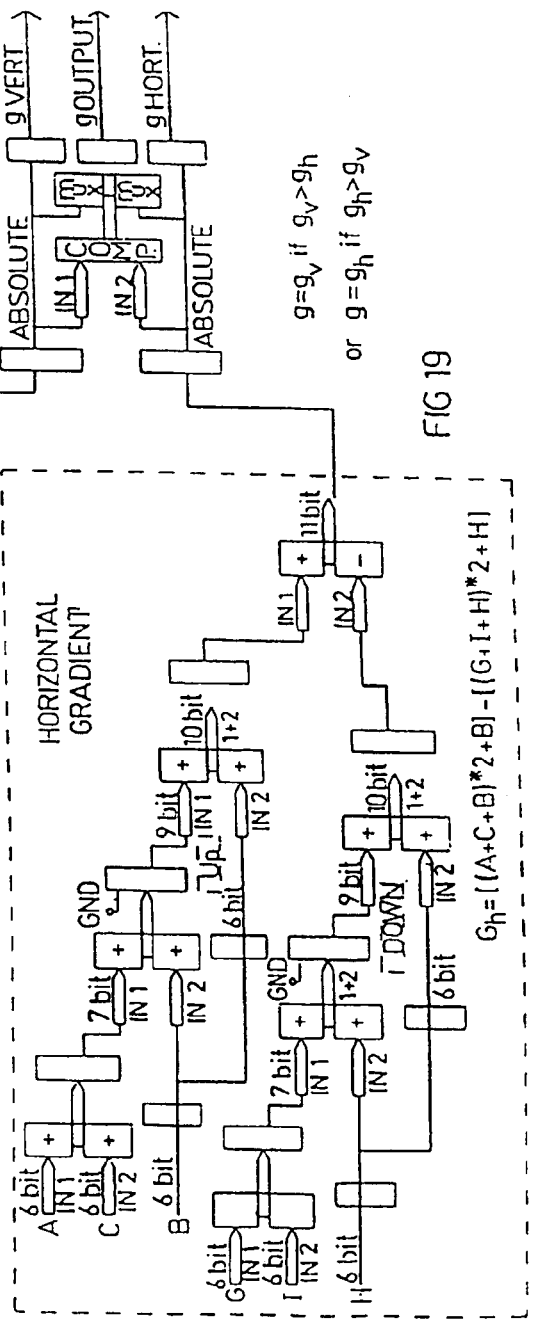

OPTICAL INSPECTION APPARATUS FOR SUBSTRATE DEFECT DETECTION

This is a continuation of application Ser. No. 09/298,501 filed Apr. 23, 1999, now U.S. Pat. No. 6,178,257, which is a continuation of application Ser. No. 08/984,558 filed Dec. 3, 1997, now U.S. Pat. No. 5,982,921, which is a continuation of application Ser. No. 07/790,871 filed Nov. 12, 1991, now U.S. Pat. No. 5,699,447. The disclosures of all of these are incorporated herein by reference.

FIELD AND BACKGROUND OF THE INVENTION

The present invention relates to a method and apparatus for optically inspecting the surface of an article for defects. The invention is particularly useful for optically inspecting patterned semiconductor wafers used in producing integrated circuit dies or chips, and the invention is therefore described below particularly with respect to this application.

The inspection of unpatterned semiconductor wafers for surface-lying particles is relatively simple and can be easily automated. In one known type of such system, the wafer is scanned by a laser beam, and a photodetector detects the presence of a particle by collecting the light scattered by the particle. However, the inspection of patterned semiconductor wafers for defects in the pattern is considerably more difficult because the light scattered by the pattern overwhelms the light scattered from the particles or defects, thereby producing high rates of false alarms.

The existing inspection systems for inspecting patterned wafers are generally based on analyzing high resolution two-dimensional images of the patterned wafer utilizing an opto-electric converter, such as a CCD (charge-coupled device), on a pixel-by-pixel basis. However, the extremely large number of pixels involved makes such systems extremely slow. For this reason, the inspection of patterned wafers is done at the present time almost only for statistical sampling purposes. As a result, microdefects in patterned semiconductor wafers remain largely undetected until a considerable number of such wafers have been fabricated and have begun to exhibit problems caused by the defects. The late discovery of such defects can therefore result in considerable losses, low yields, and large downtimes.

There is therefore an urgent need to inspect patterned semiconductor wafers at relatively high speeds and with a relatively low false alarm rate in order to permit inspection during or immediately after the fabrication of the wafer so as to quickly identify any process producing defects and thereby to enable immediate corrective action to be taken. This need is made even more critical by the increasing element density, die size, and number of layers in the integrated circuits now being produced from these wafers, and now being designed for future production, which requires that the number of microdefects per wafer be drastically reduced to attain a reasonable die yield.

OBJECTS AND BRIEF SUMMARY OF THE INVENTION

An object of the present invention is to provide a novel method and apparatus having advantages in the above respects for inspecting the surface of articles for defects.

In particular, an object of the invention is to provide a method and apparatus for automatically inspecting patterned semiconductor wafers characterized by a relatively high speed and relatively low rate of false alarms such that the patterned wafers may be tested while the wafers are in the production line to quickly enable the fabrication personnel to identify any process or equipment causing yield reduction, to receive fast feedback information after corrective actions, and to predict potential yield loss.

A still further object of the invention is to provide an inspection method and apparatus which are capable of inspecting all the critical layers, and which supply data on defects caused by the presence of particles and defects in the patterns.

According to one aspect of the present invention, there is provided a method of inspecting the surface of an article for defects by: optically examining, in a first phase examination, the complete surface of the article and electrically outputting information indicating locations on the article suspected of having defects; storing the suspected locations in a storage device; and, in a second phase examination, optically examining with high resolution only the suspected locations of the article's surface for determining the presence or absence of a defect in the suspected locations; characterized in that the first phase examination is effected by optically scanning the complete surface of the article at a high speed with an optical beam of small diameter. Thus, by selecting the diameter of the optical beam used in the first phase examination, the first phase examination may be made at any desired resolution, as compared to the second phase examination, according to the particular application.

According to further features of the invention, the first examining phase is effected by optically scanning the complete article surface to be inspected with a laser beam of small diameter; and the second examining phase is automatically effected immediately after the first phase by imaging only the suspected locations on an image converter which converts the images to electrical signals and then analyzes the electrical signals.

According to still further features in preferred embodiments of the invention described below, the surface of the article to be inspected includes a pattern, e.g., a patterned wafer used for producing a plurality of integrated-circuit dies or chips, The first examination phase is effected by making a comparison between the inspected pattern and another pattern, serving as a reference pattern, to identify locations on the inspected pattern wherein there are sufficient differences with respect to the reference pattern to indicate a high probability of a defect in the inspected pattern. The second examination phase is also effected by making a comparison between the inspected pattern and the reference pattern, to identify locations on the inspected pattern wherein the comparison shows sufficient differences with respect to the reference pattern to indicate the presence of a defect in the suspected location of the inspected pattern.

The reference pattern may be a pattern on another like article (e.g., die-to-die comparison), another like pattern on the same article (repetitive pattern comparison), or data stored in a database (die-to-database comparison).

It will thus be seen that the novel method of the present invention primarily monitors changes in the defect density while maintaining a high throughput with a relatively low false alarm rate. Thus, the first examination is done at a relatively high speed and with a relatively low spatial resolution such as with a laser beam of small diameter to indicate only suspected locations having a high probability of a defect; and the second examination is done with a relatively high spatial resolution but only with respect to the suspected locations having a high probability of a defect. The sensitivity of the two phases may be adjusted according to the requirements for any particular application. Thus, where the application involves a relatively low number of defects, the sensitivity of the first examination phase may be increased by using a very small diameter laser beam to detect very small defects at a high speed but at the expense of an increased false alarm rate. However, since only relatively few suspected locations are examined in the second phase, the overall inspection can be effected relatively quickly to enable the fabrication personnel to identify defects caused by any process or equipment, and to immediately correct the cause for such defects.

According to a further feature of the invention, the first examining phase is effected by generating a first flow of N different streams of data representing the pixels of different views of the inspected pattern unit; generating a second flow of N different streams of data representing the pixels of different views of the reference; and comparing the data of the first flow with the data of the second flow to provide an indication of the suspected locations of the inspected surface of the article having a high probability of a defect.

According to still further features of the invention, the pattern is based on a grid of angularly-spaced lines (e.g., 45° spacing); and the N streams of data in each flow are generated by a circular array of light collectors. The light collectors are located to collect the light in regions midway between the angularly-spaced lines of the grid. Such an arrangement minimizes the amount of pattern-reflected light, collected by the light collectors; that is, such an arrangement does not see most of the pattern, except pattern irregularities, corners and curves.

Preferably, there are eight light collectors each located to collect the light in a region midway between each pair of the angularly-spaced lines of the grid; it is contemplated, however, that the system could include another member, e.g., four such light collectors equally spaced between the grid lines.

According to still further features of the invention, the second examining phase is effected by imaging on a converter each suspected location of the inspected pattern unit and the corresponding location of the reference pattern unit to output two sets of electrical signals corresponding to the pixels of the inspected pattern unit and the reference pattern unit, respectively; and comparing the pixels of the inspected pattern unit with the corresponding pixels of the reference pattern unit to indicate a defect whenever a mismatch of a predetermined magnitude is found to exist at the respective location. Each suspected location of the inspected pattern unit and the reference pattern unit is imaged at a plurality of different depths, and the electric signals of one set are shifted with respect to those of the other set to match the respective depths of the images.

The invention also provides apparatus for inspecting articles, particularly patterned semiconductor wafers, in accordance with the above method.

Further features and advantages of the invention will be apparent from the description below.

BRIEF DESCRIPTION OF THE DRAWINGS

The invention is herein described, by way of example only, with reference to the accompanying drawings, wherein:

FIG. 6 is a diagram more particularly illustrating the disposition of the light collectors in FIG. 5, FIG. 6a showing a variation;

FIGS. 7 and 7a are diagrams illustrating one of the light collectors in the arrangements of FIGS. 6 and 6a, respectively;

FIGS. 18, 19 and 20 are block diagrams more particularly illustrating the Ratio, Gradient and Maximum Definition Calculator in the system of FIG. 17;

FIGS. 21a and 21b illustrate the nine registers in the Ratio Calculator and Gradient Calculator, respectively;

DESCRIPTION OF A PREFERRED EMBODIMENT

Overall System

Figure 1:
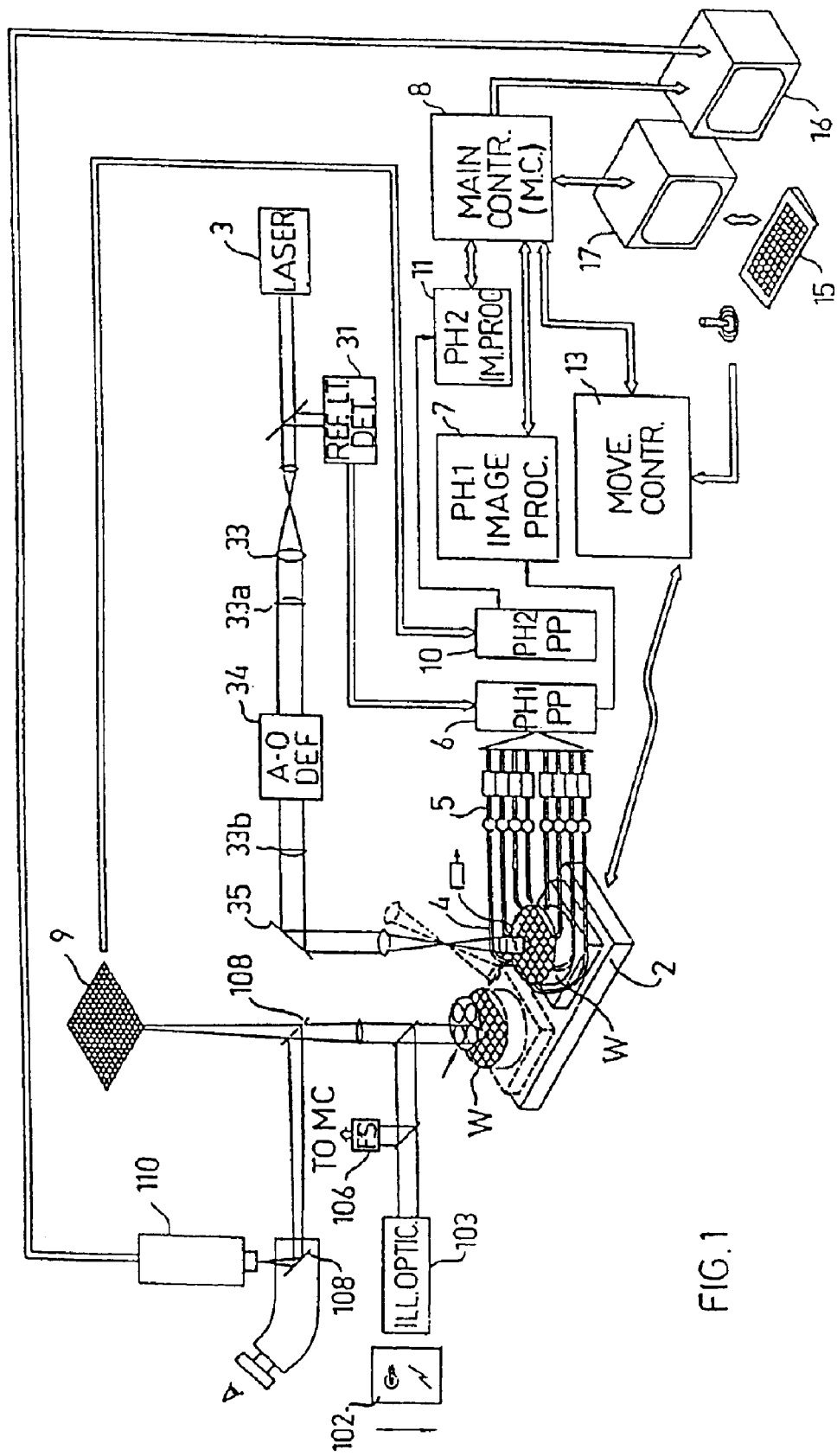
FIG. 1 is a pictorial illustration of one form of apparatus constructed in accordance with the present invention.

The system illustrated in the drawings is designed particularly for automatically inspecting patterned semiconductor wafers having a plurality of like integrated-circuit dies each formed with like patterns. The system inspects each pattern, called the inspected pattern, by comparing it with at least one other pattern on the wafer, serving as the reference pattern, to detect any differences which would indicate a defect in the inspected pattern.

The inspection is made in two phases: In the first phase, the complete surface of the wafer is inspected at a relatively high speed and with a relatively low spatial resolution; and information is outputted indicating suspected locations on the wafer having a high probability of a defect. These locations are stored in a storage device. In the second phase, only the suspected locations stored in the storage device are examined with a relatively high spatial resolution; and a determination is made as to the presence or absence of a defect. This facilitates identification and correction of the process that created the defect.

Figure 2:
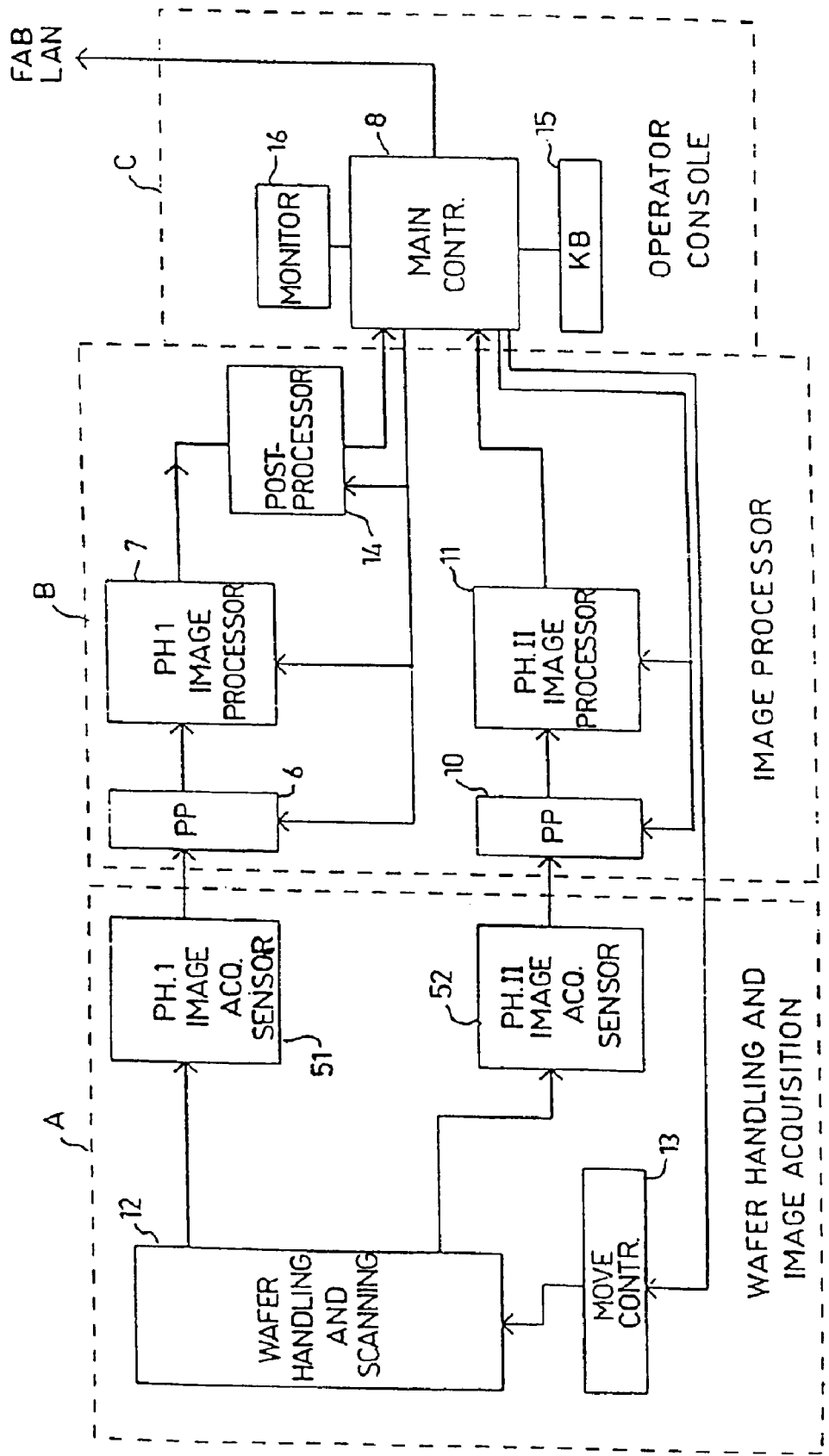
FIG. 2 is a block diagram of the apparatus of FIG. 1.
Figure 3:
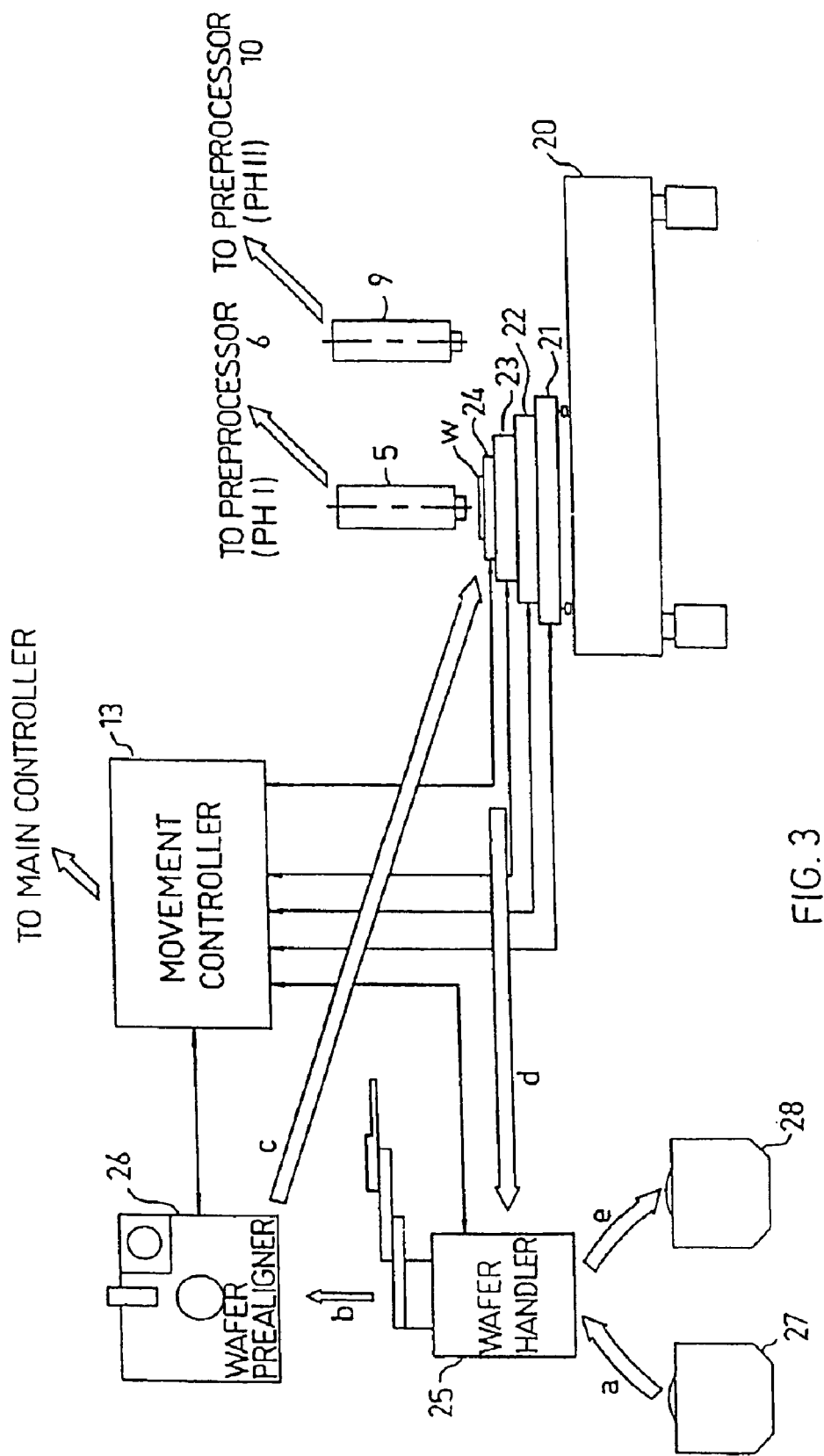
FIG. 3 is a diagram illustrating the wafer handling and image-acquisition system in the apparatus of FIGS. 1 and 2.

The inspection apparatus illustrated in FIGS. 1–3 of the drawings includes a table 2 for receiving the wafer W to be inspected. The first phase inspection of the wafer is by a laser 3 outputting a laser beam which scans the complete surface of the wafer W; and a plurality of light collectors 4 arranged in a circular array to collect the light scattered from the wafer and to transmit the scattered light to a plurality of detectors 5. The outputs of the detectors 5 are fed via a Phase I preprocessor 6 to a Phase I image processor 7, which processes the information under the control of a main controller 8. The Phase I image processor 7 processes the outputs of the detectors 5 and produces information indicating suspected locations on the wafer having a high probability of a defect. These suspected locations are stored within a storage device in the main controller 8.

Only the suspected locations having a high probability of a defect are examined by the Phase II examining system. This system includes an optic system for imaging the suspected location on an opto-electric converter, e.g., a CCD matrix 9, which converts the images to electric signals. These signals are fed via a Phase II preprocessor 10 to a Phase II image processor 11 which, under the control the main controller 8, outputs information indicating the presence or absence of a defect in each suspected location examined in Phase II.

In the block diagram illustrated in FIG. 2, the table 2 of FIG. 1, and associated elements involved in the wafer handling system, are indicated generally by block 12, Table 2 is controlled by a movement control system, indicated by block 13, to effect the proper positioning of the wafer on the table 2 in each of the Phase I and Phase II examination phases, and also the scanning of the wafer W in the Phase I examination.

The light detectors 5 of FIG. 1 are included in the Phase I image acquisition sensor indicated by block $S_1$ in FIG. 2; and the opto-electric converter 9 of FIG. 1 is included within the Phase II image acquisition sensor indicated by block $S_2$ in FIG. 2.

FIG. 2 also illustrates a post processor 14 processing the information from the Phase I processor 7; the main controller 8 which manages and synchronizes the data and controls the flow; a keyboard 15 enabling the operator to input information into the main controller 8; and a monitor 16 enabling the operator to monitor the processing of the information.

All the elements in the wafer handling and image acquisition subsystem for both phases are included within the broken-line box generally designated A in FIG. 2; all the elements of the image processor subsystem (both the algorithms and the hardware) for both phases are indicated by the broken-line block B; and all the elements in the operator console subsystem are indicated by the broken-line block C. The latter subsystem includes not only the main controller 8, keyboard 15, and monitor 16, but also a graphic terminal unit, shown at 17 in FIG. 1.

The other elements illustrated in FIG. 1 are described more particularly below in connection with their respective subsystems.

Wafer Handling and Image Acquisition

FIG. 3 more particularly illustrates the wafer handling and image acquisition subsystem 5a (FIG. 2).

This subsection includes the table 2 which is of a large mass (such as of granite). It is mounted on vibration isolators 20 to dampen high frequency vibrations from the outside world.

The subsection illustrated in FIG. 3 also includes the movement controller 13 controlled by the main controller 8. Movement controller 13 controls a one-directional scanning stage 21. This stage moves a vacuum chuck 24 which holds the wafer flattened during its movement in one orthogonal direction with respect to the Phase I sensors 5, as the laser beam from the laser 3 is deflected in the other orthogonal direction to scan the complete surface of the wafer during the Phase I examination.

Movement controller 13 further controls a two-dimensional scanning stage 22 effective, during the Phase II examination, to position the wafer at any desired position with respect to the Phase II detector 9 (the CCD matrix). As described in detail below, the control of one of the axes of this stage serves also during the Phase I examination. Movement controller 13 further controls a rotation/level/focus stage 23, which rotates the wafer about its axis to align it angularly, to level it, and to keep it in focus during scanning. Stage 23 also roves the vacuum chuck 24 and its wafer towards or away from the Phase II sensor 9 to enable producing a plurality of images at different depths during the Phase II examination, as will be described more particularly below.

FIG. 3 also schematically illustrates a wafer handler 25 which transfers the wafer W between the vacuum chuck 24, a wafer prealigner 26, and cassettes 27 and 28. The wafer prealigner 26 initially aligns the wafer angularly and centers it, and also schematically illustrated in FIG. 3 is an optical character recognition unit 29 which reads the wafer identification code.

The foregoing components are generally individually well-known and are therefore not described herein in detail.

Phase I Optic System

Figure 4:
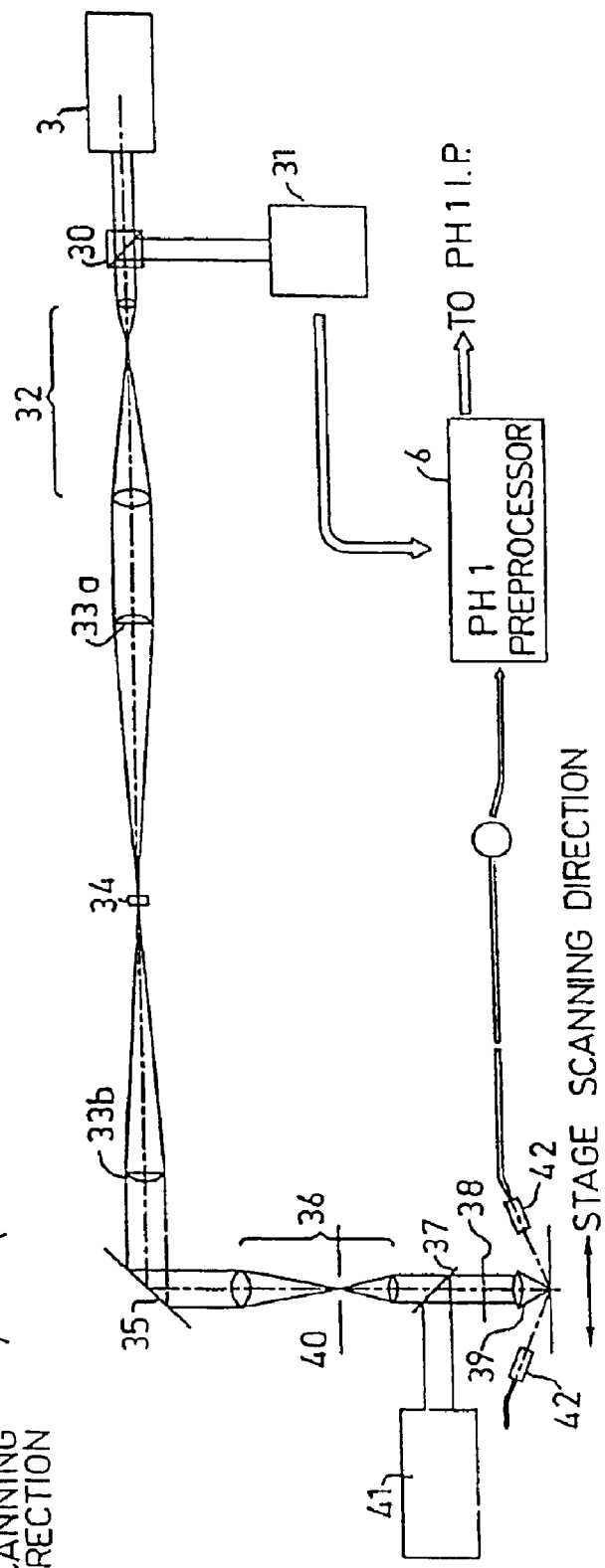
FIG. 4 is a diagram illustrating the optic system in the first examining phase of the apparatus of FIG. 1.

As shown in FIG. 4, the laser 3 (e g., an argon laser) outputs a laser beam which is passed through a polarizer beam splitter 30 oriented in such a way to transmit the laser light to the wafer W, but to reflect the reflected light from the wafer to a photodetector 31. The latter outputs an electric signal controlling the Phase I preprocessor 6. The laser beam from beam splitter 30 is passed through a beam expander 32, then through a cylindrical lens 33a, a deflector 34, another cylindrical lens 33b, a folding mirror 35, a multi-magnification telescope 36, a beam splitter 37, a quarter wavelength plate 38 which converts the linearly polarized light to a circularly polarized light and vice versa, and finally through a microscope objective 39, which focuses the laser beam on the wafer W.

The beam expander 32 expands the laser beam diameter to fill the optic aperture of the deflector 34, and the cylindrical lens 33a focuses the laser beam onto the deflector 34. Deflector 34 is an acousto-optic deflector. It scans the laser beam in one orthogonal direction in a sawtooth pattern in the time domain, while the motion controller moves the table (and the wafer thereon) in the other orthogonal direction in order to scan the complete surface of the wafer. The folding mirror 35 reflects the laser beam into the multi-magnification telescope 36, which matches the laser beam diameter and scan aperture to fit the input requirements of standard microscopic optics. Slit 40 within telescope 36 permits only the first order defracted light of the laser beam to impinge the wafer W.

Beam splitter 37 passes a part of the beam to the wafer, as described above, and reflects another part to an autofocus unit 41, which determines whether the wafer is in the focus of the microscope objective 39. The autofocus unit can be a standard one, such as the one used in the Leitz Ergolux microscope.

Figure 5:
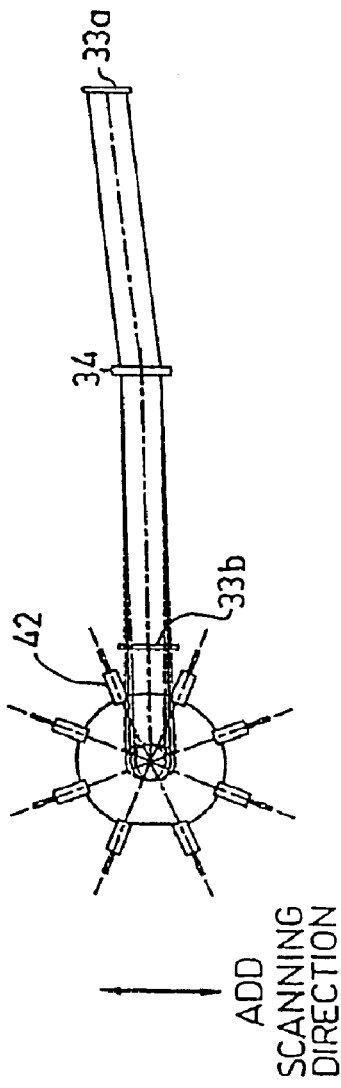
FIG. 5 is a top plan view illustrating the disposition of the light collectors in the optic system of FIG. 4.
Figures 6A, 7A:
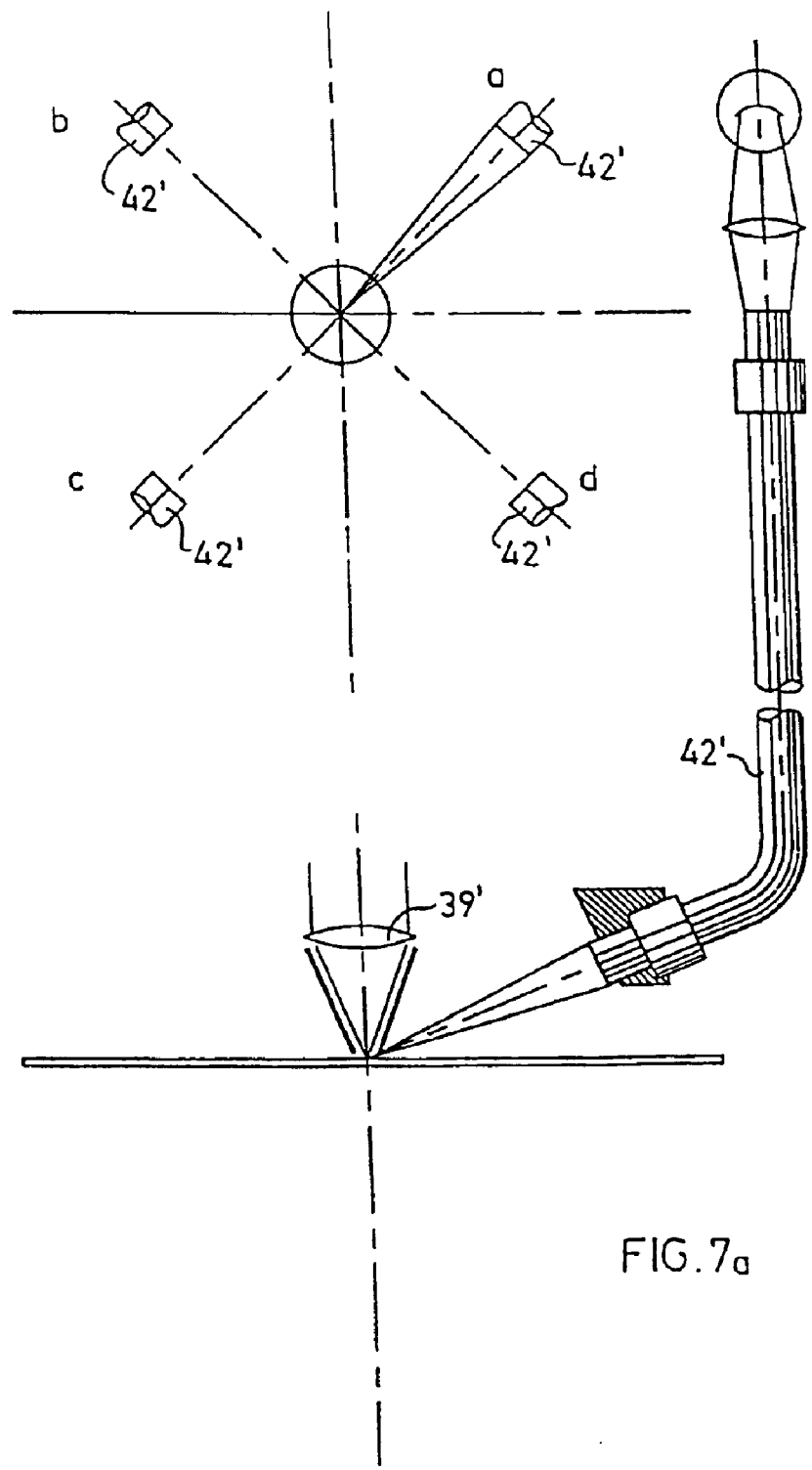

The light reflected from the laser beam by the wafer W being inspected is collected by a plurality of light collectors 42 arranged in a circular array around the objective lens 39, as shown more particularly in FIGS. 5 and 6. The pattern on the wafer W is based on a grid of lines spaced 45° from each other. The circular array of light collectors 42 are located to collect the light in the regions midway between the angularly-spaced lines of the grid, in order to minimize the amount of pattern-reflected light collected by them. In the example illustrated in FIGS. 5 and 6, there are eight of such light collectors 42, each spaced midway between two adjacent grid lines. The apparatus, however, could include only four of such light collectors, as described more particularly below with respect to FIGS. 6a, 7a and 8a.

Baffles 43 (FIG. 7) keeps spurious laser light from reaching the wafer W. Further baffles 44 (FIG. 6) between the light collectors 42 limit the field of view of the light collectors 42 to the predetermined region on the wafer to minimize the amount of spurious laser light collected by them.

Each of the light collectors 42 includes an optic fibre having an inlet and 42a (FIG. 7) adjacent to the point of impingement of the laser beam on the wafer W, in order to collect the light scattered by the wafer, and an outlet end 42b adjacent a lens 45 for focussing the light onto a photodetector sensor 46.

Figure 8:
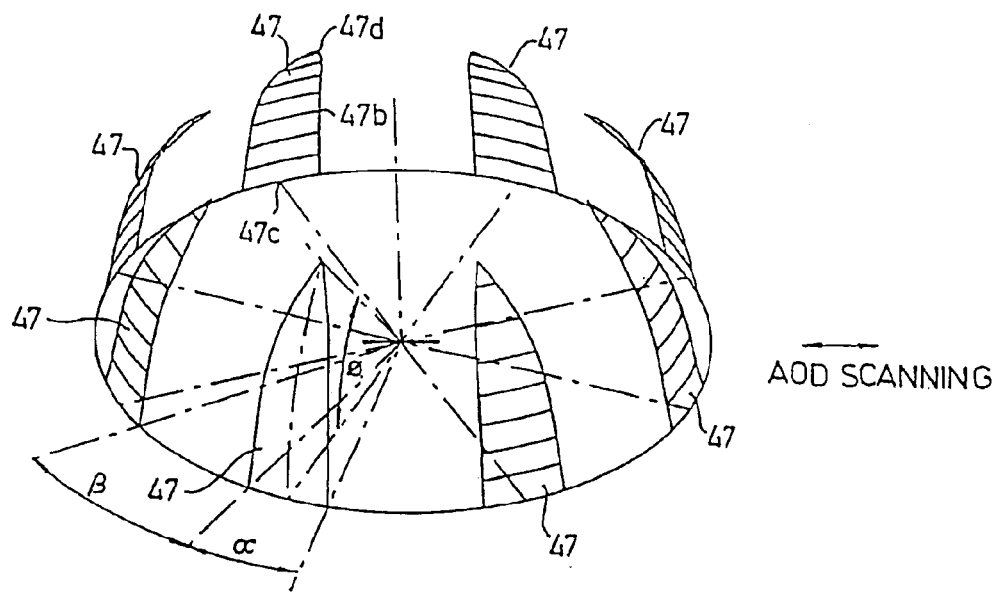
FIGS. 8 and 8a are diagrams more particularly illustrating the light collecting zones in the arrangements of FIGS. 6 and 6a, respectively.

The inlet end 42a of each optic fibre is confined to a shaped, curved region, as more particularly illustrated at 47 in FIG. 8. This end of each region has a pair of sides 47a, 47b, converging from a base 47c, which base is located substantially parallel to the table 2 receiving the wafer W to be inspected. The two sides 47a, 47b converge to a pointed tip 47d overlying the table receiving the wafer.

As shown in FIG. 8, the inlet ends of the optic fibres 42 thus define light collecting zones α, separated by non-collecting zones β. In the illustrated example, the width of each light-collecting zone α is 16° at the bottom surface (47c), and its height (φ) is 49°. Such an arrangement minimizes the pattern-reflected light, and maximizes the defect-reflected light, collected by the light collectors.

Figure 8A:
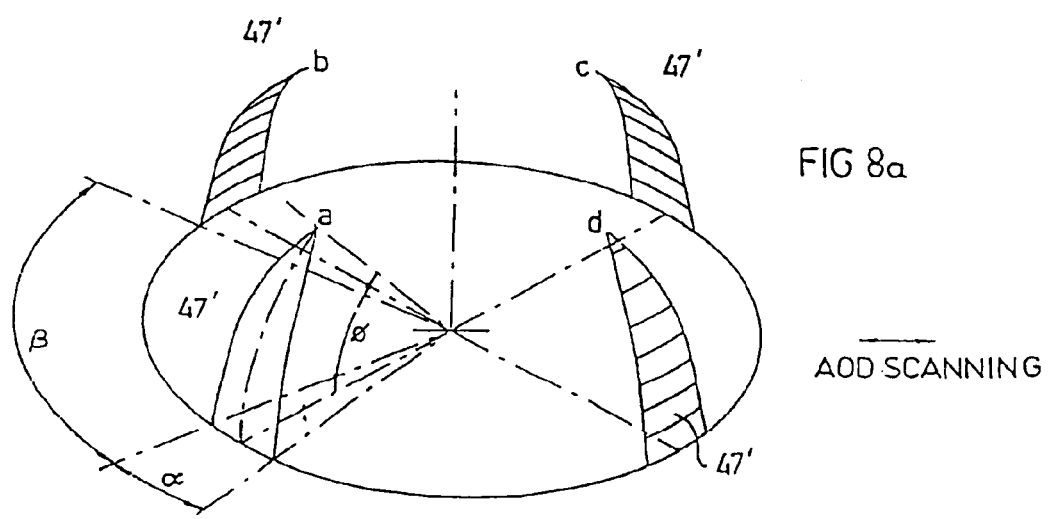

Another example of the light-gathering optics which may be used is illustrated in FIGS. 6a, 7a and 8a, corresponding to the above-described FIGS. 6, 7 and 8, respectively. In this example, there are only four light collectors, therein designated 42', located at angles of 45°, 135°, 225° and 315°, respectively. This configuration is useful when the object to be inspected consists of lines in only two orthogonal directions (0° and 90°). Another advantage of this configuration is that the objective 39' may have a higher numerical aperture, and thus the spot size used for scanning may be smaller. The light collecting zones in this configuration are illustrated at 47' in FIG. 8a. As one example, the width a of the light collecting zones may be 30°, and their height may be 45°.

Figure 9:
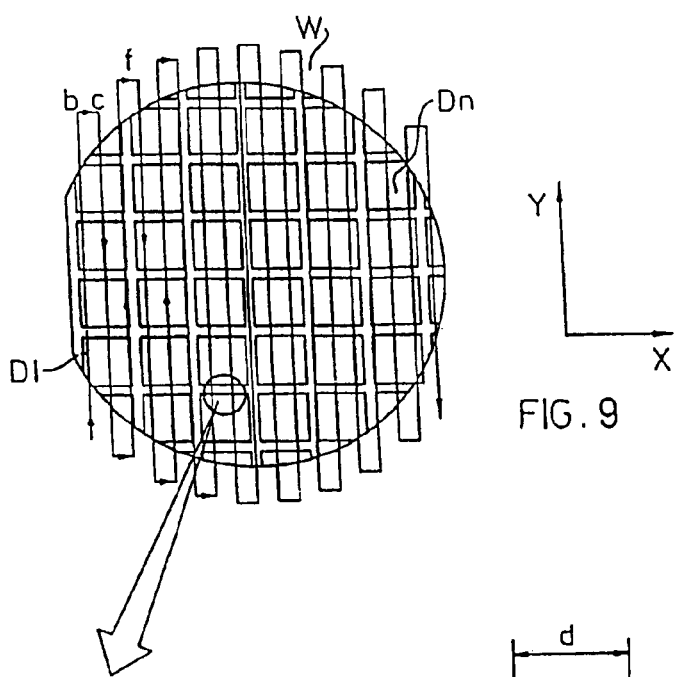
FIGS. 9–11 are diagrams illustrating the manner of scanning the wafer in the Phase I examination.

As shown in FIG. 9, the wafer W being inspected is formed with a plurality of integrated-circuit dies $D_1$–$D_n$ each including the same pattern. In the Phase I examination, the complete surface of the wafer is scanned by the laser beam 3, and the resulting scattered light is collected by the above-described light collectors 42 in order to detect defects, or at least those suspected areas having a high likelihood of including a defect and therefore to be more carefully examined during the Phase II examination. As also indicated above, during the Phase I examination (and also the Phase II examination), the pattern of one die D, serving as the inspected pattern, is compared with the light pattern of at least one other die, serving as the reference pattern, to determine the likelihood of a defect being present in the inspected pattern.

Figure 10:
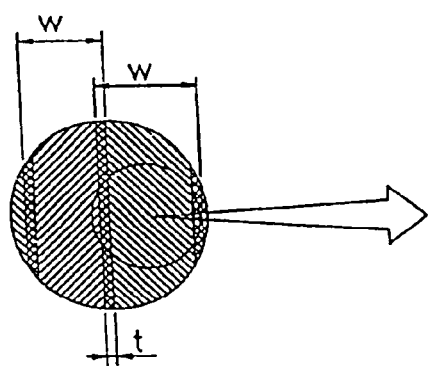
Figure 11:
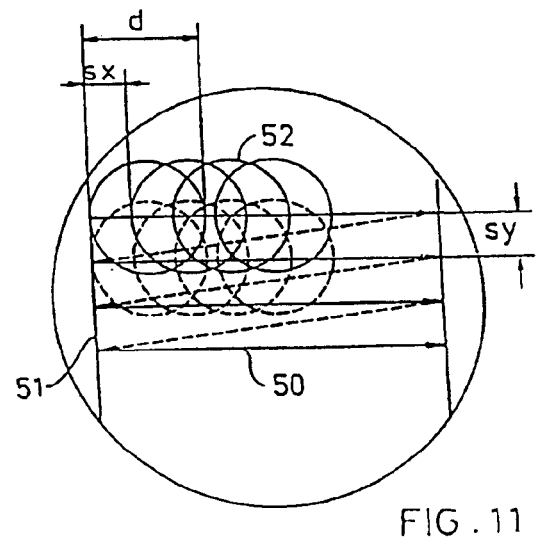

FIGS. 9–11 illustrate the manner of carrying out the scanning of the wafer in the Phase I examination.

Thus, as shown in FIG. 9, the laser beam is deflected in the X-direction by the acousto-optic deflector 34 (FIG. 4) so as to form a scanning line shown at 50 in FIG. 11. At the same time, the scanning stage 21 of the table 2 supporting the wafer W moves the wafer beneath the wafer spot at a continuous constant velocity in the Y-direction, to thereby produce a raster scan indicated at 51 in FIG. 11. In the example illustrated, the scanning length of line 50 is 1 mm (1,000 microns); the distance between two adjacent lines $S_y$ is 0.6 microns; and the distance equal to the sampling distance ($S_x$) in the X-direction is similarly 0.6 microns. The spot size of the laser beam, shown at 52, is about 3.0 microns (i.e., covering approximately 5 sample points).

Thus, the scanning stage 21 scans the wafer between the points a and b in the Y-direction, as shown in FIG. 9. As a result, an area is covered having a width (w) of about 1 mm, and a length equal to the distance between point a and b.

The wafer is then moved in the X-direction from point b to point c (FIG. 9) by the scanning stage 22 (FIG. 3), and the area between points c and d is then scanned, and so forth.

The scanning is done in such a way that there is an overlap (t, FIG. 10) between adjacent stripes scanned by the laser beam 52. In the example illustrated in the drawings, the overlap (t) is 0.2 mm.

In this manner, different dies on the same wafer are continuously scanned to produce the scattered light collected by the light collectors 42 (or 42', FIGS. 6a–8a) so as to enable a die-by-die comparison to be made of each die, called the inspected die, with another die, called the reference die, to produce an indication of the probability of a defect in the inspected die.

As indicated earlier, the Phase I examination system may include eight light detectors 46 (or four light detectors where the variation of FIGS. 6a–8a is used) for inspecting the wafer for defects. However, it may also include a further detector (a reflected light detector) to provide additional information for the registration procedure. Thus, the misalignment may be detected from the reflected light detector image by computing the cross-correlation between a rectangle of pixels in the inspected image, and the rectangle of pixels in the reference image in all possible misalignments. This information may be used where the score matrix computed in the alignment control circuit does not provide a significant indication of the correct misalignment.

Phase I Image Processor

The Phase I examination is effected by: (a) generating a first flow of N streams of data (N being the number of light collectors 42, or 42') representing the pixels of different images of the inspected pattern; (b) generating a second flow of N streams of data representing the pixels of different images of the reference pattern; and (c) comparing the data of the first flow with the data of the second flow to provide an indication by the comparison of the suspected locations of the inspected pattern having a high probability of a defect. The comparison is effected by correcting any misalignment between the two flows of data; comparing the data of each stream of the first flow with the data of the corresponding stream of the second flow to provide a difference or alarm value indicating the significance of the presence of a suspected pixel in the stream; and detecting a defect at a pixel location according to N difference or alarm values corresponding to the N streams of data.

Figure 12:
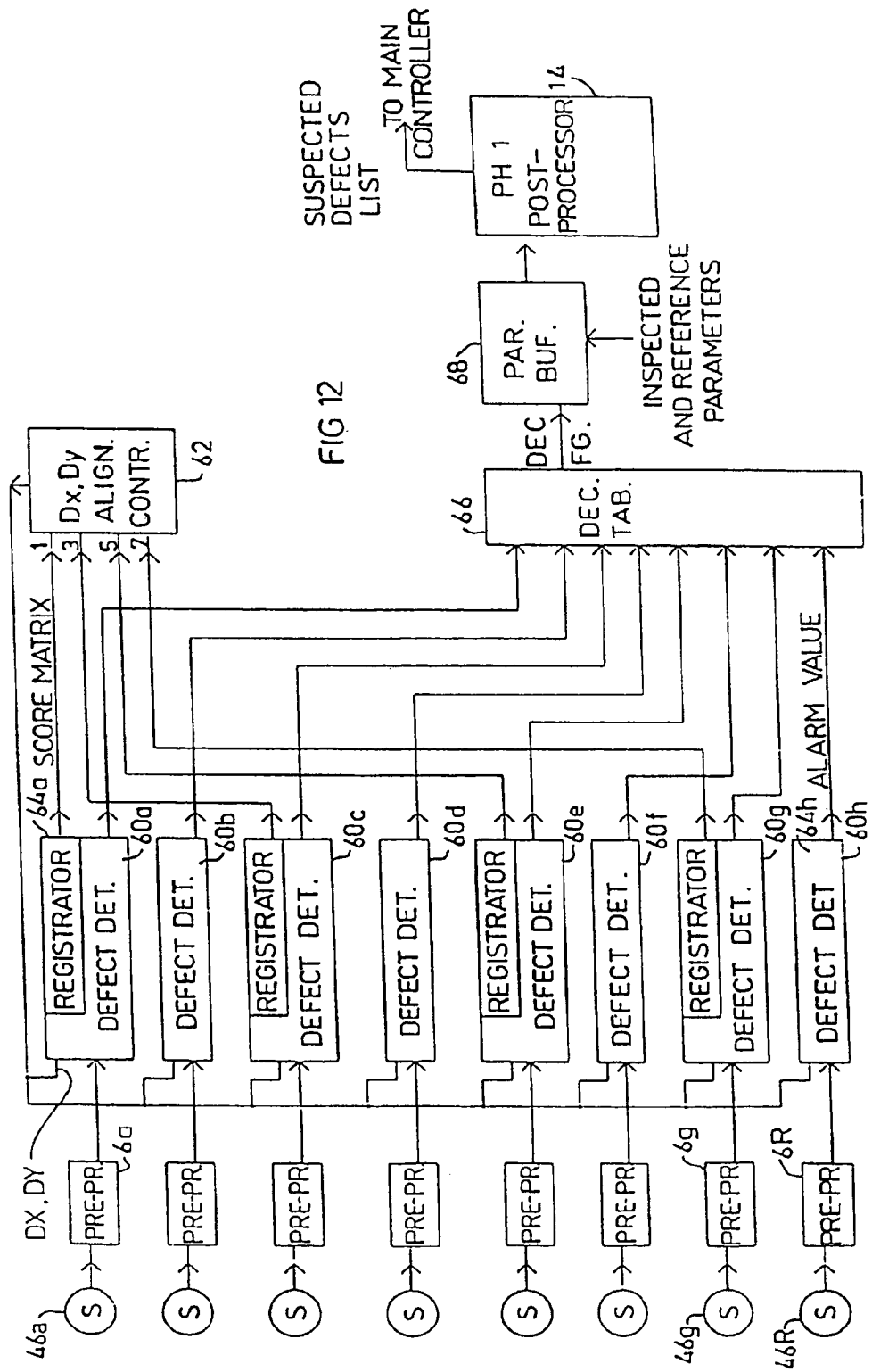
FIG. 12 is a block diagram illustrating the Phase I processing system.

FIG. 12 is a functional block diagram of the Phase I image processor. It includes an input from each of the eight sensors 46a–46b (each corresponding to photodetector sensor 46 in FIG. 7) to their respective preprocessors 6a–6g. The sensors convert the light signals to analog electrical signals, and the preprocessors sample the latter signals at pixel intervals and convert them to digital data. The outputs of the preprocessors are thus in the form of streams of pixel values forming a digital version of the image.

Figure 13:
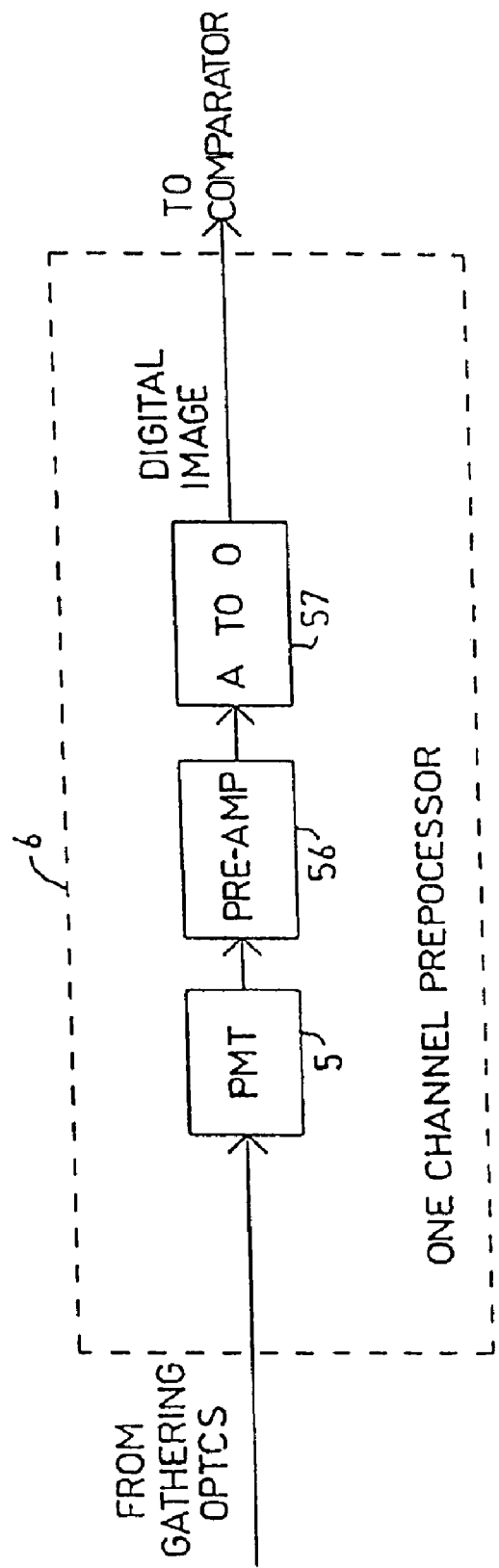
FIG. 13 is a block diagram illustrating the main components of the preprocessor in one channel of the processing system of FIG. 12.

As shown in FIG. 13, the preprocessor 6 in each channel includes a preamplifier 56 which converts the current received from its respective sensor 46 into a voltage and amplifies it to a level suitable as an input to an A/D converter 57. The parameters of amplification can be controlled in accordance with the characteristics of the signal received from the inspected wafer. The A/D convector 57 samples the analog voltage and converts it to a digital value. Sampling of the image is carried out continuously to obtain a two-dimensional image of the object.

Two flows of eight streams of data are thus generated: One flow represents the pixels of eight different images of the reference pattern previously stored in a temporary memory; and the other flow represents the pixels of different images of the inspected pattern to be compared with those of the reference pattern in order to provide an indication of the presence of a defect in the inspected pattern. The detection of defects is made in a Defect Detector circuit 60a–60h for each of the eight streams.

The processing system illustrated in FIG. 12 further includes an Alignment Control Circuit 62 which controls a Registrar Circuit 64a–64h for each second Defect Detector circuit 60a–60h. Thus, the Registrator Circuits 64a, 64c, 64e and 64g continuously monitor the registration between the reference and inspected images. They produce a score matrix for each of the chosen registration points, and output a score matrix (i.e., a matrix of values) for each of the possible shift positions around the current registration point. The Alignment Control Circuit 62 analyzes the score matrices obtained from four of the sensor channels (i.e., every other one). It computes the value of alignment error signals ($D_x$, $D_y$) where the best match occurs, and outputs the alignment control signals to the Defect Detector circuits 60a–60h to correct misalignment between the two flows of data streams.

The Defect Detector circuits 60a–60h feed their outputs to a Decision Table 66 which makes a decision, based on the alarm values obtained from all eight sensor channels, as to whether a Global Defect Alarm (i.e., a logical output indicating the existence of a defect at a given location) should be issued or not. The Decision Table 66 thus receives, as inputs, the alarm values from all eight channels, and outputs a Defect flag.

Each of the eight alarm values has one of three values (0, 1 or 2) indicating no alarm, low alarm, and high alarm, respectively. The decision table is set to output a defect flag "1", indicating the existence of a defect if, and only if: (a) at least one alarm value is "2"; and (b) at least two adjacent alarm values are "2" or "1" (alarm values of channels "a" and "g" are adjacent).

The output of Decision Table 66 is applied to a parameters buffer circuit 68 which records the parameters describing each defect, such as the exact coordinates and the type (to be explained later) and intensity of the pixels in the immediate vicinity of the defect in both the inspected and reference images. It receives as inputs the alarm flag trigger ("O" indicates no defect, and "1" indicates a defect), and all the parameters to be recorded. The latter are received from temporary memories associated with each of the eight channels. The parameters buffer 68 outputs a list of the defects accompanied by their parameters to the post processor 14.

The post processor 14 receives the list of suspected defects, together with their relevant parameters, and makes decisions before passing them on to the main controller for processing by the Phase II image processor system. It outputs a list of suspected points to transmit to the Phase II examination system, including their parameters, and also a list of defects which will not be transmitted to the Phase II examination system.

Figure 14:
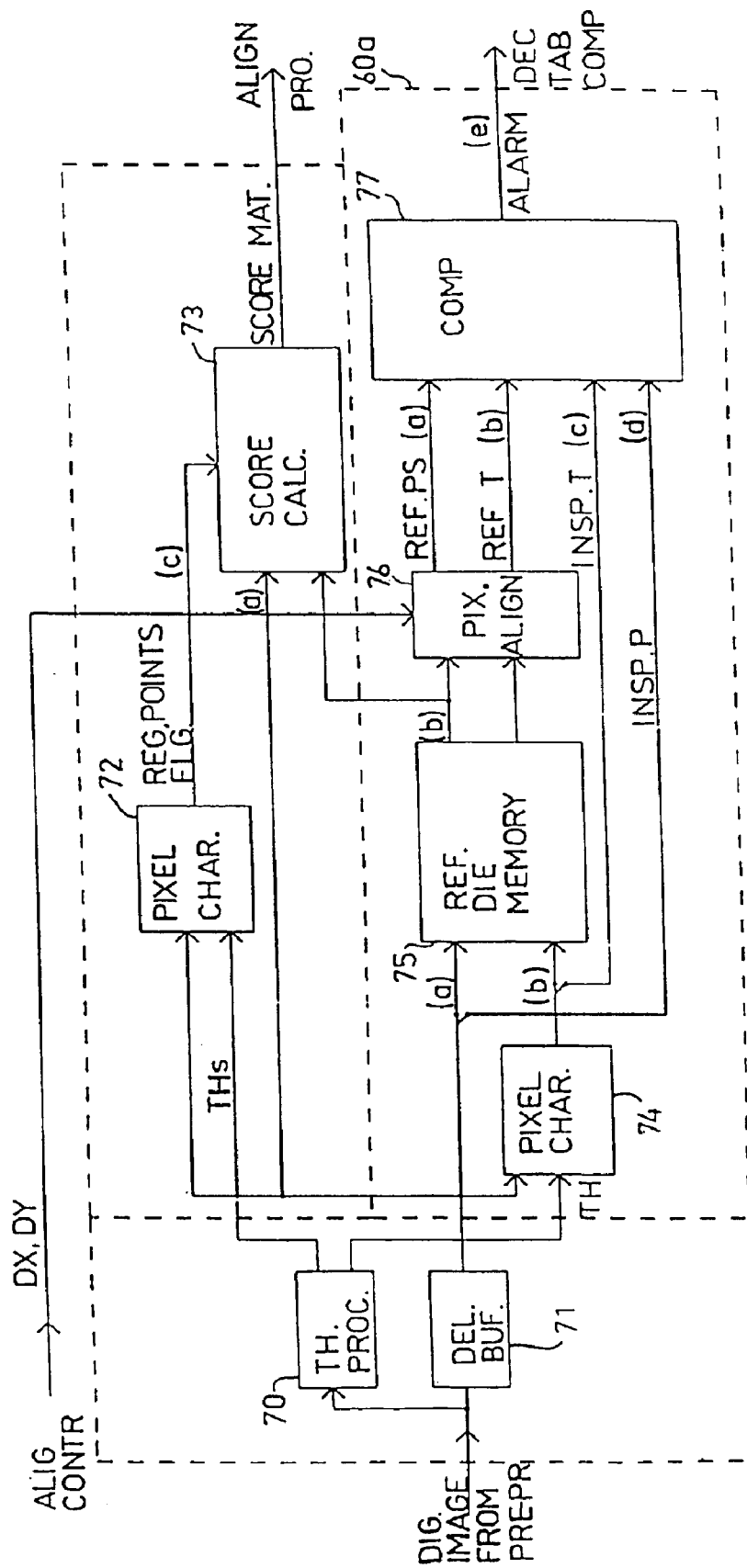
FIG. 14 is a block diagram illustrating one channel in the processing system of FIG. 12 following the preprocessor, FIG. 14a illustrating the algorithm involved in one of the operations performed by that system.

FIG. 14 more particularly illustrates the Defect Detector (e.g., 60a) and its associated Registrator (64a) in one channel of the image processor of FIG. 12.

Detection of defects by the defect detector in each channel is based on the comparison of each pixel in the inspected stream with the corresponding pixel in the corresponding reference stream. Pixels are compared relative to an adaptive threshold determining detection sensitivity according to pixel type. The type of each pixel is determined by pixel characteristics, such as signal intensity and shape in a 3×3 neighbourhood.

Thus, the digital image from the preprocessor (6a–6h) in the respective stream is fed to a Threshold Processor 70, and also to a Delay Buffer 71. The outputs from the Threshold Processor 70 and the Delay Buffer 71 are applied to Pixel Characterizers 72 and 74. Pixel Characterizer 72 is in the Registrator Circuit 64a (FIG. 12) which circuit outputs signals to a Score Calculator 73 (FIG. 14) controlling (with three other streams as indicated above) the Alignment control circuit 62 (FIG. 12). Pixel Characterizer 74 is used for comparison. It is connected to a Reference Die Memory 75 which also receives the signals from the delay buffer 71 and outputs signals to the Score Calculator 73 and also to a Pixel Aligner 76, the latter outputting signals to a Comparator 77.

Comparator 77, which is included in the Defect Detector 60 for each channel, carries out a comparison between the inspected image in the vicinity of the current pixel, and the reference image in the vicinity of the corresponding pixel. The comparison is made with respect to a threshold level which is dependent on the pixel type of the current pixels in the reference image and inspected image.

Thus, Comparator 17 includes four inputs: (1) reference pixels input (a), corresponding to the intensity of the pixels in the reference image; (2) reference type input (b), corresponding to the type of pixel in the reference image; (3) inspected type input (c), corresponding to the type of the pixels in the inspected image; and (4) inspected pixels input (d), corresponding to the intensity of pixels in the inspected image. As a result of the comparison performed by Comparator 77, it outputs an alarm value, via its Alarm output (e), of three possible results of the comparison: (a) exceeds higher thresholds; (b) exceeds lower threshold only; and (c) below the threshold. As shown in FIG. 12, the outputs of Comparator 77 in all eight streams are fed to the Decision Table 66.

The Threshold Processor 70 computes the thresholds for classification of the pixels as they are scanned. The computation is based on histograms of the characteristic parameters. There are three thresholds for each parameter: (a) for decision on registration points; (b) for classification of pixels in the reference image; and (c) for classification of pixels in the inspected image.

Threshold Processor 70 receives the pixel stream from the scanned object via its preprocessor (e.g., 6a, FIG. 12), and outputs its threshold levels to the Pixel Characterizers 72 and 74, one for registration and one for the comparison.

Delay Buffer 71 delays the processing in the respective Defect Detector (e.g., 60a) and Registrator (e.g., 64a) until the thresholds have been computed. This ensures that the thresholds are set according to the parameters in the area which is being scanned. Thus, it receives the pixel stream, from the object being scanned via its respective preprocessor, and outputs the same to the two Pixel Characterizers 72, 74, and to the Reference Die Memory 75, after a suitable delay.

Pixel Characterizer 74 computes the type of the current pixel. Thus, during the scanning of the reference pattern it computes the type of each pixel in that image for storage in the Reference Die Memory 75; and during scanning of the inspected pattern, it continuously computes the type of the current pixel which is transmitted directly to Comparator 77.

Pixel Characterizer 72 selects registration points on the basis of the pixel type, determined from the results of the computation of pixel parameters and their comparison with thresholds. Thus, its inputs are the inspected image from the Delay Buffer 71, and the thresholds for all the pixel parameters from the Threshold Processor 70; and it outputs registration point flags to the Score Calculator 73 for points chosen as the registration points.

The Score Calculator 73 computes the score matrix of correlation between the inspected and reference images in all the possible shifts around the current pixel, up to the maximum allowed. It receives three inputs: (a) the inspected image, to define the area around which the correlation is checked; (b) the reference image, to define the range of possible matches within the maximum range of horizontal and vertical shifts; and (c) a control input, from Pixel Characterizer 72, allowing the choice of registration points on the basis of pixel type.

The outputs of four (of the eight) streams are fed to the Alignment Control Circuits 62 (FIG. 12) in order to calculate the proper registration.

Pixel Characterizer 74 computes the type of the current pixel. Thus, during the scanning of the reference pattern, it computes the type of each pixel in that image for storage in the Reference Die Memory 75; and during the scanning of the inspected pattern it continuously computes the type of the current pixel, which is transmitted directly to the Comparator 77.

Pixel Characterizer 74 includes two inputs: (a) the digital image, outputted from the Delay Buffer 71; and (b) the threshold values from the Threshold Processor 70 for the relevant parameters, to enable a decision to be made as to the pixel type. Pixel Characterizer 74 is described more particularly below with respect to FIG. 17.

The Reference Die Memory 75 stores an image of the reference pattern. This image contains both the intensities of the pixels and their classification type. It includes a Pixels input (a), receiving the gray level for each pixel from the Delay Buffer 71, and a Type input (b), receiving the pixel classification from the Pixel Characterizer 74. The inputs are active only when the reference pattern is being scanned, and the reference image is retrieved when needed for the purpose of comparison with the inspected image. It includes a Pixels output (b) applied to the Score Calculator 73 and also to the Pixel Aligner 76, and a Type output applied to the Pixel Aligner 76.

The Pixel Aligner 76 executes an advance or a delay in the pixels being outputted by the Reference Die Memory 75 before they reach the comparison stage, in order to align them with the current pixel in the inspected image. Its inputs are the pixels intensity and type outputs from the Reference Die Memory 75, and also an alignment control input from the Alignment Computer 62 (FIG. 12); and it outputs the reference image pixel streams with an advance or delay.

Comparator 77 carries out a comparison between the inspected image in the vicinity of the current pixel, and the reference image in the vicinity of the corresponding pixel. This comparison is made with respect to a variable threshold level, which is dependent on the pixel type of the current pixel in the reference and inspected images. Thus, its inputs (a)–(d) include the pixels intensity and type in the reference image from the Pixel Aligner 76, and the pixel intensity and type in the inspected image from the Delay Buffer 71 and Pixel Characterizer 74, respectively.

Figure 15:
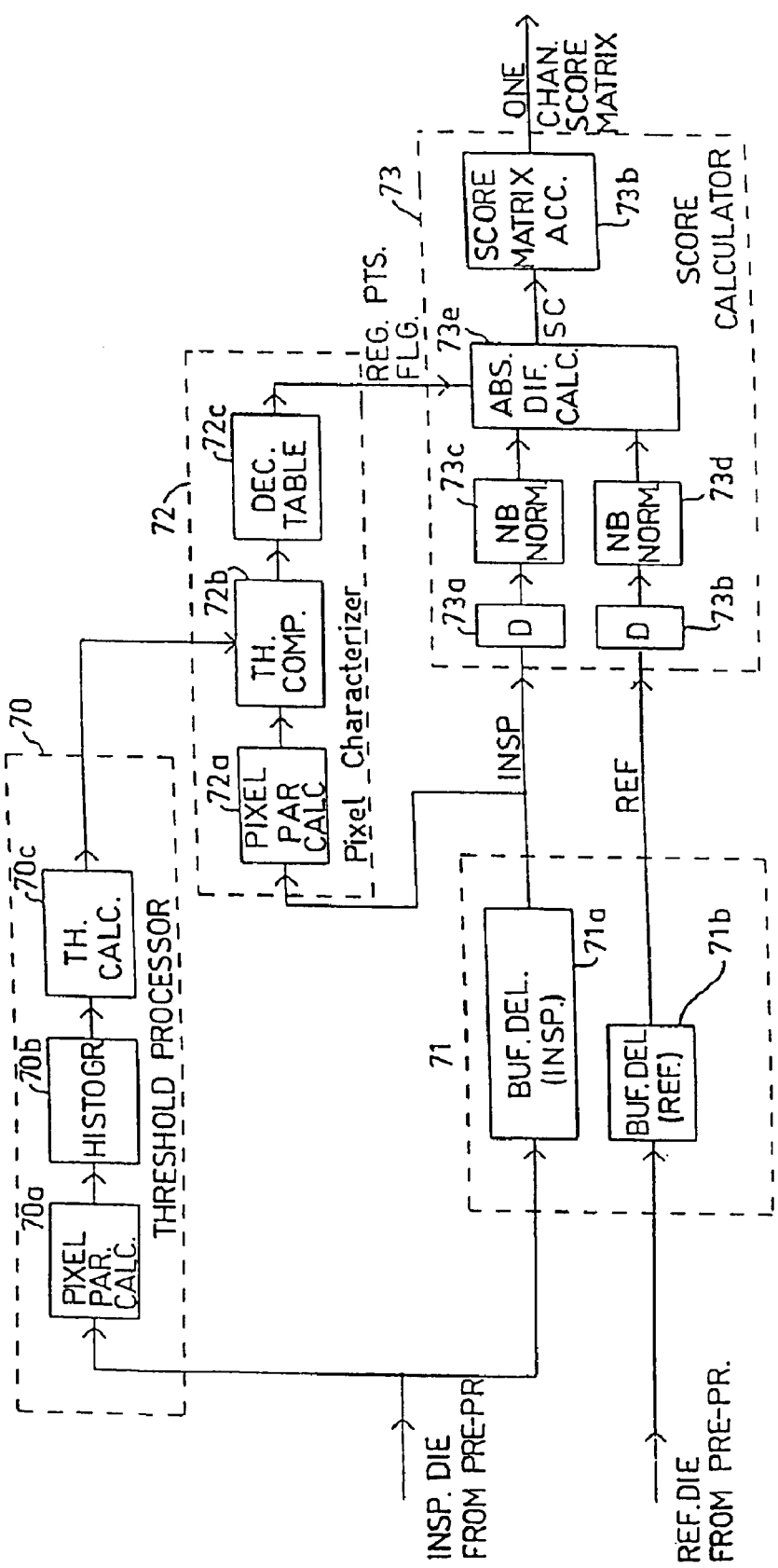
FIG. 15 is a block diagram particularly illustrating a portion of the processing system of FIG. 14.

FIG. 15 more particularly illustrates the Registrator (e.g., 64a) of FIG. 14, especially the Threshold Processor 70, Delay Buffer 71, Pixel Characterizer 72 and Score Calculator 73.

As described earlier, the Threshold Processor 70 computes the thresholds for classification of the pixels as they are scanned, the computation being based on histograms of the characteristic parameters. The Threshold Processor thus includes a Pixel Parameters Calculator 70a, which calculates the parameters of the current pixel on the basis of its immediate surroundings; a Histogrammer 70b which computes the histogram of the current pixels parameters; and a Threshold Calculator 70c which examines the histogram for each parameter and determines from it the proper value of threshold for that parameter.

The Delay Buffer 71 corrects the timing of the arrival of the reference and inspected images to that of the arrival of the registration point flags from the Pixel Characterizer 72.

Thus, Delay Buffer 71 includes a buffer 71a for the inspected image, and a buffer 71b for the reference image.

The Pixel Characterizer 72, as described with reference to FIG. 14, chooses the registration point on the basis of the pixel type. It includes the following subunits: a Pixel Parameters Calculator 72a, which calculates the parameters (gradient, ratio, maximum) of the current pixel on the basis of its immediate surroundings; Threshold Comparators 72b which compare these parameters with the thresholds which have been set separately for each parameter by the Threshold Processor 70; and a Decision Type Table 72c, which determines, on the basis of the results of the comparison by the Threshold Comparators 72b, whether the current pixel is suitable at the sampling point to carry out registration.

Figure 14A:
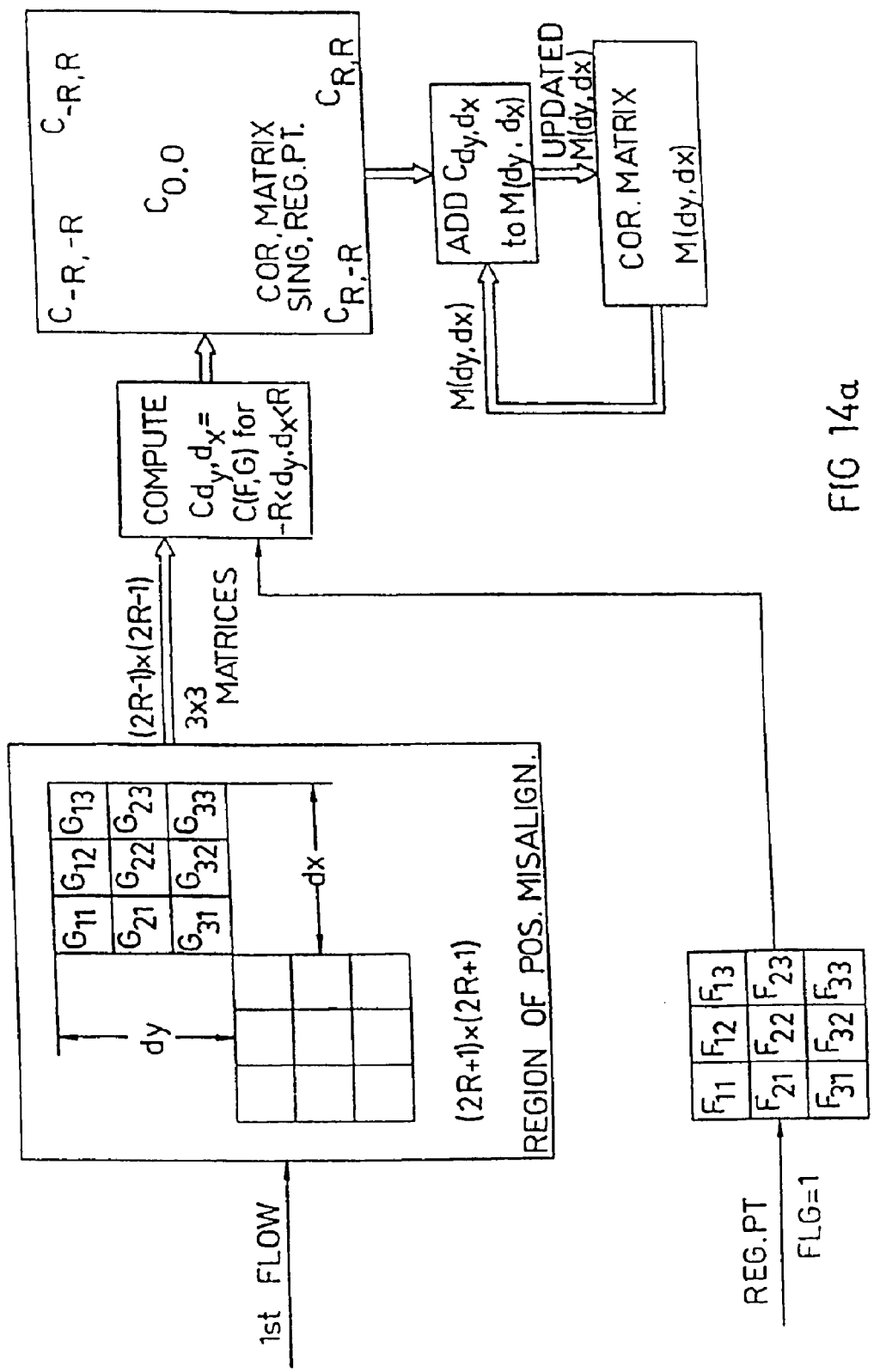

For every registration point the correspondence of its 3×3 pixels neighbourhood is measured against pixels in a range of ±A in the corresponding stream. FIG. 14a illustrates the algorithm. For each of the (2R←1)×(2R←1) possible misalignments, a correlation measure is computed as the normalized sum of absolute difference. The correlation matrices computed for different registration points are summed, and the minimal value in the matrix corresponds to the correct misalignment.

The Score Calculator 73, as described earlier with reference to FIG. 14, computes the score matrix of correlation between the inspected and reference images in all the possible shifts around the current pixel, up to the maximum allowed plus or minus vertical and horizontal ranges). This unit includes the following circuits: delays 73a, 73b, to correct the timing of the arrival of the inspected and reference images, respectively, to that of the arrival of the Registration Point flags from the pixel characterizer 72; Neighbourhood Normalizers 73c, 73d, to normalize the pixels in the neighbourhood of the current pixel; Absolute Difference Calculator 73e, which finds the absolute difference between the inspected image in the vicinity of the current pixel as against all the possible matches in the reference image within the maximum range of shifts in the vertical and horizontal axes, and computes the score matrix for these matches; and Score Matrix accumulator 73f which sums and stores all the score matrices which are accumulated during the scanning of a number of successive rows, before transmitting them to the Alignment Computer 62 (FIG. 12) for computation of the best match.

The Neighbourhood Normalizers 73c, 73d, normalizer the pixels in the neighbourhood of the current pixel in accordance with the following formula:

$$Pnew = P(ij) = N(ij) \text{ where } nij = \frac{\sum_{n=-1}^{1}\sum_{n=-1}^{1} P(i+n, j+n)}{9}$$

Figure 16:
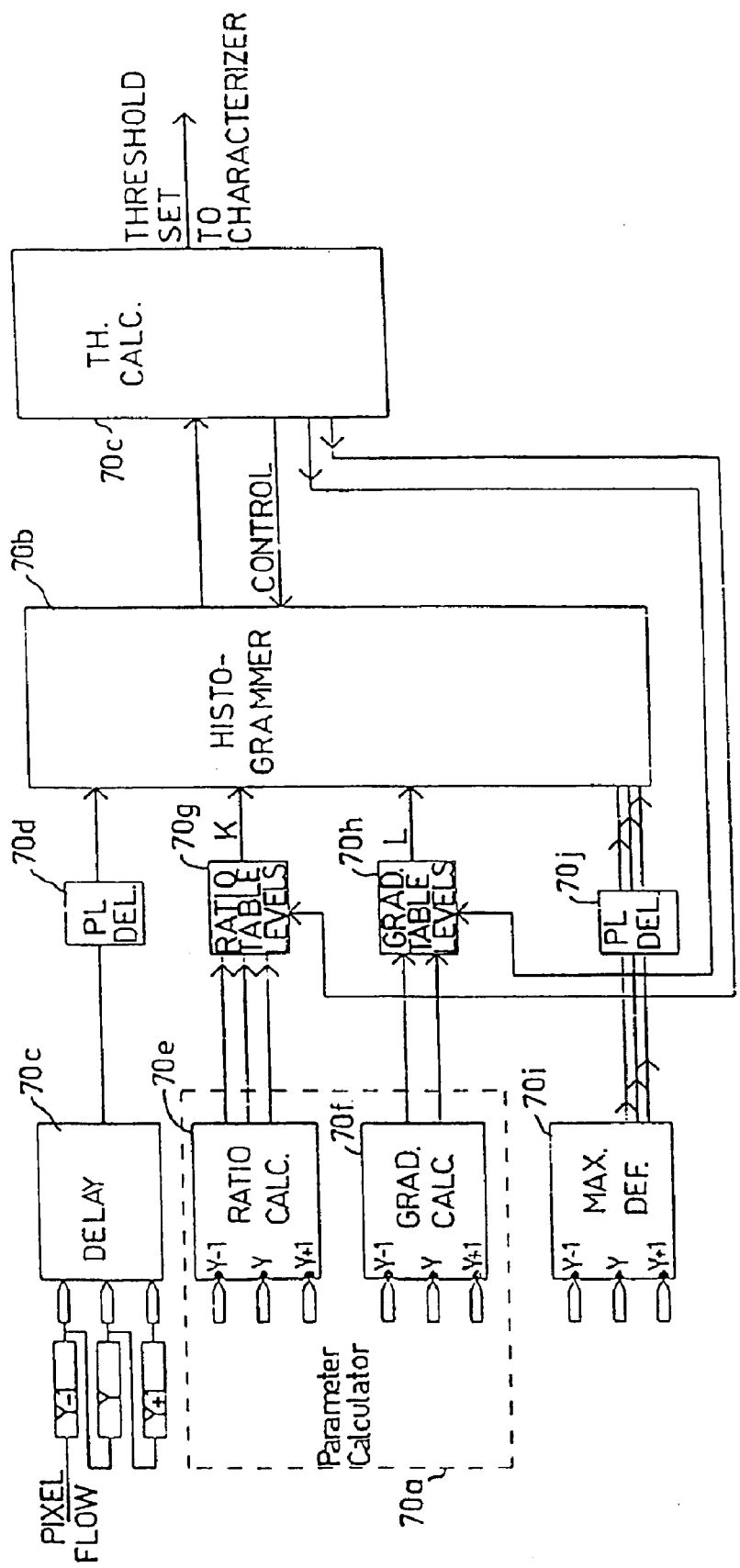
FIG. 16 is a block diagram particularly illustrating the Threshold Processor in the processing system of FIG. 12.

The Threshold Processor 70 of FIGS. 14 and 15 is more particularly illustrated in FIG. 16. As described earlier, it computes the thresholds for classification of the pixels as they are scanned, the computation being based on histograms of the characteristic parameters. It includes, in addition to the Parameters Calculator 70a, the Histogrammer 70b and the Threshold Calculator 70c described above with reference to FIG. 15, also a delay line 70c, which delays the pixels received at the input to the pixel flow circuit until a column of three pixels from three adjacent rows are received. These pixels are delayed in a pipeline delay subunit 70d before being applied to the Histogrammer 70b.

The Parameters Calculator 70a includes a Ratio Calculator 70e, and a Gradient Calculator 70f.

The Ratio Calculator 70e computes the ratio between the current pixel P(ij), and the average of the pixels in the surrounding area in the vertical and horizontal directions. It outputs the following signals: the ratio in the horizontal direction (Rh); the ratio in the vertical direction (Rv); and the ratio to the average of the four surrounding pixels (Rij).

The Gradient Calculator 70f calculates the gradient in the surroundings of the current pixel P(ij) in a matrix of 3×3 adjacent pixels by operation of a convolvor with the following coefficients:

In the VERTICAL DIRECTION:

$$\begin{bmatrix} -1 & 0 & 1 \\ -1.4 & 0 & 1.4 \\ -1 & 0 & 1 \end{bmatrix}$$

In the HORIZONTAL direction:

$$\begin{bmatrix} 1 & 1.4 & 1 \\ 0 & 0 & 0 \\ -1 & -1.4 & -1 \end{bmatrix}$$

The outputs of the Ratio Calculator 70e are applied to a Ratio Table of Levels 70g, before being fed to the Histogrammer 70b, and the outputs of the Gradient Calculator 70f are applied to a Gradient Table of Levels 70h before being fed to the Histogrammer 70b.

The Threshold Processor illustrated in FIG. 16 further includes a Maximum Definition circuit 70i, which makes a decision on the current pixel in relation to its surroundings, to define the following parameters: M(ij)=1, if the pixel is larger (higher in intensity) than all the eight surrounding pixels; M(v)=1, if the pixel is larger than its two neighbours in the same column; and M(h)=1, if the pixel is larger than its two neighbours in the same row.

The outputs of the Maximum Definition circuit 70i are applied, via a pipeline delay circuit 70j, to the Histogrammer 70b.

The Ratio Table of Levels 70g divides the ratio results into K groups in order to build the histogram. The K groups are obtained by comparison with a vector of K threshold level Cr(K), which indicates a different area of the table for each threshold.

The Gradient Table of Levels 70h divides the gradient results into L groups for the purpose of building the histogram. The L groups are obtained by comparison with a vector of L threshold levels Cr(L), which indicate a different area of the table for each threshold.

Histogrammer 70b executes a histogram of the pixel intensities P(ij) in different cells of the memory in accordance with the following parameters: M(Maximum); L(Gradient); and K(Ratio).

The Threshold Calculator 70c in the Threshold Processor 70 illustrated in FIG. 16 is a microprocessor which receives the results of the Histogrammer, analyzes them, and computes the thresholds for a decision on the pixel type, for: Registration, Reference Image, and Inspected Image. It outputs the results to the Pixel Type Characterizer 72 and 74, as described above with reference to FIG. 14.

Thus, the Pixel Type Characterizer 74 includes five Comparators $74b_1$–$74b_5$ which compare the various parameters (Ratio, Gradient and Maximum) which have been previously computed in units $74a_1$, $74a_2$, $74a_3$, with the threshold levels coming from the Threshold Processor 70. Thus, Comparator $74b_1$ compares the pixel flow with the Intensity threshold I from the Threshold Processor 70; Comparators $74b_2$, $74b_3$ compare the outputs of the Ratio Calculator $74a_1$ with the Ratio thresholds R and Rhv, respectively from the Threshold Processor; and Comparators $74b_4$, $74b_5$ compare the outputs of the Gradient Calculator $74e_2$ with the Gradient thresholds G and Ghv of the Threshold Processor 70.

The results of these comparisons are fed to the Decision Table 74c, which also receives the output parameters from the Maximum Definition Unit $74a_3$ M(ij) to decide on the pixel type.

The output of the Decision Table 74c is a two-bit word indicating the pixel type. The output is applied to a Type Updating unit 74d, which modifies the results of the Pixel type in certain exceptional cases, such as a pixel slope next to a pixel peak (i.e., to distinguish between an "isolated peak" and a "multipeak").

A pixel is assigned a type according to the following four parameters computed for its 3×3 pixels neighbourhood: (1) local maxima indicator, (2) intensity, (3) ratio, and (4) gradient. FIG. 17a illustrates the algorithm to determine the pixel type from these parameters, computed as follows:

1. Local maxima—indicates if a pixel is a maximum relative to its neighbours.

$$m(F_{2,2})=1 \text{ if } F_{2,2} \geq F_{i,j} \text{ for all } 1 \leq i \leq 3, 1 \leq j \leq 3$$

2. Intensity—indicates if the intensity of the pixel is significant relative to a threshold defined dynamically in a window of n×m pixels.

$$I(F_{2,2})=1 \text{ if } F_{2,2} \geq T_1$$

3. Ratio—indicates if the intensity of the pixel is significant with respect to its neighbours relative to a threshold defined dynamically in a window of n×m pixels.

$$r(F_{2,2}) = 1 \text{ if } \frac{4 \times F_{2,2}}{F_{1,2} + F_{2,1} + F_{2,3} + F_{3,2}} \geq T_r$$

4. Gradient—indicates if the pixel is located in a slope area of 3×3 pixels relative to a threshold defined dynamically in a window of n×m pixels.

$$g(F_{2,2}) = \begin{array}{l} 1 \text{ if max } F \otimes 0i \geq T_6 \\ i = 1, 2 \quad i = 1, 2 \end{array}$$

where $0_1$ are gradient operators and x is convolution.

$$0_1 = \begin{vmatrix} 1 & 1.4 & 1 \\ 0 & 0 & 0 \\ -1 & -1.4 & -1 \end{vmatrix}$$

$$0_2 = \begin{vmatrix} 1 & 0 & -1 \\ 1.4 & 0 & -1.4 \\ 1 & 0 & -1 \end{vmatrix}$$

The type assigned to a pixel may be one of the following: isolated peak, multipeak, slope and background. The type is assigned according to the pixel's parameters as follows:

1. Isolated peak—if the pixel is a local maxima with significant intensity and ratio.

$$t(F_{2,2})=1 \text{ if } m(F_{2,2})=1 \text{ and } I(F_{2,2})=1 \text{ and } r(F_{2,2})=1$$

2. Multipeak—if the pixel is not an isolated peak, it has significant intensity and none of its neighbours is an isolated peak.

$$t(F_{2,2})=2 \text{ if } I(F_{2,2})=1 \text{ and } t(F_{1,j})=1 \text{ } 1 \leq i \leq 3, 1 \leq j \leq 3$$

3. Slope—if either one of the pixel's neighbours is an isolated peak or it has significant gradient.

$$t(F_{2,2})=3 \text{ if } t(F_{i,j})=1 \text{ for some } 1 \leq i, j \leq 3 \text{ except } F_{2,2}$$

or $$g(F_{2,2})=1$$

4. Background—if the pixel has no significant intensity, or gradient and none of its neighbours is an isolated peak.

$$t(F_{2,2})=4 \text{ if } I(F_{2,2})=1 \text{ and } G(F_{2,2})=1 \text{ and } t(F_{i,j})=1, 1 \leq i \leq 3, 1 \leq j \leq 3$$

The foregoing are implemented by the Ratio Calculator $74a_1$ illustrated in FIG. 18, by the Gradient Calculator $74a_2$ illustrated in FIG. 19, and by the Maximum Definition Calculator $74a_3$ illustrated in FIG. 20.

Thus, the Ratio Calculator $74a_1$ makes a decision about the central pixel in the matrix, and computes the ratio of the pixel intensity to its immediate neighbourhood.

The possible decisions about the central pixel in the matrix are as follows: (a) maximum, i.e., greater than any of its neighbours; (b) vertical maximum, i.e., greater than its vertical neighbours; and (c) horizontal maximum, i.e., greater than its horizontal neighbours.

The computation of the ratio of the pixel intensity to its immediate neighbourhood is: (a) in relation to the four immediate neighbours, if it is a maximum; and (b) in relation to the two relevant neighbours, if it is a vertical or horizontal maximum.

The Ratio Calculator includes nine registers, shown in FIG. 18a. Their functions are to record the nine values, designated by the letter A–I, of the pixels in a 3×3 matrix.

The Gradient Calculator $74a_2$ is more particularly illustrated in FIG. 19. Its function is to compute the values of Gradient of the matrix in the vertical and horizontal directions. The calculation is based on the following formulas:

$$2 \times Gh = ((A+B+C)^*2+B) - ((G+I+H)^*2+M)$$

$$2 \times Gv = ((A+G+D)^*2+D) - ((C+I+F)^*2+F)$$

such that the calculation represents multiplying the following matrices:

$$\text{Horizontal} \begin{bmatrix} 2 & 3 & 2 \\ 0 & 0 & 0 \\ -2 & -3 & -2 \end{bmatrix} * \frac{1}{2}$$

$$\text{Vertical} \begin{bmatrix} 2 & 3 & -2 \\ 3 & 0 & -3 \\ -2 & -3 & -2 \end{bmatrix}$$

The circuit calculates the values of the Gradient which includes the following components:

a) Register Matrix: A to I, in which the values of the pixels in the matrix are recorded.

b) Left Vertical: adds the pixels in the left column according to the formula:

$$(A+G+D)^*2+D$$

c) Right Vertical: adds the pixels in the right column according to the formula:

(C+I+F)*2+F d) Horizontal Up: adds the values of the pixels in the upper row, according to the formula:

(A+C+B)*2+B e) Horizontal Down: adds the values of the pixels in the lower row according to the formula:

(G+I+H)*2+H

Figure 17:
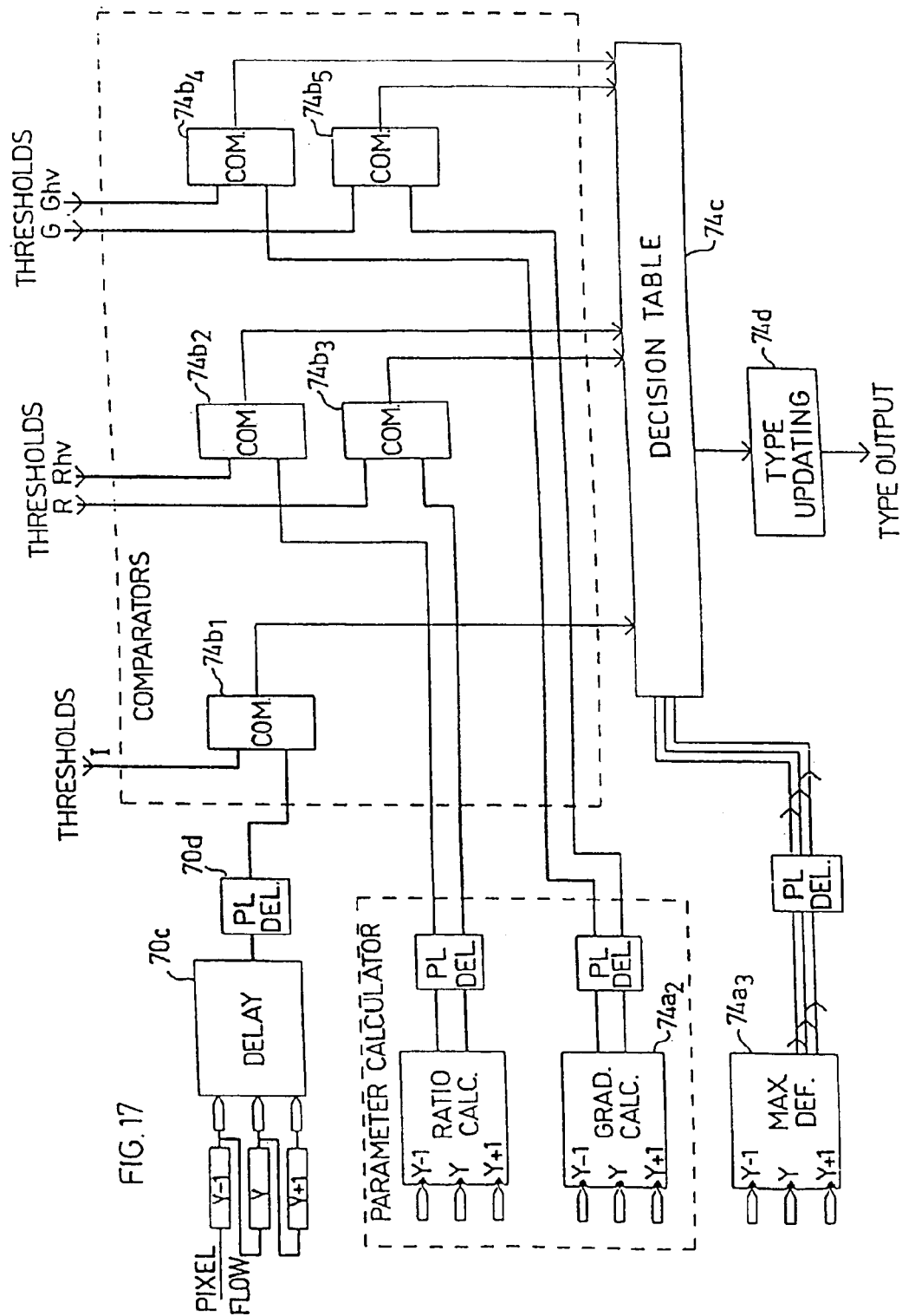
FIG. 17 is a block diagram more particularly illustrating the Pixel Characterizer of FIG. 15, FIG. 17a illustrating the algorithm involved.
Figure 17A:
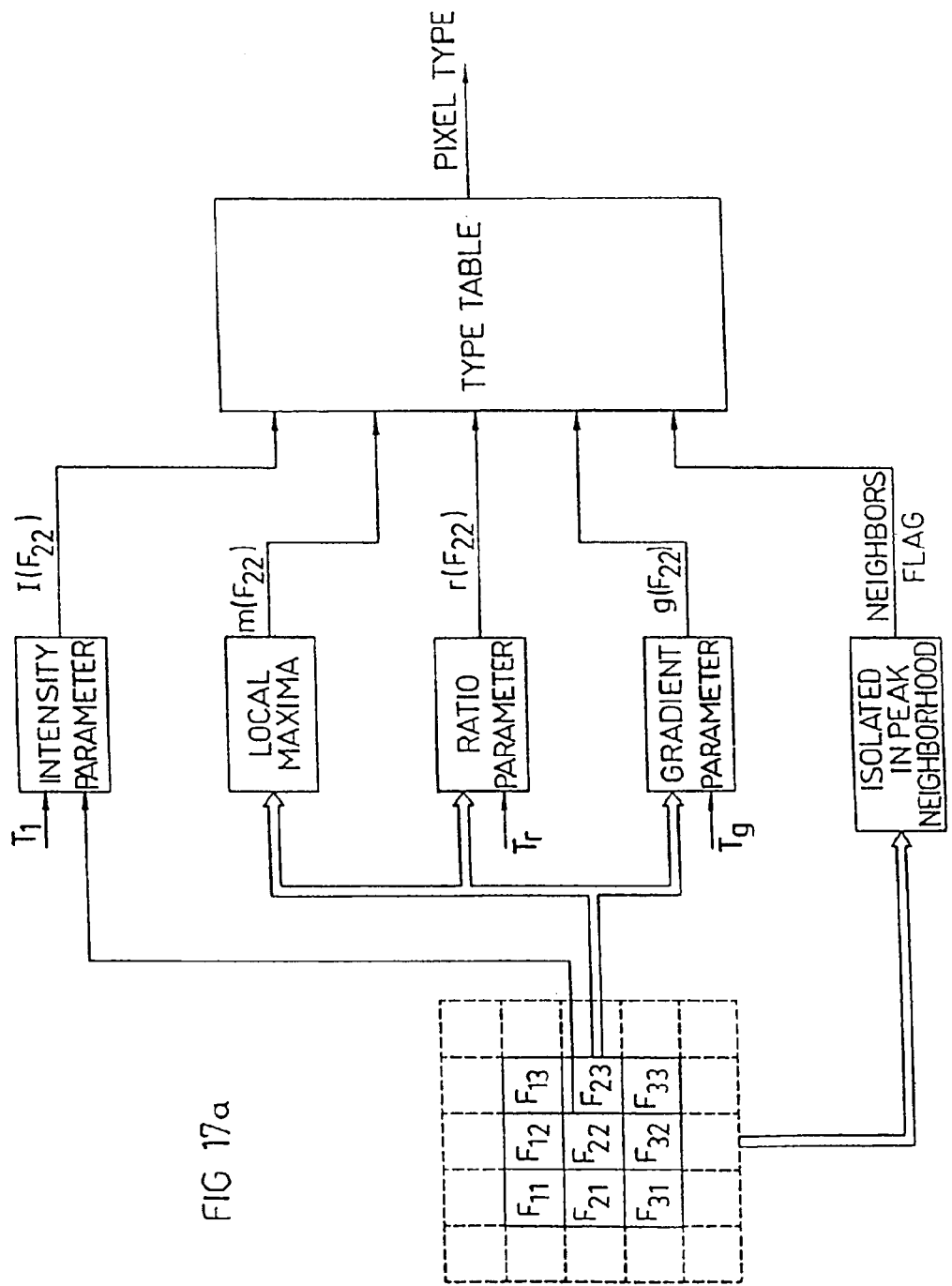

The Maximum Definition Calculator $74a_3$ in FIG. 17 is more particularly illustrated in FIG. 20. Its function is to compare, by means of comparators, the value of the central pixel E with those of its neighbours, to determine the following parameters:

a) Mv(i,j)—A logical signal which shows the condition that the central pixel E is greater than its vertical neighbours B and H.

b) Mh(i,j)—A logical signal which indicates that the central pixel E is larger than its horizontal neighbours D and F.

c) M(i,j)—A logical signal which indicates that the central pixel E is larger than all its neighbours A, B, C, D, F, G, H, I.

Figure 22:
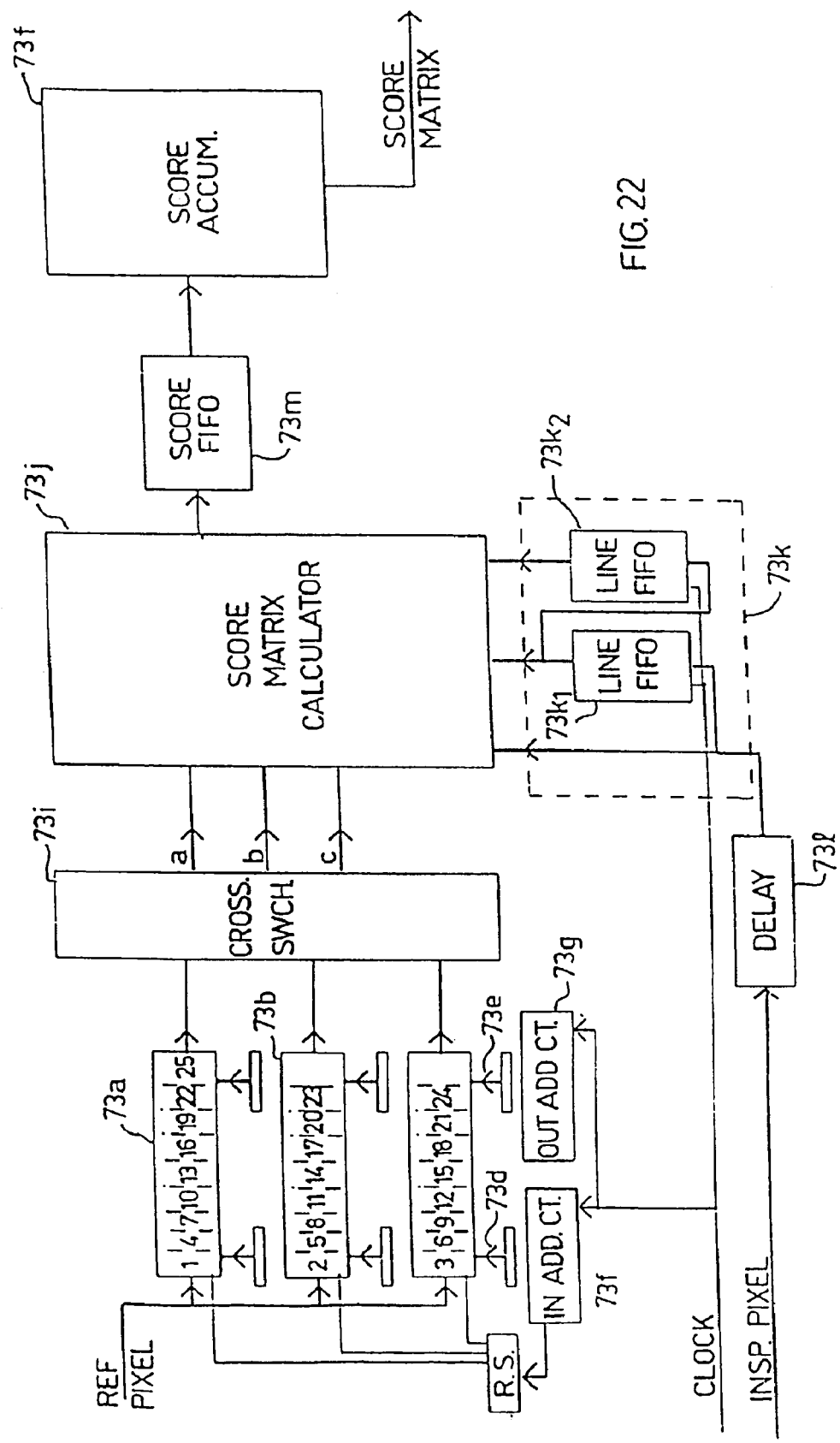
FIG. 22 illustrates the Score Calculator in the image processor channel of FIG. 14, FIG. 22a being diagrams helpful in understanding the operation of the crossbar switch (73i) of FIG. 22.

The ratio definition calculator computes the value of the Ratio parameter from the following two values:

a) Rij—The ratio of the central pixel to its surroundings.

$$Rij = \frac{X}{(B+H+D+F)/4}$$

b) Rvh—The ratio of the central pixel to the average of its vertical and horizontal neighbours.

if $Mv(i, j) = 1$ then $Rv = \frac{X}{(B+H)/2}$ if $Mh(i, j) = 1$ then $Rh = \frac{X}{(D+F)/2}$ The Registration Score Matrix Calculator 73 (FIG. 14) is more particularly illustrated in FIG. 22. This calculator includes a dual-port memory 73a–73c to temporarily store a window of up to 25 consecutive rows in the reference image, for the purpose of computing the score matrix of matches to a smaller window (up to three rows) in the inspected image. The memory has two channels of access: channel 3d, to store the image by input of the stream of pixel data continuously; and channel 73e, to output a window containing a strip of three rows wide, as required.

An input Address Counter 73f generates the pointer for the address at which the current pixel is stored; and an output Address Counter 73g generates the pointer for the address from which is outputted the window on which registration is kept out. The input Address Counter 73f selects the memory via a memory selector 73h. The storage of a window from the reference image is carried out in such a manner that each new row is inputted to a different one of the three memories 73a–73c, so that the first memory contains rows 1, 4, 7, etc.; the second memory 73b contains rows 2, 5, 8, 11, etc.; and a third memory 73c contains rows 3, 6, 9, 12, etc.

Figure 22A:
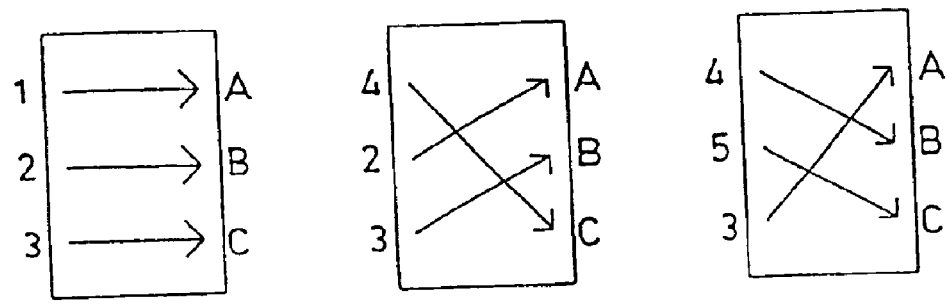

The Registration Score Matrix Calculator 73 illustrated in FIG. 22 further includes a crossbar switch 73i. Its function is to transmit three consecutive rows, and to allow switching of these rows each time that a computation of a full row of the score matrix is completed, there is a need to move to the next row. As an example, initially rows 1, 2, 3 are passed to outputs A, B. C; next. rows 2, 3 and 4 are passed to outputs A, B, C, respectively; and so on. The combinations are shown in the diagrams illustrated in FIG. 22a.

The Registration Score Matrix Calculator 73 illustrated in FIG. 22 further includes a converter 73k which converts the stream of current pixels to three pixels in parallel from three consecutive rows. The conversion is carried out by means of two FIFO (first-in, first-out) delay lines $73k_1$, $73k_2$, connected in series and each having a length of one complete row.

Calculator 73 further includes a delay 731 for the purpose of synchronizing the appearance of the current pixel in the inspected image with the corresponding pixel in the output of the reference image, before inputted into the score matrix calculator for storage of the respective window.

The Score Matrix Calculator 73j computes the score matrix between the inspected and reference images for all possible shifts of the window. This method of computation is described more particularly below with respect to FIG. 23.

The Score Matrix Calculator 73j receives three pixels from three consecutive rows, from which are produced the nine pixels which form the inspection image. The nine pixels are frozen while the score matrix is being computed. Calculator 73j also receives three pixels from three consecutive rows from which are produced the nine pixels which form the reference image. The nine pixels change with each clock pulse, until all possible combinations of the 3×3 matrix within the search window have been completed.

The result of the normalized difference between the inspected image and the reference image is outputted every clock pulse, until all possible combinations of the 3×3 adjacent pixels within the search window are completed.

The Score Calculator 73 further includes a Score FIFO Memory 73a. Its function is to regulate the timing of the transfer of the normalized results, which represent the score matrix, from the Registration Score Calculator 73j to the Score Accumulator 73f.

The Score Accumulator 73f sums the score matrix which has been calculated for one registration point, to that for a second registration point. It thus assembles a sample of registration points until the final matrix is passed to the Alignment Computer 62 (FIG. 12) to compute the Dx and Dy alignment control signals.

Figure 23:
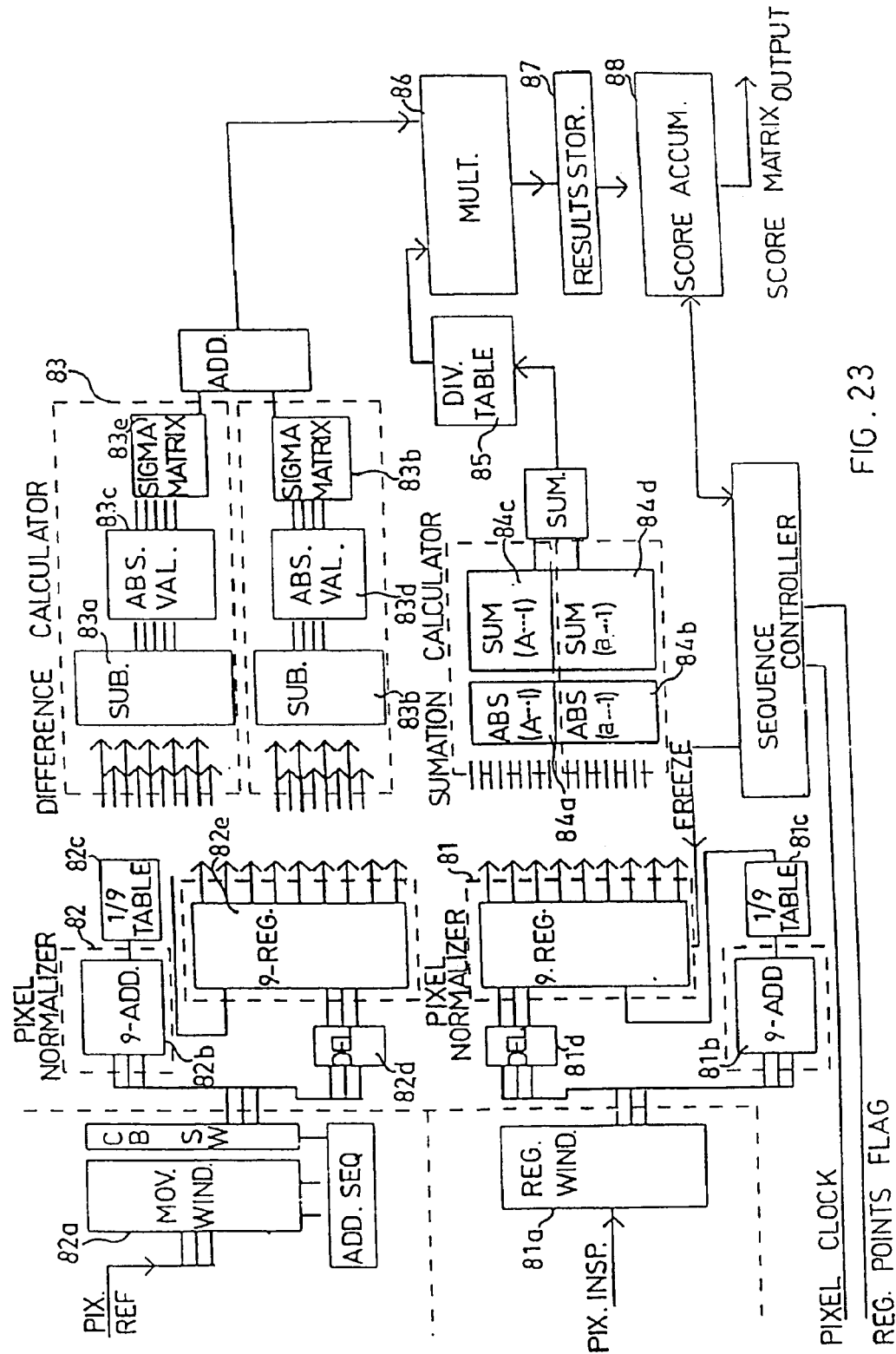
FIG. 23 is a block diagram helpful in understanding the operation of the score calculator of FIG. 22.

The Registration Score Matrix Calculator 73j illustrated in FIG. 22 is more particularly shown in FIG. 23. It computes the score matrix based on the normalized difference between the inspected image (3×3 pixels in extent), and all the N×N possible matches in the corresponding matrix in the reference image.

Calculator 73j includes a Pixel Normalizer 81 (FIG. 23) for the inspected image; a Pixel Normalizer 82 for the reference image; a Difference Calculator 83; a Summation Calculator 84; a Division Table 85; a Multiplier 86; a Results Storage device 87; and a Score Accumulator 88.

Pixel Normalizer 81 for the inspected image includes a registrator window 81a whose function is to convert the format of the inspected image from a serial stream of pixels to a format of a sequence of columns of pixels from three consecutive rows; it thus enables, by the use of three shift registers of length of three pixels each, immediate access to a matrix of 3×3 pixels.

Pixel normalizer 81 further includes a nine-addition circuit 81b, which sums the intensities of the 3×3 pixel matrix around the current pixel. It further includes a ⅑ table 81c which divides the sum of the pixel intensities in the matrix by "9", and thereby obtains the average value of the pixels in the matrix.

A delay 81d delays the image data stream until the results of the average intensity from table 81c are available. The output of table 81c is applied directly, and via delay 81d, to a group of nine registers 81e, which subtract the average value from each of the nine pixels in the matrix. The nine results, representing the normalized values of the pixels, are available simultaneously at outputs A–I of the Pixel Normalizer 81. These pixel values will be frozen, and will serve as the reference for comparison throughout the process of computing the score matrix in relation to the reference image.

The Pixel Normalizer 82 for the reference image includes a moving window 82a whose function is to produce three consecutive rows in the search area having a size of N×N times a 3×3 matrix in the reference image. The three consecutive rows will supply the pixels needed to produce all the possible 3×3 matrices in the search area. Three additional pixels are acquired once per clock pulse in order to enable a new 3×3 matrix to be produced.

Pixel Normalizer 82 further includes a Nine-Addition circuit 82b which sums the values of the matrix, and a ⅑ Table 82c which computes the average of the pixels in the matrix. The reference data stream from the moving window 82a is delayed by a delay circuit 82d until the results of the average intensity from table 82c is available, so that both may be supplied simultaneously to the nine registers 82e. The nine registers 82e subtract the average value from each of the nine pixels in the matrix, so that the nine results representing the normalized values of the pixels are available simultaneously at outputs A–I.

Difference Calculator 83 computes the sum of the absolute differences of the 3×3 matrix of the inspected image versus the reference image. For this purpose, Calculator 83 includes, for each of the two Pixel Normalizers 81 and 82. a Subtraction Circuit 83a, 83b consisting of nine subtractors which compute the difference between each pixel in the inspected image versus the corresponding pixel in the reference image; an Absolute Value Circuit 83c, 83d, which computes the absolute value of the differences; and a Matrix Circuit 83e, 83f, which sums all the nine absolute values. The result of the absolute sum of the differences is passed to the Multiplier 86.

Multiplier 86 also receives the output from the Summation Calculator 84 via the Division Table 85. Thus, the Summation Calculator 84 computes the absolute sum of the two matrices On which the processing will be carried out. It includes, for each Pixel Normalizer 81, 82, an Absolute Value Circuit 84a, 84b, which computes the absolutes values of each normalized pixel; and a Matrix Sum Circuit 84c, 84d, which sums the nine absolute values.

Division Table 85 prepares the results of the summation for the operation of division by means of the Multiplier 86. Division Table 85 executes the arithmetic operation "1 divided by the sum", by converting the values using a PROM (Programmable Read Only Memory) table.

Multiplier 86 computes the result of the normalized difference for the point under test. The computation is carried out using the formula:

$$\text{SCORE} = (\Sigma |P_I - P_R|) * [/(1|P_I| - |P_R|)]$$

where $P_I$, $P_R$ are the normalized values of the pixels.

The Result Storage Device 87 temporarily stores the results of the score at a storage rate which is the same as that at which the results appear, and at an output rate matching the timing of acceptance of the results by the Score Accumulator 88. The Score Accumulator 88 sums the score matrix obtained at the current registration point with the score matrix obtained at the previous registration point. Summing of the matrices at the registration point is carried out for the defined sequence of windows, up to K consecutive rows, before the result of the Score Matrix is passed to the Alignment control circuits 62 (FIG. 12) for processing.

Figure 24:
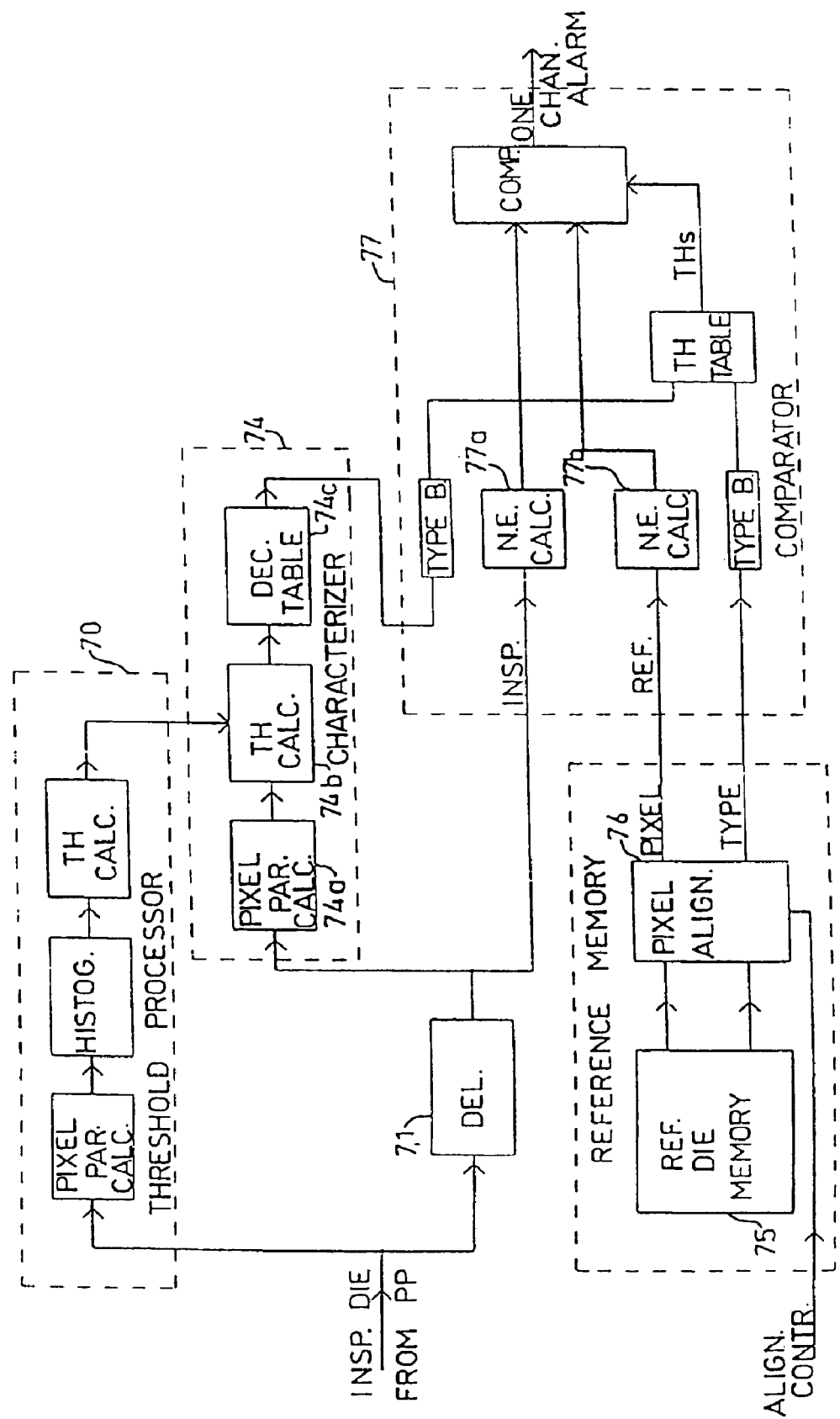
FIG. 24 is a block diagram illustrating more particularly the Defect Detector portion of the image processor of FIG. 14.
Figure 25:
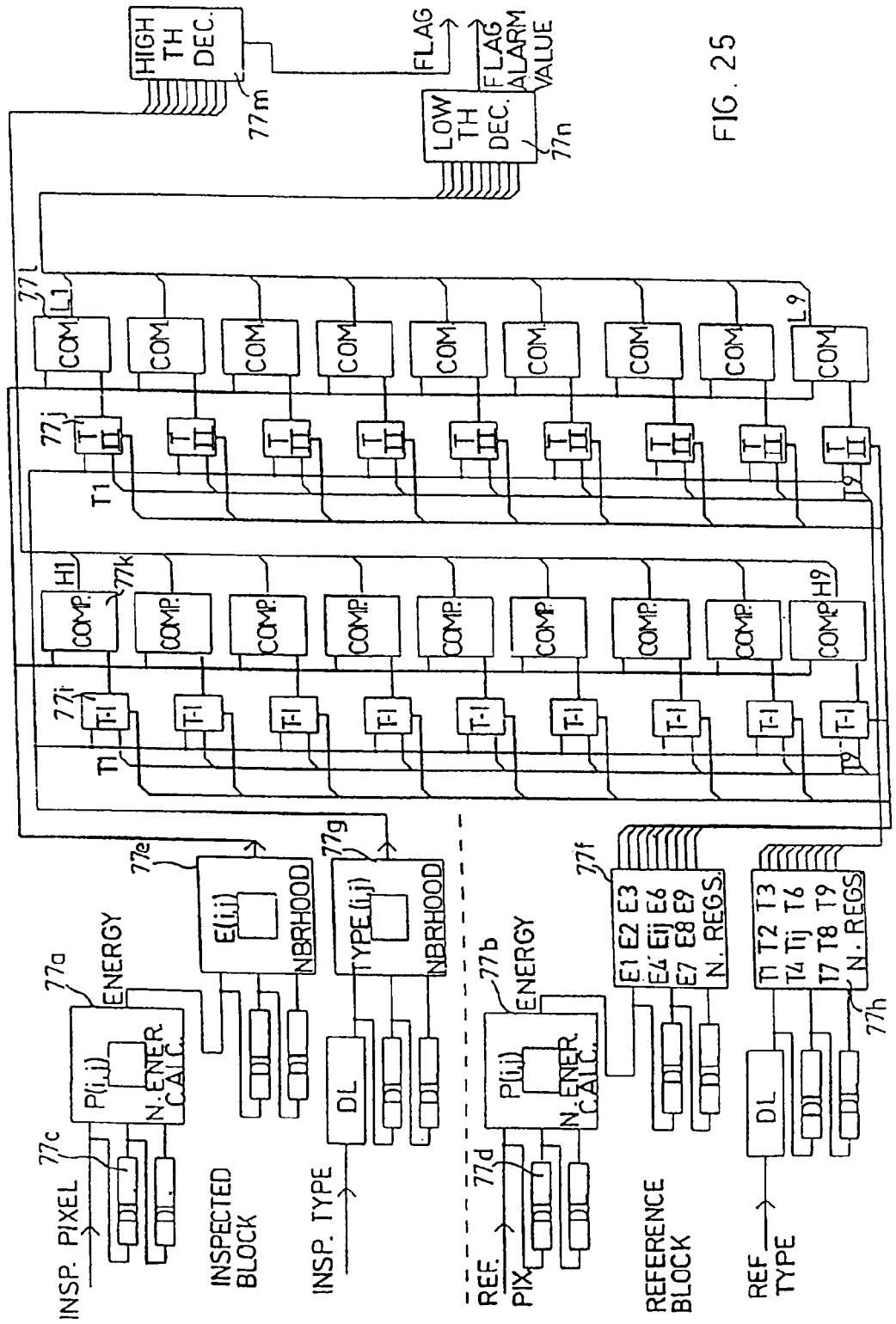
FIG. 25 is a block diagram illustrating more particulars of the comparator 77 of FIG. 24, FIG. 25a illustrating the algorithm involved.

The construction and operation of the Defect Detector, as illustrated for example in FIG. 14, will be bettor understood by reference to FIGS. 24 and 25. As describer earlier, the function of Comparator 77 is to carry out a comparison between the inspected image in the vicinity of the current pixel, and the reference image in the vicinity of the corresponding pixel, and to output an Alarm signal, via buffer 68 (FIG. 12), to the Post Processor 14 indicating whether or not there is a suspected defect. As also indicated earlier, the comparison is made with respect to a variable threshold level, which is dependent on the Type of the current pixel in the reference and inspected images.

Figure 25A:
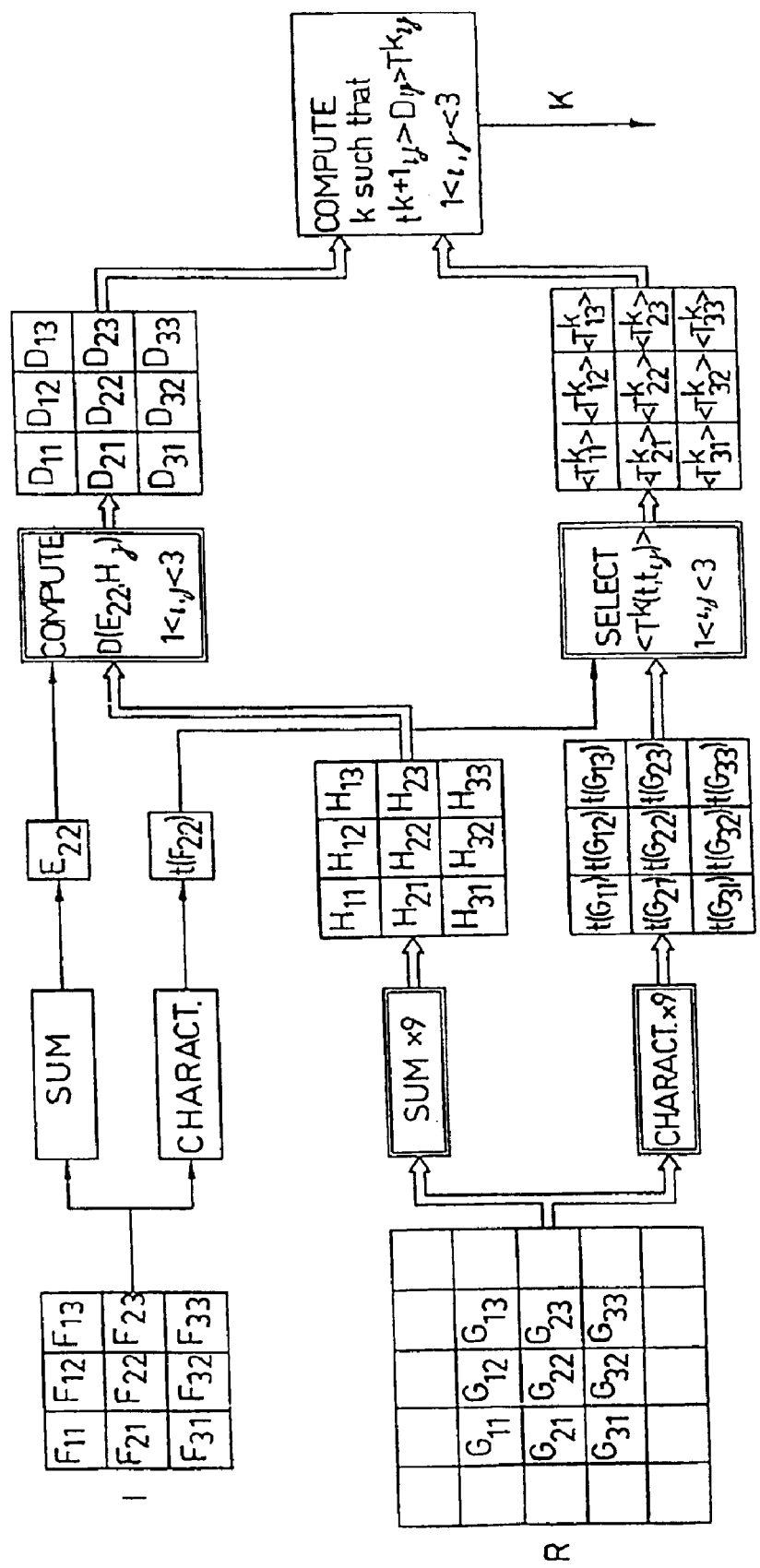

The comparison algorithm is illustrated in FIG. 25a. As shown therein, a pixel in a stream of the inspected image is compared against the corresponding pixel in the reference image. The comparison is done under the assumption that a local misalignment of plus or minus one pixel may exist. Accordingly, a pixel is compared to the nine pixels in the 3×3 neighbourhood centered at the corresponding reference pixel.

Each of the nine comparisons is made by comparing the difference between the energies of the compared pixels against a threshold determined by the pixel type. The energy of a pixel is the sum of the nine pixels in the 3×3 neighbourhood centered at the pixel. The alarm value is set to "2", if the difference in all nine comparisons is above the high threshold; to "1", if it is above the low threshold; and to "0" in all other cases.

Comparator 77 (FIG. 24) thus includes a neighbourhood Energy Calculator 77a, 77b for the inspected image and the reference image, respectively. Calculators 77a, 77b compute the energy of the surroundings of the current pixel in a 3×3 matrix of the near neighbours in the inspected image, and in the corresponding reference image. Delay lines 77c, 77d (FIG. 25) are provided before these calculators in order to produce suitable delays before and after the current pixel in order to obtain the three relevant rows for computation of the energy in the vicinity of the current pixel. The two calculators receive, as inputs, the relevant pixels in the three relevant rows surrounding the current pixel, and output the arithmetic sum of the nine pixels in the 3×3 matrix around the current pixel.

Comparator 77 further includes Neighbourhood Registers 77e, 77f for storing the energies in the two Calculators 77a, 77b, respectively, and further Neighbourhood Registers 77g, 77h. Their function is to prepare, in parallel form, the nine relevant Types (T1–T9) around the current pixel in the reference image, in order to determine the threshold level to be used in the execution of nine simultaneous comparisons. Thus, the Energy Neighbourhood Registers 77e, 77f, output nine energies E1–E9; while the Type Neighbourhood Registers 77g, 77h output nine types T1–T9 around the current pixel.

Comparator 77 further includes nine conversion tables 77i for the low threshold level, and nine conversion tables 77j for the higher threshold levels. These tables are loaded prior to the inspection session. The tables are selected from a set of tables according to the required sensitivity of the detection, as set by the user. Their function is to mutliply each one of the energies around the pixel being examined by a constant which depends both on the type of the examined pixel in the reference image, and the type of the current pixel in the inspected image.

Thus, tables 77i, 77j receive as inputs: (a) Type (ij), namely the type of the current pixel in the inspected image; (b) Type (1–9), namely the type of the pixel examined around the current pixel in the reference image; and (c) Energy E (1–9), namely the energy of the examined pixel in the reference image. The tables output signals EK(1–9), namely the multiplication results of the input energy E(1–9), by a constant which depends on the type of both the current pixel and the examined pixel. That is:

$$EK(1-9)=K(Tij,T)=E(1-9).$$

Each of the tables 77i, 77j, is connected to a Compare circuit 77k, 77l, whose purpose is to compare the current energy Eij and the multiplication results of the energy of the pixel and a constant, EK(1–9). The Compare circuit outputs logical indications of the result of the comparison, namely:

1 If EK(1–9) E(ij)

0 If EK(1–9)>E(ij).

A High Threshold Decision unit 77m tests whether all the comparison outputs exceeded the high threshold; and a Low Threshold Decision unit 77n tests whether all the comparison outputs exceeded the low threshold. The combination of the outputs of decision table 77n and 77m is the alarm value. These eight alarm values are inputted to the decision table 66 which outputs the defect flag to the post-processor 14 (FIG. 12) via the parameters buffer 68.

The post-processor 14 (FIG. 12) thus receives the list of suspected defects, together with their relevant parameters, and makes decisions before passing them onto the Phase II examination system. These decisions include: (a) clustering; (b) choosing the points which will be passed to Phase II; and (c) the optimum route in Phase II. The latter functions are carried out by microprocessor programs.

Phase II Examination

Overall System

As briefly described earlier, the Phase II examination is effected automatically upon the completion of the Phase I examination while the wafer is still on the table 2, but only with respect to those locations of the wafer W indicated during the Phase I examination as having a high probability of a defect. Thus, while the Phase I examination is effected at a relatively high speed and with a relatively low spatial resolution, the Phase II examination is effected at a much lower speed and with a much higher spatial resolution, to indicate whether there is indeed a defect in those locations suspected of having a defect during the Phase I examination.

Briefly, the Phase II examination is effected by: imaging on converter 9 (FIGS. 1 and 26), e.g., a CCD, each suspected location of the inspected pattern, and the corresponding location of the reference pattern, to output two sets of electrical signals corresponding to the pixels of the inspected pattern and the reference pattern, respectively; and comparing the pixels of the inspected pattern with the corresponding pixels of the reference pattern to indicate a defect whenever a mismatch of a predetermined magnitude is found to exist at the respective location. To accommododate variations in the thickness of the wafer and/or pattern, and/or multi-layer patterns each suspected location of the inspected pattern, and the reference pattern is imaged at a plurality of different depths, and the electric signals of one set are shifted with respect to those of the other set to match the respective depths of the images.

Phase II Optic System

Figure 26:
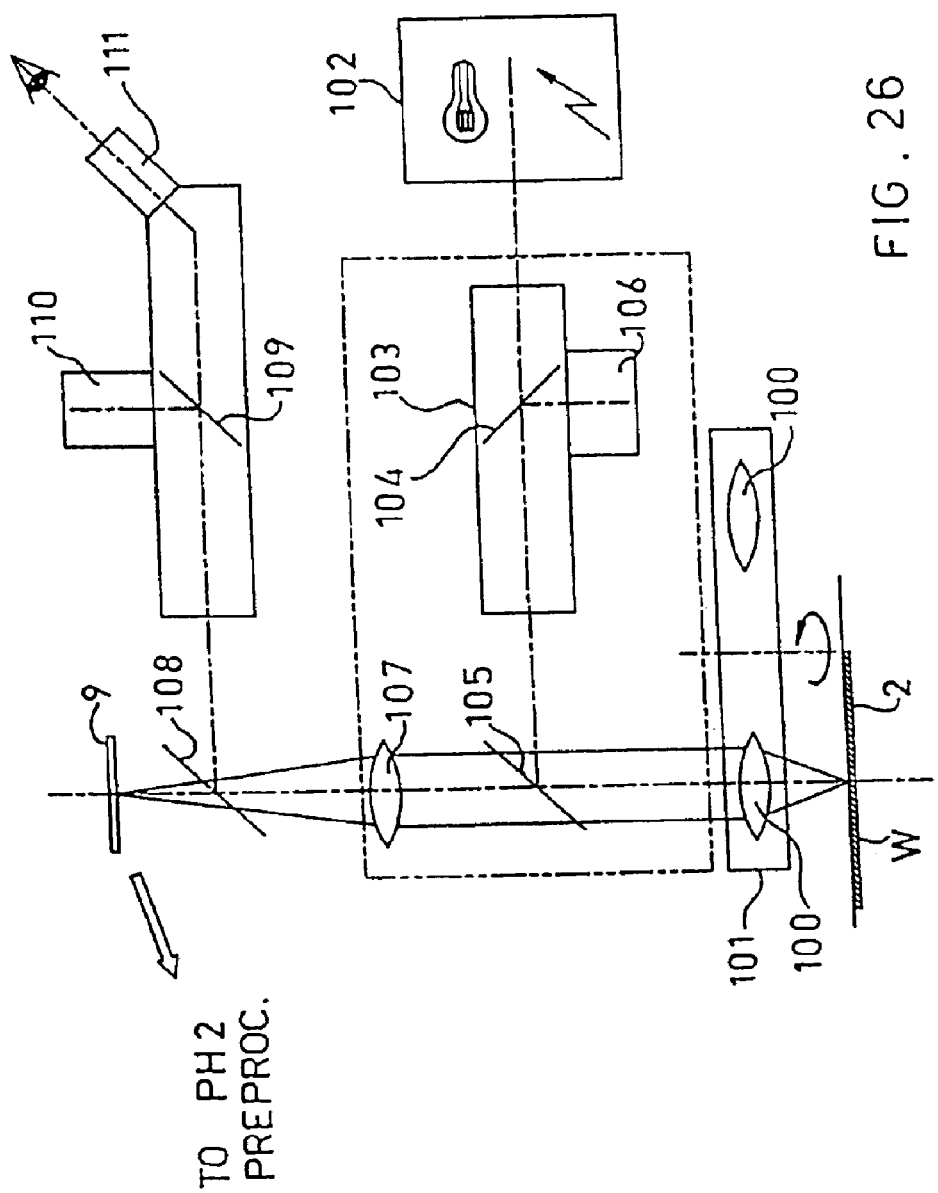
FIG. 26 is a diagram illustrating the main elements of the Phase II optic system.

The Phase II optic system is shown generally in FIG. 1 and more particularly in FIG. 26. It includes a microscope objective 100 mounted in a rotating turret 101 carrying different objectives to enable bringing a selected one into the optical path between the wafer W and the image converter 9. The wafer W is illuminated by a flashlamp unit 102 via an optical device 103 having a beamsplitter 104 and a second beamsplitter 105. Unit 102 also contains a continuous light source, such as a standard tungsten lamp, which is used with a standard TV camera 110 and/or viewing system III, described below.

Beamsplitter 104 reflects the infrared portion of the light reflected from the wafer to an autofocus unit 106, while beamsplitter 105 reflects the flash light to the wafer W on the vacuum chuck 24 (FIG. 3) via the selected objective 100. Beamsplitter 105 also passes the light reflected by the wafer W via an imaging lens 107 and another beamsplitter 108 to the image converter 9. Beamsplitter 108 reflects a part of the image via another beamsplitter 109 to a standard TV camera 110 and/or to a viewing system 111 having binocular eyepieces. The binocular viewing system 111 permits an observer to view the wafer visually, while the TV camera 110 permits viewing the wafer via a TV monitor.

Phase 2 Image Processor

Figure 27:
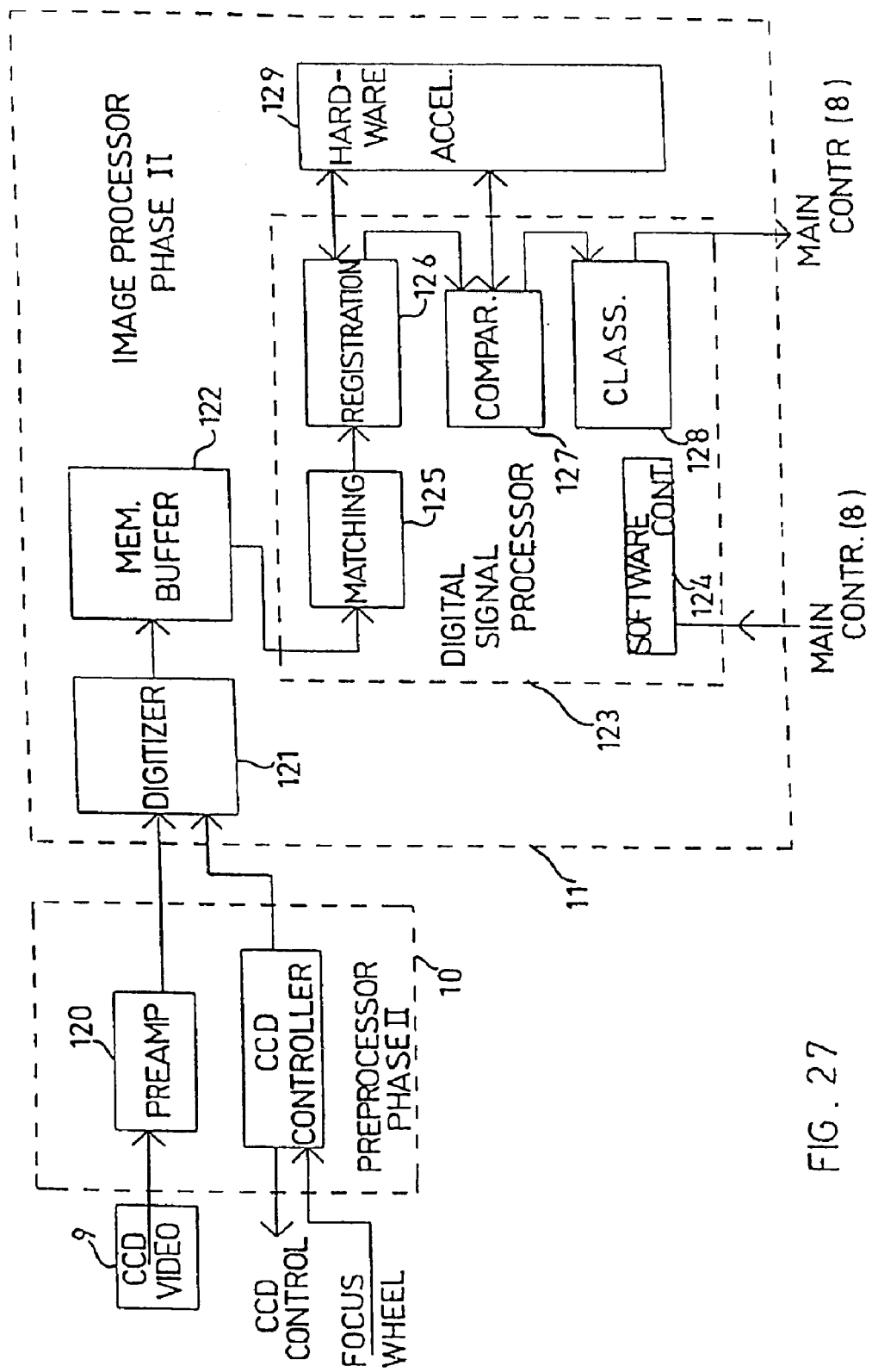
FIGS. 27–31 are diagrams illustrating the construction and operation of the Phase II examination system.

FIG. 27 illustrates both the Phase 2 image preprocessor 10 and the Phase 2 image processor 11.

The information detected by the image converter 9 is fed to a preamplifier 120 in the preprocessor 10, to a digitizer 121, and then to a memory buffer 122 in the image processor 11. The image processor 11 further includes a digital signal processor which, under software control (block 124) from the main controller (8, FIG. 2), performs the following operations as indicated in FIG. 27: a matching operation 125, a registration operation 126, a comparison operation 127, and a classification operation 128. The output from the digital signal processor 123 is then returned to the main controller 8.

FIG. 27 further illustrates the Phase 2 image processor 11 as including a hardware accelerator 129 for accelerating particularly the registration and comparison operations.

The foregoing operations are described more particularly below with reference to FIGS. 28–31.

As described earlier, the input to the Phase II image processor includes two sets of images, taken from the inspected pattern and the reference pattern, respectively. Each set includes five images taken with focusses at different depths in order to accommodate variations in the thickness of the wafer or pattern, or to accommodate multi-layer patterns.

Figure 28:
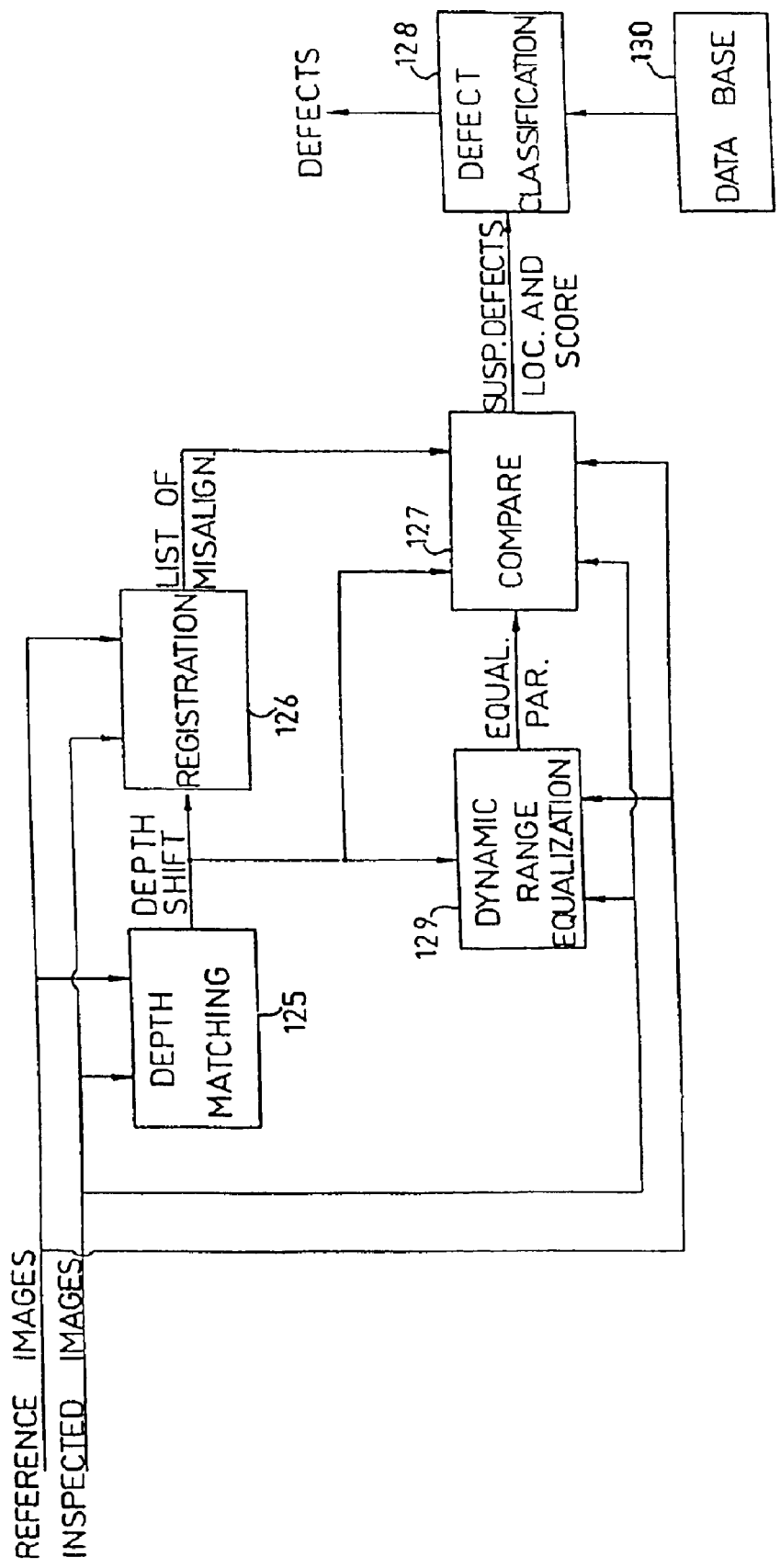

As more particularly shown in FIG. 28, the reference images and the inspected images are subjected to a depth matching operation 125 matching the two depth sets, and also to a registration operation 126, in which misalignment between the reference and inspected images is detected in each depth. The list of misalignments is fed to the compare circuit 127. Circuit 127 compares the grey level images, pixel by pixel, using surrounding pixels and adaptive thresholds obtained from a dynamic range equalization circuit 129, the latter circuit compensating for process, illumination and other variations. The output of compare circuit 127 indicates suspected defects, location and score, and is fed to the defect classification circuit 128. Circuit 128 characterizes the data defects utilizing, not only the output of the compare circuit 127, but also previously gathered data as stored in the data base 130. The output of the defect classification circuit 128 is fed to the main controller (8, FIGS. 1, 2) for display, print-out, or the like.

Depth Matching

Figure 29:
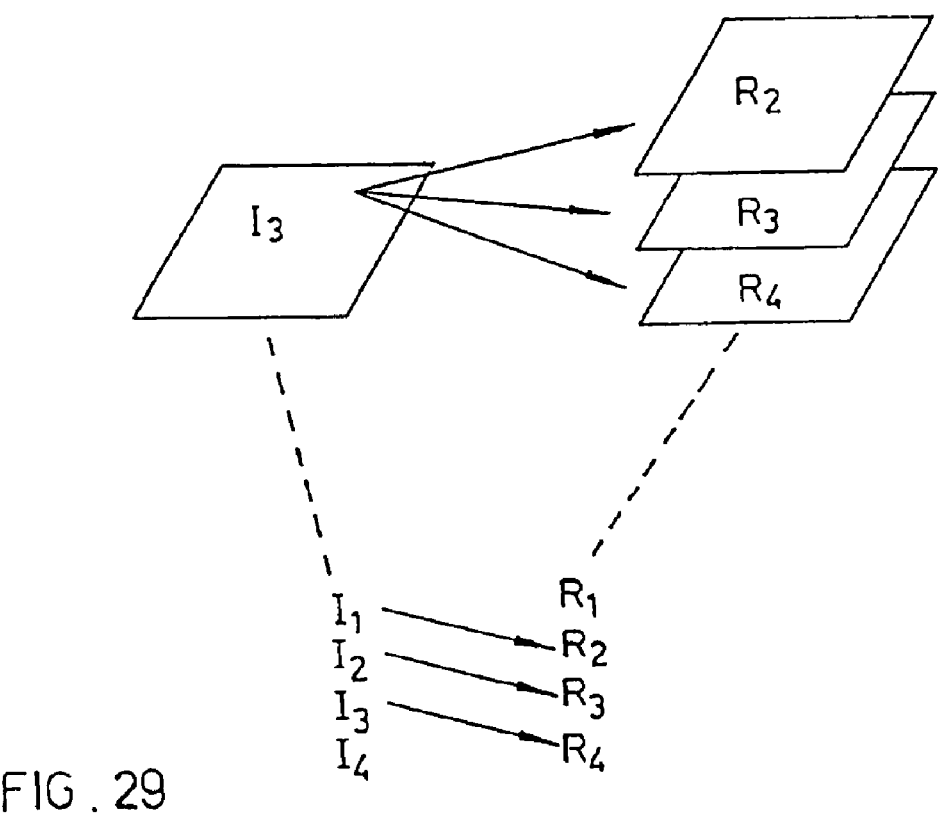
Figure 30:
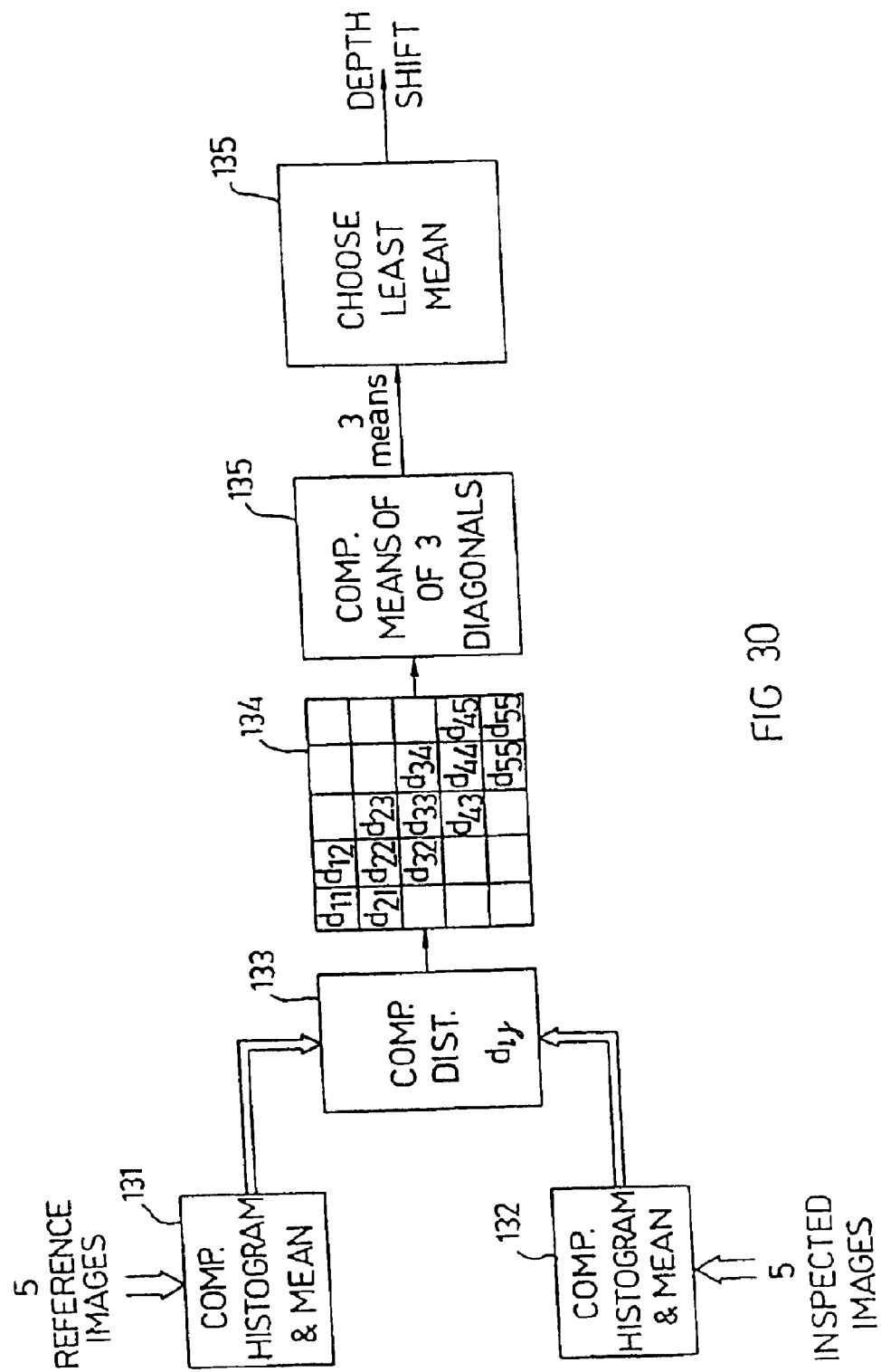
Figure 31:
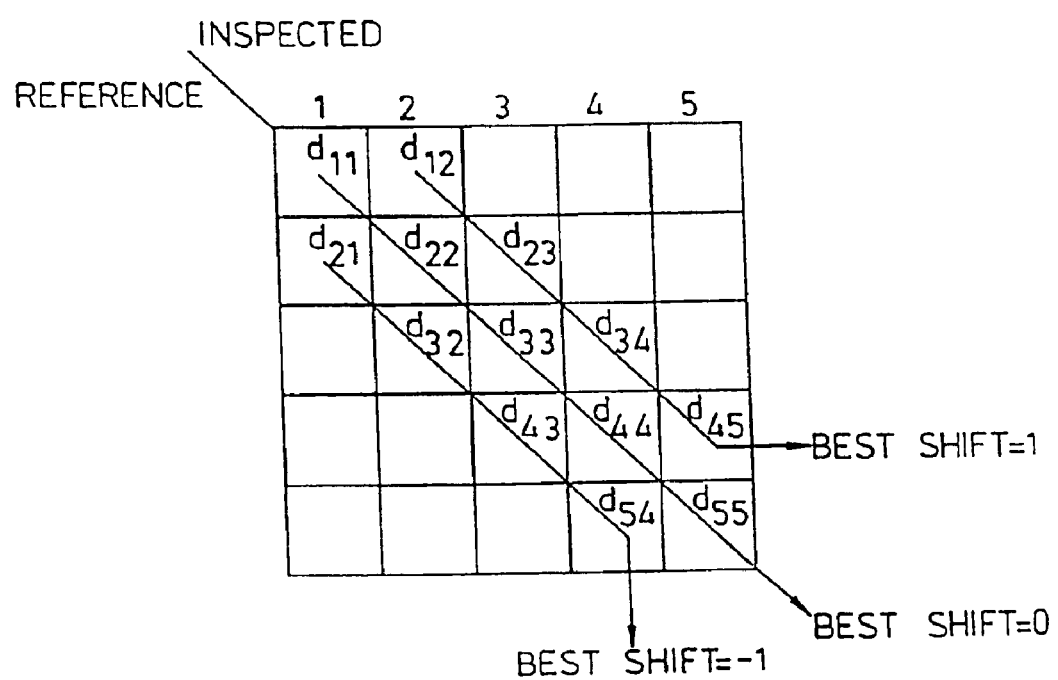

FIGS. 29–31 more particularly illustrate how the depth matching operation is performed. Thus, the sequence of images taken from the inspected pattern is matched with those taken from the reference pattern. The goal is to match each image of the inspected pattern with the image of the reference pattern taken at the corresponding depth of focus. Two assumptions are made: (1) the images are taken in the order of increasing depth with a fixed difference between each two consecutive images; and (2) the error in the depth of the first image of the two sequences is at most the difference between two consecutive images.

Hence. if $I_i$, $1 \leq i \leq 5$ and $R_i$, $1 \leq i \leq 5$ are the inspected and reference images, respectively, the matching procedure detects x, where x is one of −1,0 or 1 such that $(I_i, R_{i+x})$ is a pair of comparable images (see FIG. 29), for i=1, . . . , 5. Correlation in the depth of focus of two images to measured by computing similarity in the variance of grey levels in the two images. The correlation measure used is the difference between the grey level histograms of the images. The shift x is computed as the one providing the best correlation for all images in the sequence.

FIG. 30 more particularly illustrates the matching procedure. It is composed of the following steps:

(1) Compute the grey level histograms for all the images (blocks 131, 132). The grey level histogram of an image contains the distribution of the grey levels. The histogram H of an image contains in its $j^{th}$ cell H(j), the number of pixels in the image that has a grey level equal to j.

(2) Compute the distance between the histograms (block 133). The distance is taken as the sum of absolute differences between corresponding cells in the histograms. The distance will be computed as follows:

$$d(R_k - I_1) = \sum_i |H_{Rk}(i) - H_{I1}(i)|,$$

wherein $H_{Rk}$, $H_{I1}$, are the histograms of $R_k$, $I_1$ respectively.

(3) Create the distances table (block 134). This table contains the correlation measures computed for each pair of images.

d(R$_1$-I$_1$) d(R$_1$-I$_2$) d(R$_1$-I$_3$)

d(R$_2$-I$_1$) d(R$_2$-I$_2$) d(R$_2$-I$_3$)

(4) Find the diagonal in the distance table providing the least means (see FIG. 31) by computing the means of the three main diagonals (block 135), and choosing the least mean (block 136), to produce the depth shift. The shift x corresponds to the diagonal providing the minimal mean, thus minimizing the overall distance between the two sets.

Repetitive-Pattern-Comparison

Figure 32:
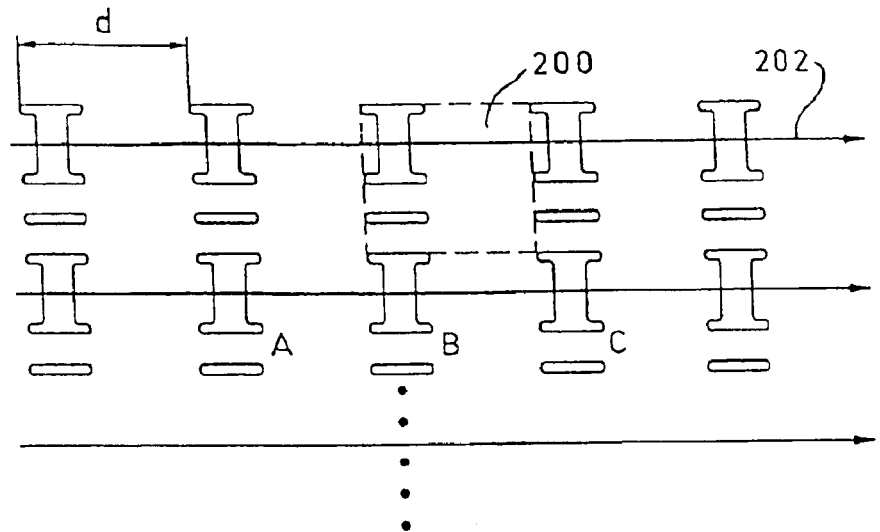
FIG. 32 is a diagram helpful in explaining the repetitive-pattern comparison technique.

As described above, both the Phase I and the Phase II examinations may be effected by a die-to-die comparison or by a repetitive-pattern comparison of repetitive pattern units on the same die (or other article). FIG. 32 illustrates such a repetitive pattern on the same die.

The repetitive pattern illustrated in FIG. 32 consists of a number of relatively small (e.g. a few microns in size) comparable units. A typical comparable unit in a repetitive-pattern comparison is shown as the area bounded by the dashed line 200 in FIG. 32. As therein shown, each pixel along the scanning line 202 is comparable to a pixel which is located at a distance "d" either to its left or to its right. Since the two pixels that have to be compared are contained in the same scanning line, no registration has to be done between the "inspected" and the "reference" image, as will be shown below.

Figure 33:
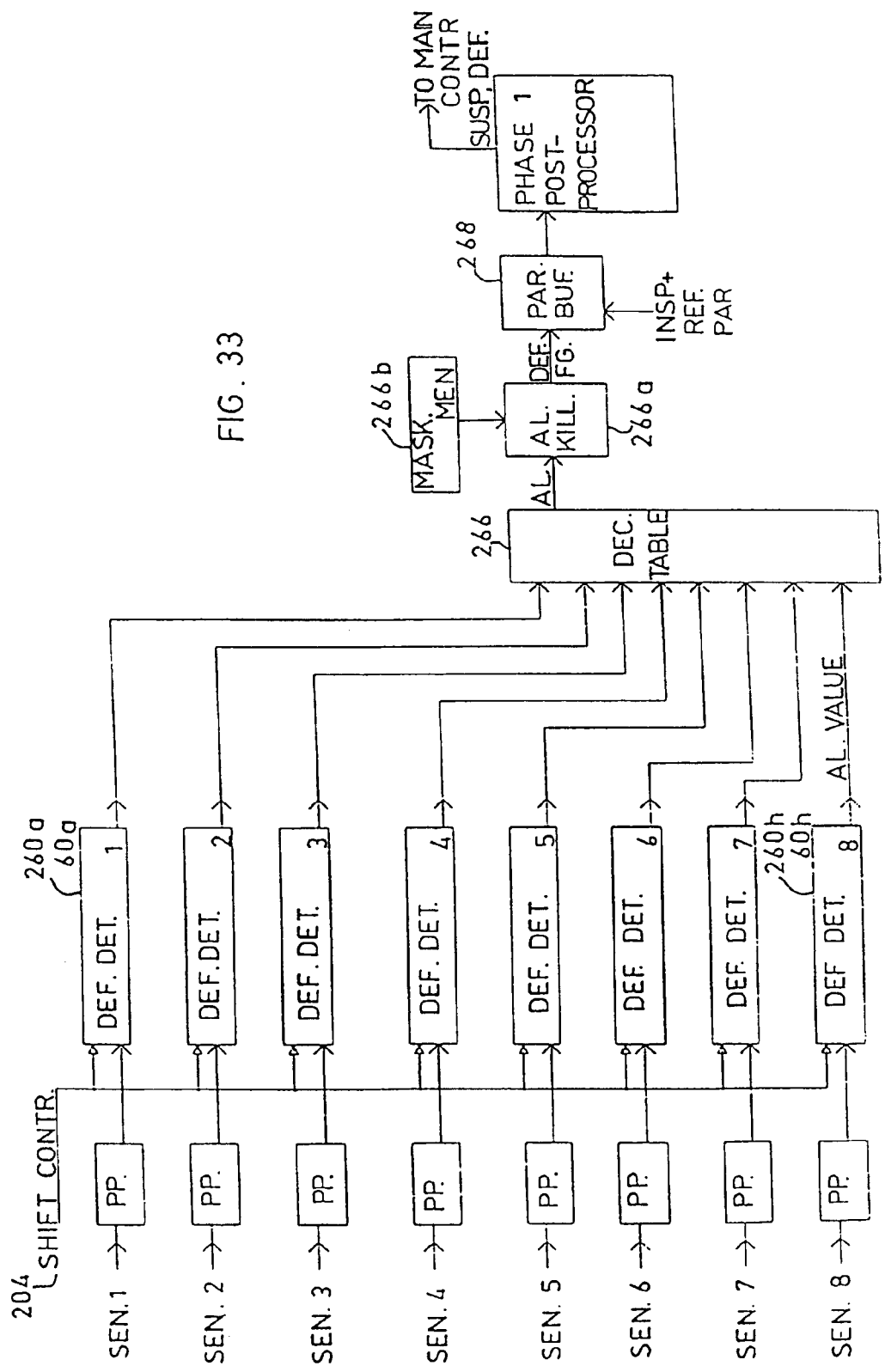
FIGS. 33, 34 and 35 are block diagrams corresponding to FIGS. 12, 14 and 24, respectively, but showing the modifications for the repetitive pattern-pattern comparison technique.
Figure 34:
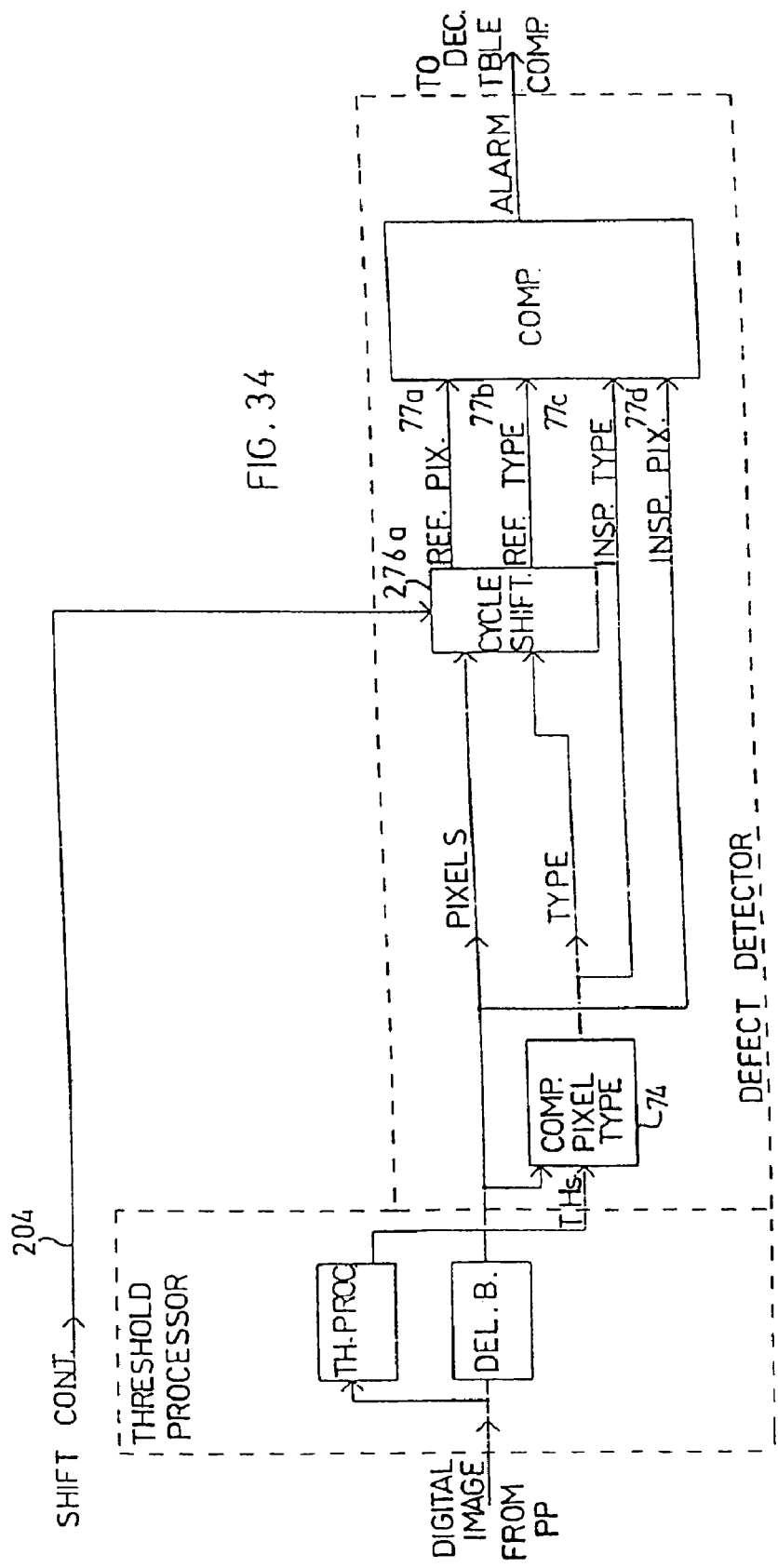
Figure 35:
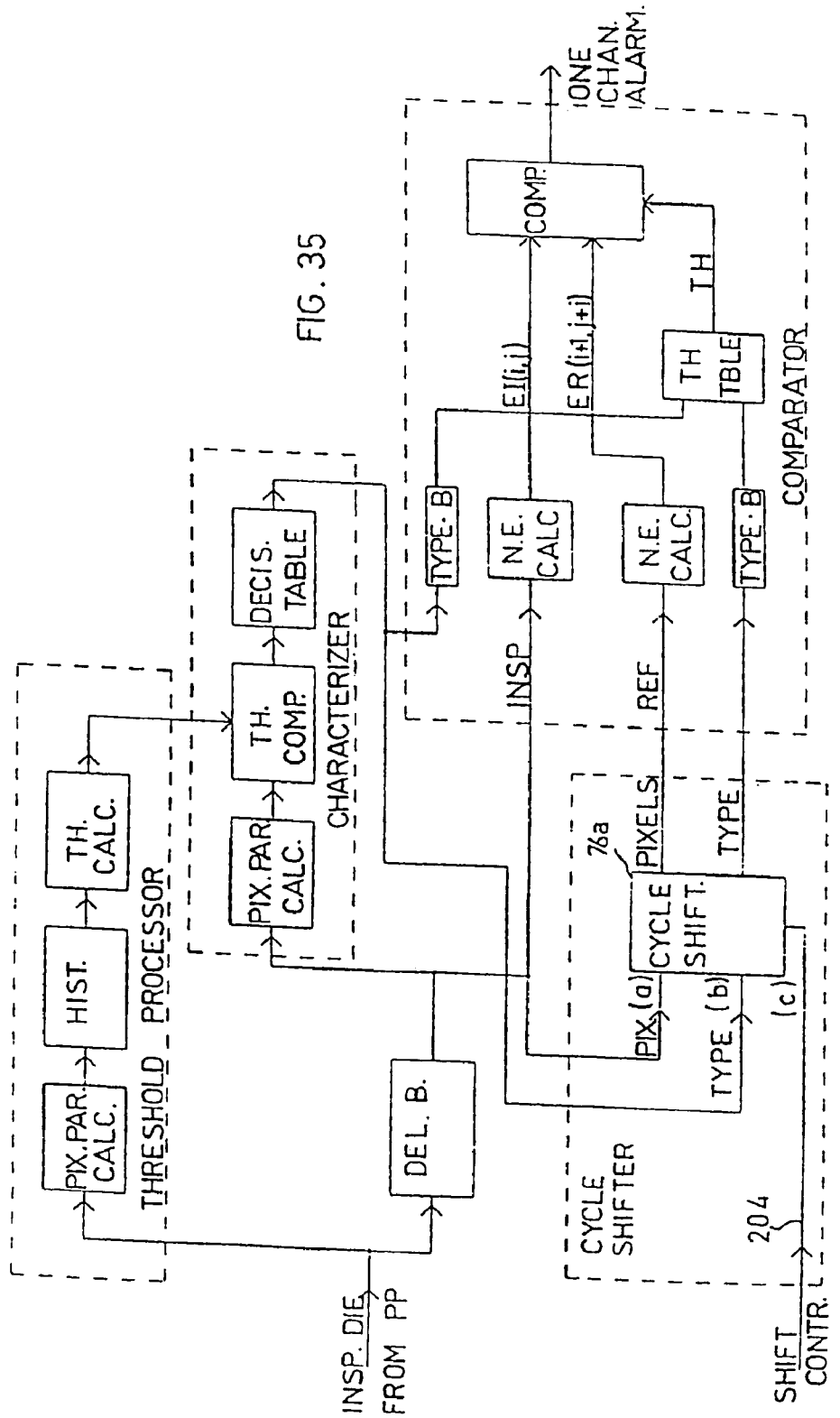

FIGS. 33, 34 and 35 are block diagrams which correspond to FIGS. 12, 14 and 24, respectively (which figures relate to a die-to-die comparison in the Phase I examination), but show the changes involved in a repetitive-pattern comparison. To facilitate understanding, and also to simplify the description, only those changes involved in the repetitive-pattern comparison of FIGS. 33, 34 and 35 are described herein; in addition, comparable elements are generally correspondingly numbered as in FIGS. 12, 14 and 24, respectively, except are increased by "200".

With respect to the overall functional block diagram illustrated in FIG. 33, the system receives as inputs: (1) signals from the N sensors (N-8 in the illustrated embodiment), and (2) a shift control signal 204 which determines the distance (in pixels) between the current pixel and the shifted pixel to which the current pixel is compared. The shift (in pixels) corresponds to the distance "d" in FIG. 32, and is supplied to the system by the user prior to an inspection operation. The system processes the N input signals and outputs a list of locations suspected as defects.

The system illustrated in FIG. 33 (relating to a repetitive-pattern comparison) differs from that in FIG. 12 (relating to a die-to-die comparison) in the following respects:

(1) The alignment control unit 262, and the registrator units 264a–264h for each second detection circuit 260a–260h appearing in FIG. 12, are absent from FIG. 2.

(2) A shift control signal 204 is inputted to determine the comparison distance ("d", FIG. 33).

(3) Following the decision table 266, an alarm killer unit 266a is added. Its function is to suppress detect indications which result from non-repetitive zones, i.e., zones in which the comparison distance is not equal to "d". The inputs to the alarm killer unit 266a are an Alarm Flag from the decision table 266 and a Masking Flag from a masking memory 266b. The output of the alarm killer circuit 266a to a Defect Flag, which is "1" (meaning "defect") if both the Alarm Flag and the Masking Flag are "1".

The masking memory 266b generates information needed for the alarm killer unit 266a in order to suppress false indications of defects that result from non-repetitive zones. Its input is a bit-map which contains a "0" for the pixels that must not be compared (i.e., pixels for which the comparison distance is not equal to "d"), and a "1" where the comparison distance is equal to "d". The bit-map is generated by the user by interactive means prior to inspection, and is loaded slice-by-slice to the masking memory 266b during inspection. The masking memory 266b outputs a Masking Flag which is a "0" for pixels that are not to be compared, and a "1" for pixels that are to be compared.

FIG. 34 illustrates one channel in the processing system of FIG. 33 for a repetitive-pattern comparison. It will be seen that the following units appearing in the corresponding FIG. 14 (for a die-to-die comparison) are absent in FIG. 34 (1) the pixel characterizer 72; (2) the score matrix calculator 73; (3) the reference die memory 15; and (4) the pixel aligner 76. The first two of the above units (72, 73) deal with the registration between the reference and the inspected die; and since registration is not needed in a repetitive-pattern comparison, they are omitted from FIG. 34. The reference die memory 75; and the pixel aligner 76 are replaced by the cycle shifter 276a. As mentioned earlier, the shift control signal 204 determines the amount of shift (in pixels) between the reference pixels and types (inputs a and b to the comparator 272), and the corresponding inspected pixels and types (inputs c and d to the comparator 272).

FIG. 35 illustrates more particularly the Defect Detector Portion of the image processor of FIG. 34, and corresponds to FIG. 24. This circuit compares each pixel to its corresponding shifted pixel according to the shift amount determined by the shift control signal 204; and the comparison generates a one-channel alarm for each pixel having a signal which is significantly larger than their corresponding shifted pixels.

Following are the main differences between the circuit illustrated in FIG. 35 (for a repetitive-pattern comparison) with respect to the system of FIG. 24 (for a die-to-die comparison): The reference die memory (75, FIG. 24) and the pixel aligner (76, FIG. 24) are replaced by the cycle shifter 276a, as described above. The cycle shifter 276a generates a shift (in pixels) which corresponds to the comparable unit distance (d) in FIG. 34. The shifter amount is determined by the shift control input 204. The cycle shifter 276a has three inputs: (a) inspected pixels, (b) inspected types, and (c) shift control signal 204. The cycle shifter 276a is a standard shift register with programmable length. The delay length is determined by the shift control signal 204.

Improvements in Phase II Examination

Figure 37:
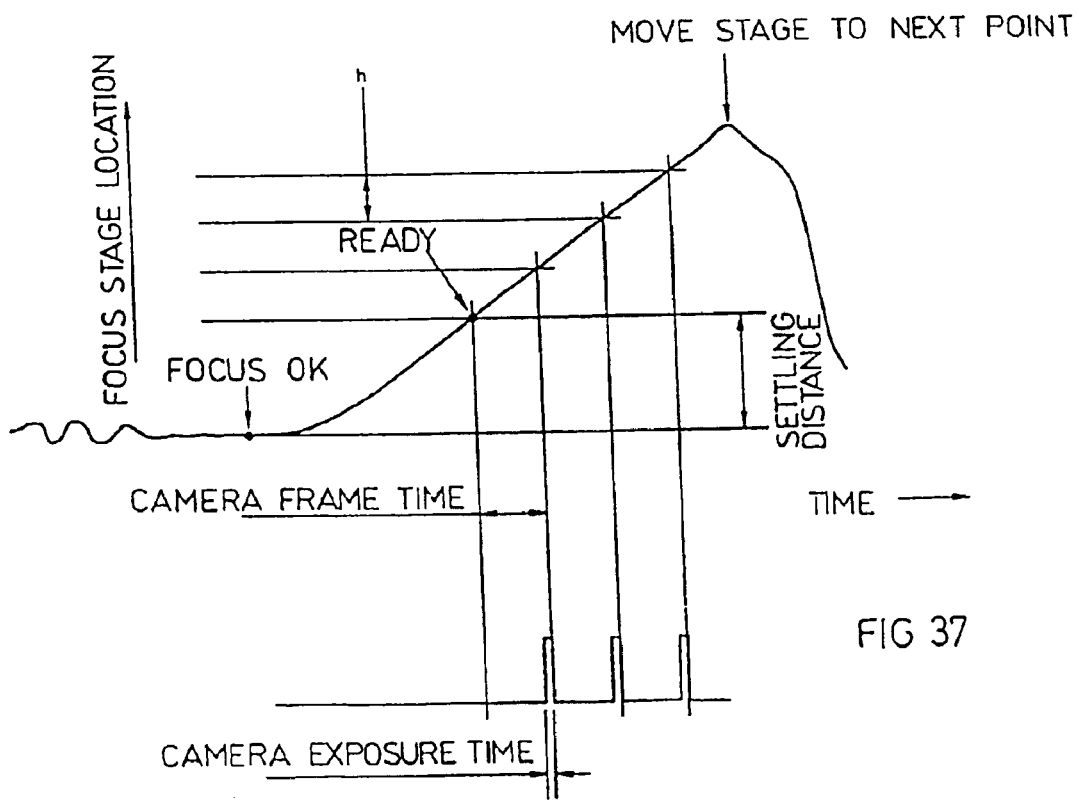
FIG. 37 is a diagram helpful in explaining the modifications in the Phase II examination.
Figure 36:
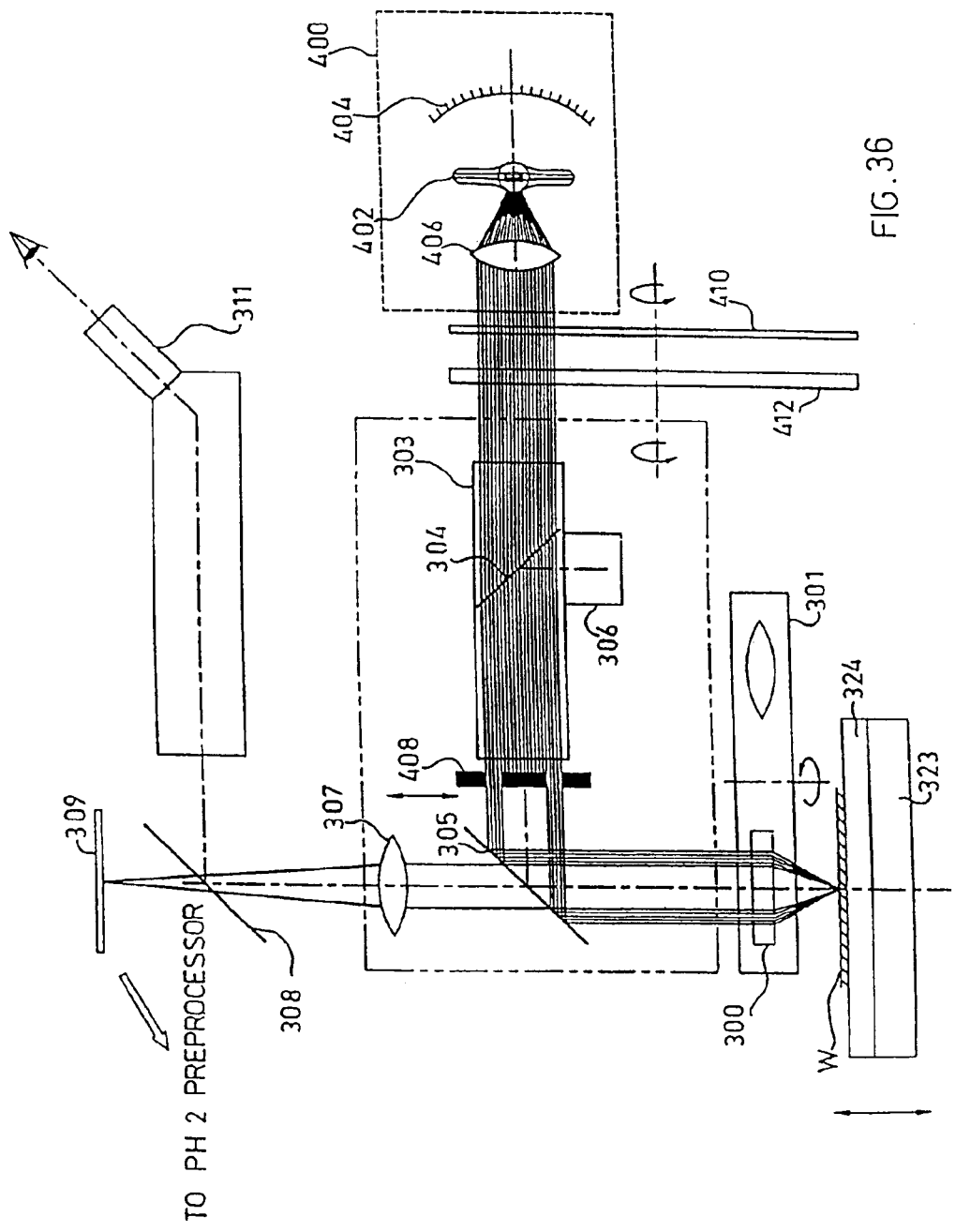
FIG. 36 is an optical diagram corresponding to FIG. 26, but illustrating modifications in the Phase II examination.

FIGS. 36–39 illustrate a number of improvements in the Phase II examination system described above. FIG. 36 generally corresponds to FIG. 26, but illustrates certain modifications to be described below; FIG. 37 is a diagram helpful in explaining these improvements; and FIGS. 38 and 39 generally correspond to FIGS. 27 and 28, but show the modifications also to be described below. To facilitate understanding and to simplify the description, only the changes included in FIGS. 36, 38 and 39, as compared to FIGS. 26, 27 and 28 are specifically described below; in addition generally comparable elements are identified by the same reference numerals except increased by "300", and now elements are identified by reference numerals starting with "400".

A main difference in the optical system illustrated in FIG. 36, as compared to FIG. 26, is that the FIG. 36 optical system uses darkfield imaging of the object, rather than brightfield imaging. Thus, it has been found that darkfield imaging increases the sensitivity to small defects, compared to standard brightfield imaging. Using darkfield imaging in the Phase II examination is superior in confirming or rejecting alarms detected in Phase I, thereby producing a higher probability of detection and a smaller probability of false alarms.

The Phase II optical system as shown in FIG. 36 includes a darkfield microscope objective 300 mounted in a rotating turret 301 carrying different objectives to enable bringing a selected one into the optical path between the wafer W and the image converter 309. The wafer W is illuminated by an illumination unit 400 via an optical device 303 including beam splitters 304 and 305. Unit 400 is a standard unit. based on a mercury lamp, such as supplied by Leitz. It consists of a 200 watt mercury lamp 402, a reflector 404, and a condenser 406.

Beam splitter 304 reflects the infrared portion of the light reflected from the wafer W to an autofocus unit 306, while beam splitter 305 reflects the light from unit 400 to the wafer W on the vacuum chuck 324 via the selected objective 300. Beam splitter 305 also passes the light reflected by the wafer W via an imaging lens 307 and another beam splitter 306 to the image converter 309. Beam splitter 308 reflects a part of the image to a viewing system 311 having binocular eyepieces, permitting an observer to view the wafer visually.

The image converter 309 is a CCD camera with exposure control, such as the Pulnix TM 64.

FIG. 36 further includes a darkfield shutter 408 which enables the optics to generate darkfield images by blocking the central zone of the illumination beam IB. The optical system illustrated in FIG. 36 further includes an ND-filter 410 which is used to adjust the illumination intensity on the object, and a colour filter 412 which is used to enhance the contrast of the image.

FIG. 37 illustrates the imaging of a number of depth images at a single location. In the illustrated example, there are three such depth images, but practically any number can be generated according to the technique described below.

The imaging of the locations identified as having a high probability of a defect as a result of the Phase I examination, is accomplished as follows: the wafer is first moved by means of the XY stage (22, FIG. 3) so that the possible defect detected by the Phase I examination is located beneath the Phase II objective 300 (FIG. 36). The autofocus 306 focusses the lens at a predetermined depth relative to the object's surface by moving the rotation/level/focus stage 323 to the proper Z-position.

The rotation/level/focus stage is accelerated to a constant predetermined velocity equal to the separation distance (h) between the depth images, divided by the time between frames. When the settling distance is passed, three (or any other number) of images are recorded at equally spaced intervals.

The separation distance (h) between the depth images is approximately equal to the depth of focus. This ensures that the defect will be imaged at focus at least in one of the depth images.

Another feature of the imaging technique illustrated in FIG. 37 is that the exposure time used for each image is significantly shorter than the frame time. This prevents the image from smearing due to continuous motion of the stage 323 in the Z-direction at the time the images are recorded. As one example, the frame time may be approximately 16 msec, while the exposure time may be 0.5 sec. This short exposure time is achieved by the built-in exposure control of the CCD camera 309.

Figure 38:
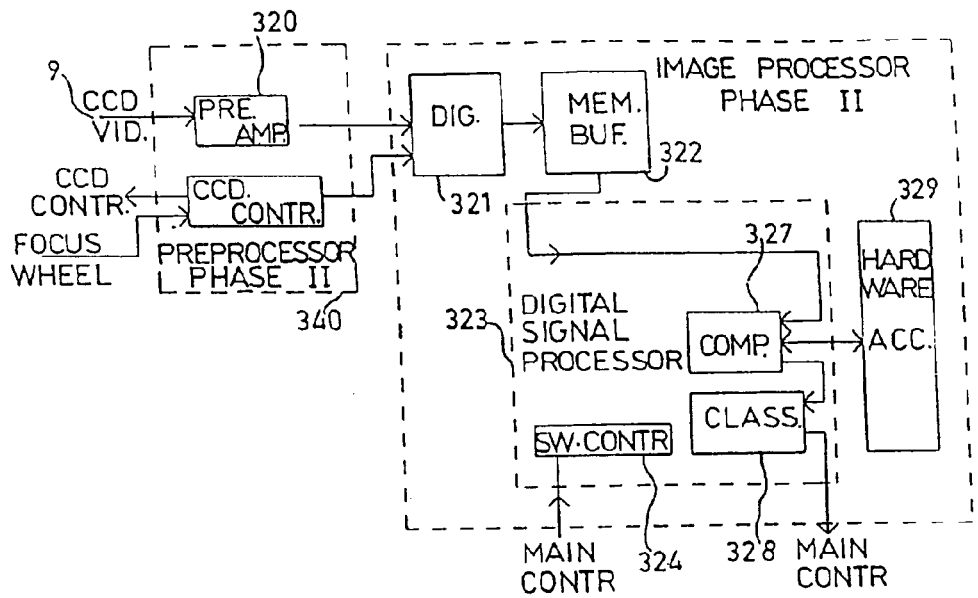
FIGS. 38 and 39 are block diagrams corresponding to FIGS. 27 and 28, respectively, but showing the changes in the Phase II examination.

FIG. 38 illustrates both the Phase II image preprocessor 310 and the Phase II image processor 311.

The information detected by the image converter 309 is fed to a preamplifier 320 in the preprocessor 310, then to a digitizer 321, and then to a memory buffer 322 in the image processor 311. The image processor 311 further includes a digital signal processor which, under software control (bock 324) from the main controller (8, FIG. 2), performs a comparison operation 327, and a classification operation 328. Since the comparison distance (d) is small for typical repetitive patterns, it is assumed that the CCD frame contains at least two comparable units. Therefore, it does not perform a matching operation or a registration operation, corresponding to operations 123 and 126 in FIG. 27. The output from the digital signal processor 323 is then returned to the main controller.

FIG. 38 further illustrates the Phase II image processor 311 as including a hardware accelerator 329 for accelerating particularly the comparison operation.

The foregoing operations are described more particularly below with reference to FIG. 39.

The input to the Phase II image processor includes a set of images taken from the inspected pattern in the neighbourhood of a suspected location designated by the Phase I image processor. A set includes five images taken with focusses at different depths in order to accommodate variations in the thickness of the wafer or pattern, or to accommodate multi-layer patterns.

The suspected location zone is compared against a similar pattern neighbourhood in the image, located at the distance "d", left to it, as illustrated in FIG. 32.

Figure 39:
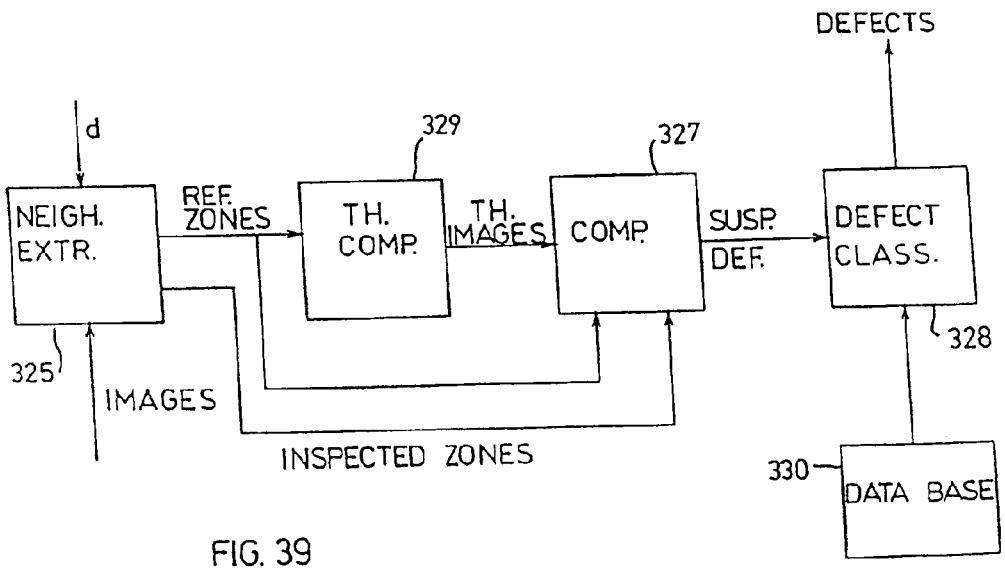

As more particularly shown in FIG. 39, the images are subjected to a neighbourhood extraction operation 325, outputting an inspected zone and a reference zone for each image in the set.

Circuit 327 compares the gray level images, pixel by pixel, using surrounding pixels and adaptive thresholds obtained from a threshold computation circuit 329. The latter circuit computes the thresholds at each pixel location according to the feature detector contained in circuit 324.

The output of compare circuit 327 indicates suspected defects, location and score, and is fed to the defect classification circuit 328. Circuit 328 characterizes the data defects utilizing, not only the output of the compare circuit 327, but also previously gather data as stored in the database 330. The output of the defect classification circuit 328 is fed to the main controller (8, FIGS. 1 and 2) for display, printout, or the like.

Die-to-Database-Comparison

Instead of using, as a reference to be compared with the data derived from the inspected article, data generated from real images of another like article (in the die-to-die comparison), or of another like pattern on the same article (repetitive pattern comparison), the reference data may be generated from simulated images derived from a database; such a comparison is called a die-to-database comparison.

The main idea of a die-to-database comparison is: (a) to model the database into scattering images, and (b) to compare these images against the images acquired by the imaging system from the article under inspection. The modelling, or simulating of the images, is carried out using the method described below. The modelled or simulated images are inputted to the system and play the role of the reference die (in the die-to-die comparison), or of the repetitive pattern (in the repetitive pattern comparison).

Figure 40:
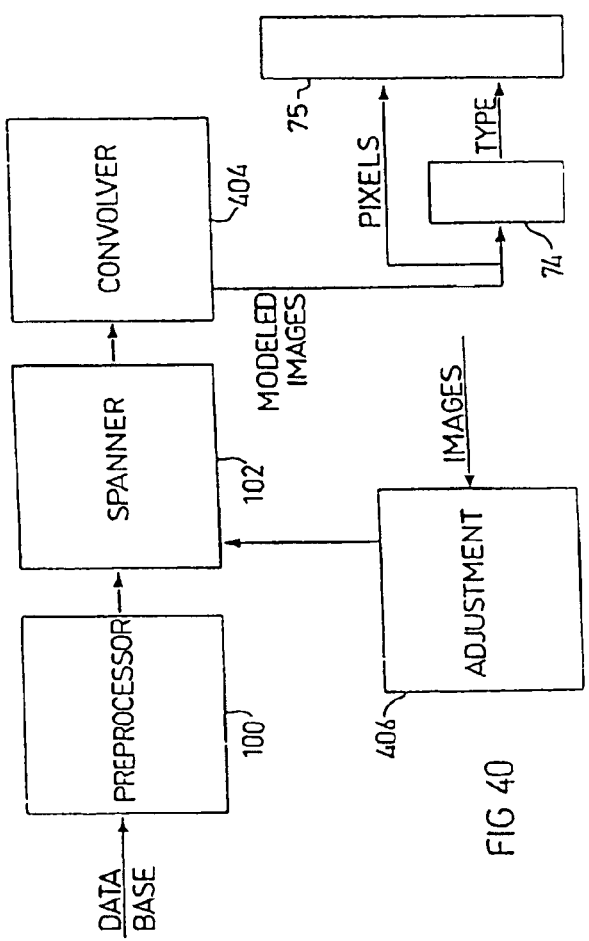
FIG. 40 is a block diagram illustrating an implementation of a die-to-database comparison technique.

Thus, in the embodiment illustrated in FIG. 14, each of the eight modelled images is inputted to its corresponding reference die memory (75, FIG. 14) in the die-to-database comparison described below, and is used as the reference stream input to the comparator (72, FIG. 14). The above is more particularly illustrated in the block diagram of FIG. 40, which consists of four blocks of the modelling system: a preprocessor 400, a spanner 402, a convolver 404, and an adjustment unit 406. The preprocessor 400 and the adjustment unit 406 are used prior to inspection, while the spanner 402 and the convolver 404 are used during inspection.

The modelling of the scattering is based on the following principles:

(a) the pattern of the object consists of typical features, such as corners and curves, and (b) the modelling extracts these features from the database and associates with each feature its corresponding scattering signal.

A feature is part of the pattern which may be described by some attributes. The pattern on the inspected object is described by a list of features. A feature may be either a corner or a curve.

Figure 41:
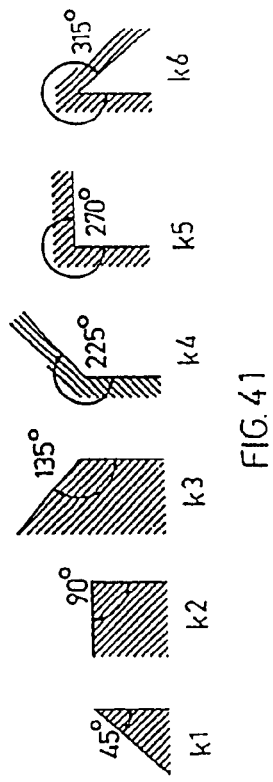

There are six kinds of corners, as illustrated in FIG. 41. Each corner may appear in one of eight possible orientations. The orientations are given by $0=45°t$, where $t=0, 1, ---7$. The corners in FIG. 10 are in the orientation of $0=0°$ (that is, $t=0$)

A corner location is the location of the edges intersection. The corner characteristics are:

k—kind, (see FIG. 41)
t—orientation $t=0, ---, 7$.

Figure 42:
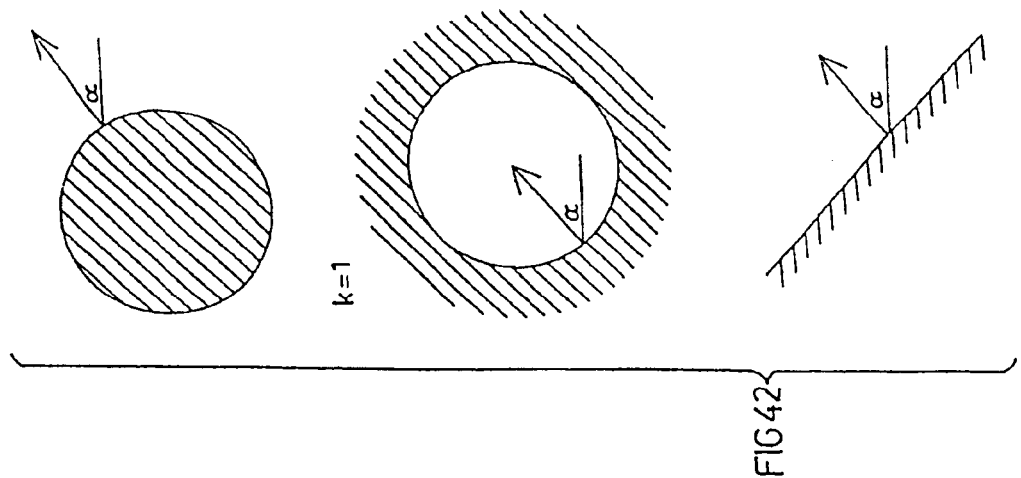
FIGS. 41 and 42 are diagrams illustrating the kinds of corners, and kinds of curves, involved in the system of FIG. 40.

There are three kinds of curves as shown in FIG. 42. Curvature $C=R^{-1}$ (>,0), and normal direction $\alpha(0 \leq \alpha \leq 360)$, are associated with each unit length (e.g., one pixel) of curve $k=1$ or $k=2$ kind. Curve $C=0$, normal direction $\alpha$, $0<\alpha<360$ and length are associated with each kind $k=3$ curve. The normal direction is always from black to white. This curve location is the center of the curve.

The curve characteristics are as follows;

k—kind, $k=1,2,3$ (see FIG. 42)
L—Length, if $k=1$ or $k=2$ then $L=1$, if $k=2$ then $L \geq 1$.
c—Normal direction from black to white, $0 \leq \alpha \leq 360$.
C—Curvature is computed from the radius by $R^{-1}$.

To summarize: each feature is represented by class, location, and characteristics, where: Class is either a corner or a curve; and location is given by (x, y) in a resolution higher than the imaging resolution (that is, if pixel size in the image is "p", the location resolution is at least p/16). The resolution is chosen such that a pinhole/pin dot is at least four pixels.

The following table summarizes the above:

| Class | Corner | Curve |
| --- | --- | --- |
| Characteristics | K, t | K, L, α, C |
| Location | Edge Intersection | Center of Curve |

Figure 43:
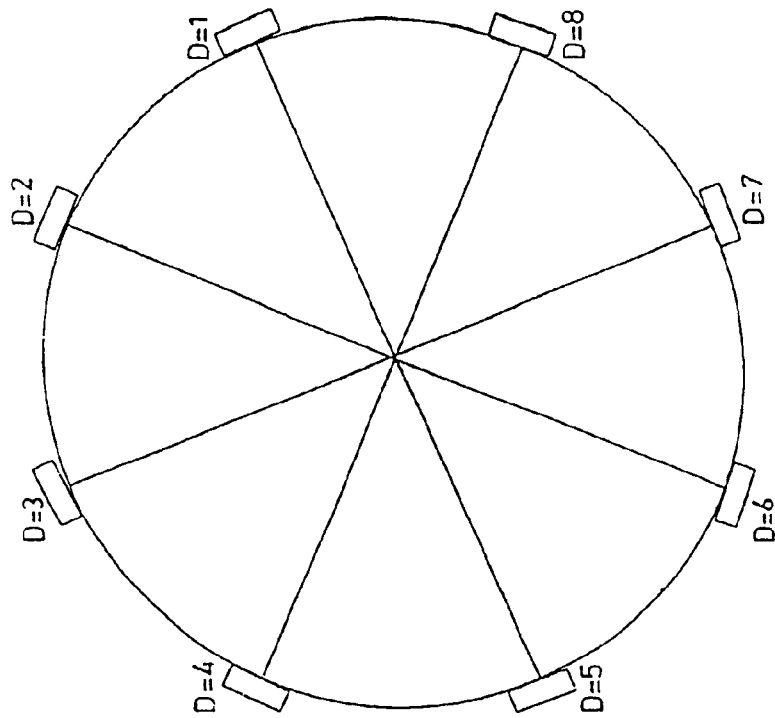
FIG. 43 is a diagram illustrating the array of detectors involved in the system of FIG. 40.

The role of the modelling is to generate, based on the features described above, a plurality of synthetic or simulated scattering images to be compared to the actual image detected by the detectors. In this case, there are eight detectors $D_1$–$D_8$, arranged in a circular array, as illustrated in FIG. 43.

The modelling consists of two steps: First, high-resolution scattering images are generated; and second, the images are convolved in order to simulate the optic smears. Two different models are used: one model for corners, and another model for curves.

In the modelling of corners, data is computed regarding the scattering intensity and the corner shift. The scattering intensities, $f(k,t)$, for all kinds of corners $k(k=1,2, ---8)$ and orientations ($t=0,1, ---7$) for detector $D_1$ are measured and saved. The scattering intensity I of corner k at orientation t and detector D is calculated as follows:

$$I(k,t,D)=f(k,[t-D])$$

where $[t-D]=(t-D)$ module 8.

With each corner kind (k), a corner shift (r,θ) [k] is also measured and saved in polar coordinates for $t=0$.

The corner shift represents the actual location of the corner relative to its location in the database, and is a function of the manufacturing process.

Figure 44:
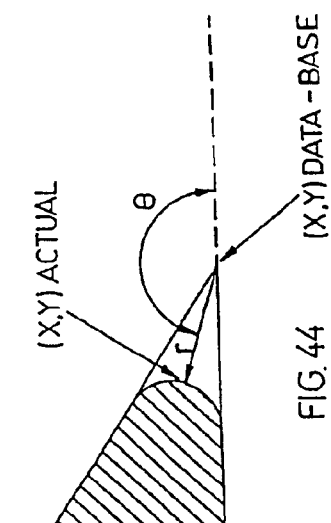
FIGS. 44, 45 and 46 further diagrams helpful in explaining the operation of the system of FIG. 40.

The corner shift can be further understood using FIG. 44. The actual location of the corner is calculated as follows:

X actual=X database+ΔX
Y actual=Y database+ΔY where:

X=r cos 8
Y=r sin 8
and 8=θ45°t

The scattering intensities for different values of C are measured and saved for $0 \leq \alpha \leq 360$ for detector $D_1$ and for the three kinds of curves. The scattering function is $g(k,\alpha, C)$. A typical function g is described in FIG. 45.

Figure 45:
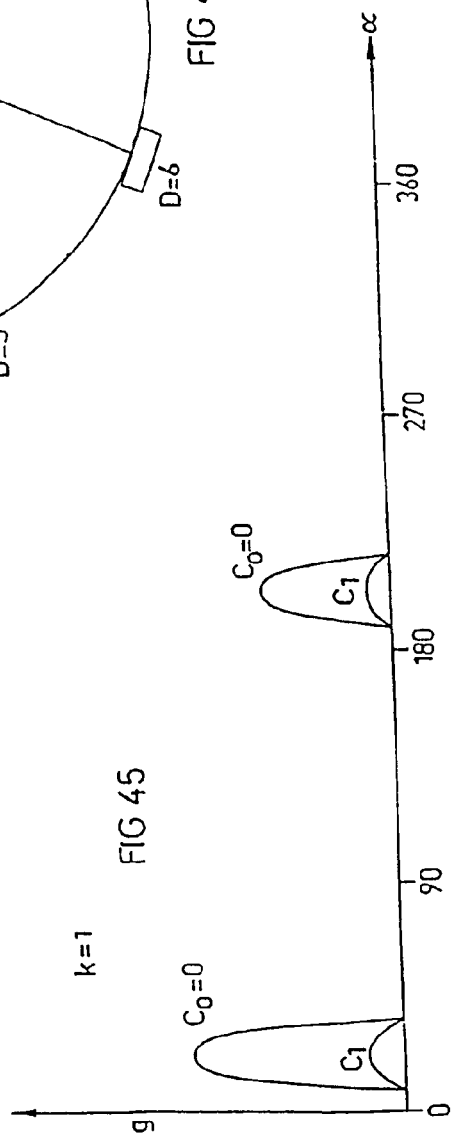
Figure 46:
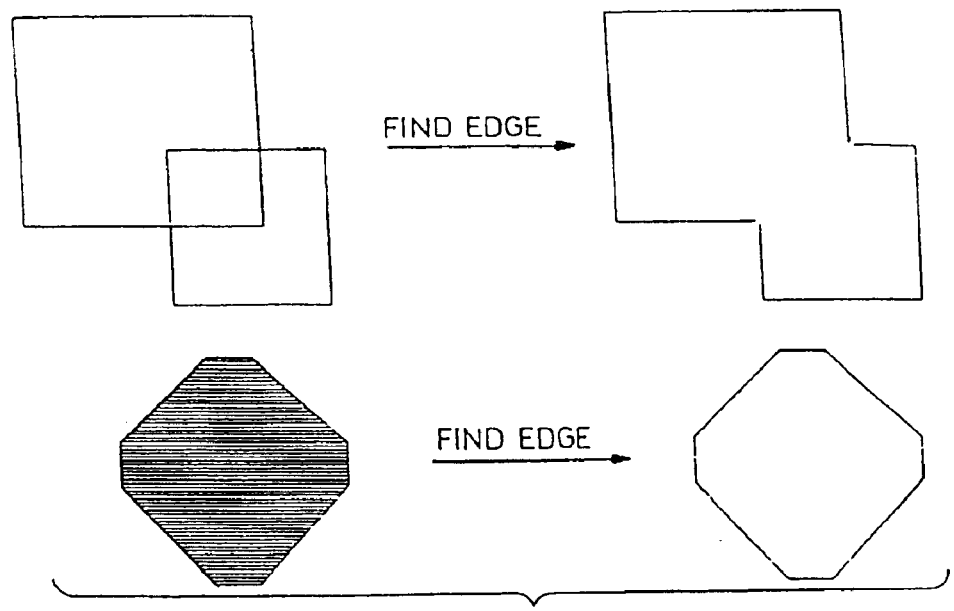

FIG. 45 is an example of g(k,α,C) for k=1 (the meaning of k and a is given in FIG. 46). The function g is given for a number of values of curvature C when only two are shown in FIG. 45, $c_o$=0 and $c_1$>0 (in fact, the value $c_o$=0 refers to a straight line—k=3).

The scattering intensities for the other detectors are calculated by:

$$I(k,\alpha,C,D)=g(k,\alpha-45X(D-1), C)$$

As a last step, the spatial distribution of the scattered intensity in the image plane is calculated by convolving in convolver 404 the high-resolution scattering image with the point-spread function of the electro-optical system used for imaging acquisition.

Figure 47:
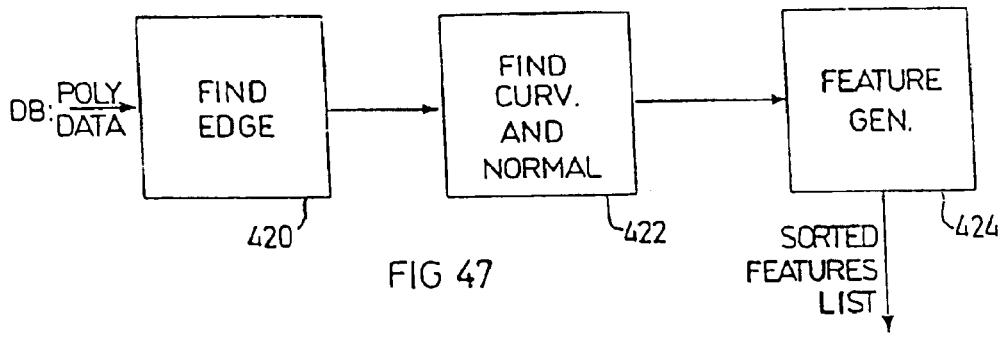
FIG. 47 is a block diagram illustrating the preprocessor in the system of FIG. 40.

The task of the preprocessor 400 (FIG. 47) is to generate the list of features defining the object, as described above, as provided by the database. The translation of the polygons data in the database into a features list is done in the following steps, as illustrated in FIG. 47.

1. FIND EDGE (block 420, FIG. 47)—Translate polygons data in the database into vector representations describing actual edges of the pattern. FIG. 46 provides two examples of the translation. In the present embodiment this step is done by using the Scanline algorithm from "Computational Geometry" by Preparata F. P. and Shamos M. I. Springer-Verlag, New-York Inc. The output of this step to a list of segments or vectors AB, BC—etc., each of which is represented by its two end points. The segments are ordered in sets; each set represents the contour of a shape.

2. FIND CURVATURE & NORMAL—(block 422, FIG. 47)—Find associates curvature and normal to each segment. For each segment in a set, the curvature and normal are computed using the neighboring segments in the set. In the present embodiment this step is done using the algorithm of Pavlidis T., Curve Fitting with Conic Splines ACM Tran.On Graphics, 2 (1983) pp. 1–31. The output of this step is a list of segments, each of which is associated with two end points, curvature and normal. The segments are still grouped in sets representing contours.

3. FEATURE GENEATOR—(block 424). Generates a list of features. In each set of segments, corners are detected and the location, kind and orientation, as defined above, are computed. For each segment its length, location and kind are computed. The output of this step is a list of features described by class, location, and characteristics.

Figure 48:
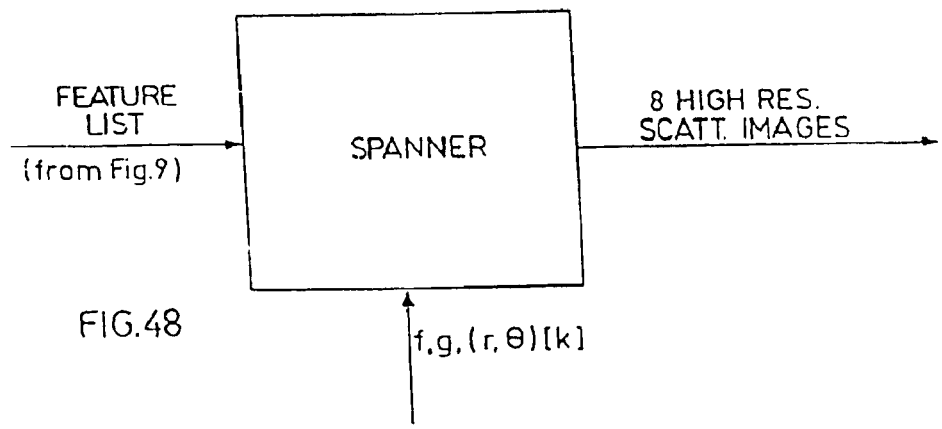
FIG. 48 is a block diagram helpful in explaining the operation of the spanner in the system of FIG. 40.

A general block-diagram of the spanner (402, FIG. 40) is illustrated in FIG. 48. The spanner has two inputs: The first input contains a sorted feature list, as described above. The second input contains the model data f, g, (r, θ). As described above. The function (f g) simulates the scattering signals for the corners (f) and the curves (g), respectively; whereas the function (r,θ) simulates the shift (rounding) of the corners by the manufacturing process, as illustrated in FIG. 13. The spanner uses the feature data and the model data in order to generate eight high-resolution scattering images.

Figure 49:
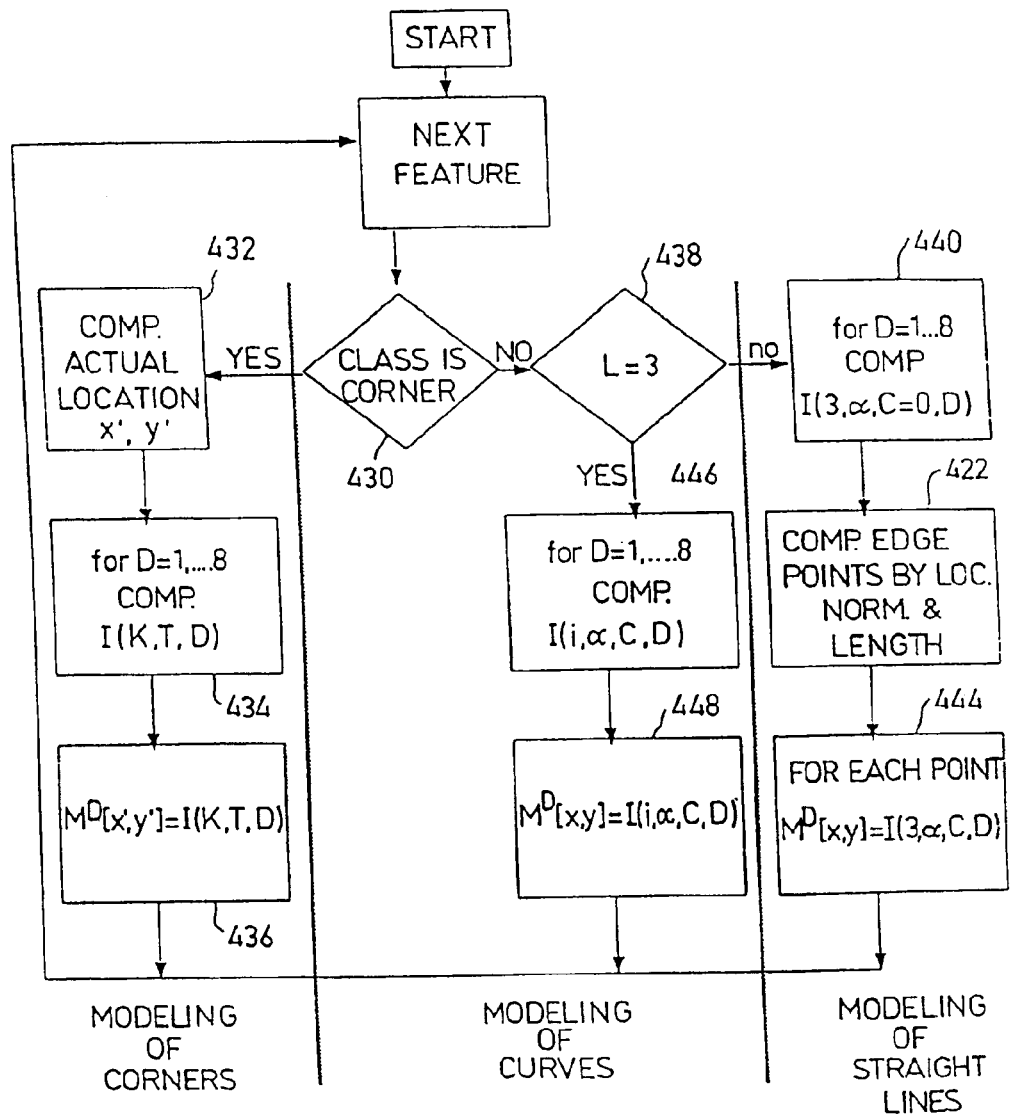
FIG. 49 is a flow chart illustrating the operation of the spanner in the system of FIG. 40.

The method used for generating these images can be further understood using FIG. 49. The spanner (402, FIGS. 40 and 17) first classifies the feature to be either a corner or a curve (block 430) and then uses the appropriate model in order to calculate the scattering intensities from the features. Since a straight line (curve of kind k=3) consists of L segments, the same scattering intensity is associated with each segment of the line.

Thus, as shown in the flow chart of FIG. 49, if the feature is determined to be a corner, the system computes the actual location (x', y') as shown in block 432; then computes the intensity I(k,t,D) for each detector $D_1$–$D_8$ (block 434); and then assigns the correct intensity in the right location for each detector (block 436).

On the other hand, if the feature is determined not to be a corner (i.e., a curve), a check is made to determine the kind of curve. Thus, if "k" is not a straight line as shown in FIG. 42 (block 436), a computation is made of the intensity (block 440), and of the edge points of the segment (block 442); and then the correct intensity is assigned to the correct location (block 444). On the other hand, if the feature is determined to be a curve (block 438), a computation is made of the intensity (block 446), and then the correct intensity is assigned in the correct location for each detector (block 448).

The convolver (block 404, FIG. 40) carries out a convolution on the high-resolution image input. The kernel of the convolver simulates the point-spread function of the electro-optical image. The output of the convolver is an image with a pixel size which is identical to the one of the acquired image. Such convolvers are well known.

The adjustment unit (block 406, FIG. 40) uses input images of known curves and corners in order to build the models for f, g and (r, θ). The images used for adjustment purposes may be known test patterns. The adjustment process is made prior to inspection and may be done once for each type of product. The models of f, g and (r, θ) are used by the scanner as described above.

In the preferred embodiments of the invention described above, both the Phase I examination and the Phase II examination are effected, one automatically after the other. It is contemplated. however, that the invention, or features thereof, could also be embodied in apparatus which effects only the first examination or only the second examination. It is also contemplated that the apparatus could be supplied with the capability of effecting both examinations but with means for disabling, e.g., the second examination, if not required for any particular application. Many other variations, modifications and applications of the invention will be apparent.

What is claimed is:

1. An apparatus for inspection of a substrate, said apparatus comprising:
   an illumination source illuminating said substrate;
   first collection optics receiving light and outputting inspection signals;
   a comparator calculating a difference between said inspection signals and a reference signal to identify locations on said substrate suspected of having defects thereupon based on a threshold, and outputting suspect location data;
   second collection optics receiving light and outputting images according to said suspect location data; and
   a defect classifier receiving and classifying said images.

2. The apparatus of claim 1, wherein said illumination source is a laser.

3. The apparatus of claim 1, wherein said first collection optics comprises a plurality of sensors.

4. The apparatus of claim 3, wherein said first collection optics further comprises dark field collection optics.

5. The apparatus of claim 4, wherein said dark field collection optics includes a turret carrying a plurality of objectives thereupon.

6. The apparatus of claim 1, wherein said second collection optics comprises an imaging sensor.

7. The apparatus of claim 6, wherein said second collection optics further comprises bright field collection optics.

8. The apparatus of claim 7, wherein said bright field collection optics includes a turret carrying a plurality of objectives thereupon.

9. The apparatus of claim 1, further comprising an image processor receiving an output of said second collection optics and outputting said images.

10. The apparatus of claim 1, wherein said threshold is an adaptive threshold.

* * * * *